(12) United States Patent
Wu

(10) Patent No.: US 10,167,283 B2
(45) Date of Patent: Jan. 1, 2019

(54) β-LACTAMASE INHIBITORS AND USES THEREOF

(71) Applicants: Xuanzhu Pharma Co., Ltd., Jinan, Shandong Province (CN); SIHUAN PHARMACEUTICAL HOLDINGS GROUP LTD., Beijing (CN)

(72) Inventor: Frank Wu, Jinan (CN)

(73) Assignees: SUANZHU PHARMA CO., LTD., Jinan, Shandong Province (CN); SIHUAN PHARMACEUTICAL HOLDINGS GROUP LTD., Beijing (CN)

( * ) Notice: Subject to any disclaimer, the term of this patent is extended or adjusted under 35 U.S.C. 154(b) by 0 days.

(21) Appl. No.: 15/569,927

(22) PCT Filed: Aug. 18, 2016

(86) PCT No.: PCT/CN2016/095837
§ 371 (c)(1),
(2) Date: Oct. 27, 2017

(87) PCT Pub. No.: WO2017/045510
PCT Pub. Date: Mar. 23, 2017

(65) Prior Publication Data
US 2018/0148448 A1    May 31, 2018

(30) Foreign Application Priority Data
Sep. 16, 2015 (CN) .......................... 2015 1 0589021

(51) Int. Cl.
*C07D 471/04* (2006.01)
*C07D 471/08* (2006.01)
(Continued)

(52) U.S. Cl.
CPC .......... *C07D 471/08* (2013.01); *A61K 31/439* (2013.01); *A61K 31/535* (2013.01); *A61K 45/06* (2013.01); *A61P 31/04* (2018.01); *C07D 487/08* (2013.01); *C07D 519/00* (2013.01); *Y02A 50/471* (2018.01); *Y02A 50/473* (2018.01); *Y02A 50/475* (2018.01); *Y02A 50/481* (2018.01)

(58) Field of Classification Search
CPC .................................................... C07D 471/08
See application file for complete search history.

(56) References Cited

U.S. PATENT DOCUMENTS 7,112,592 B2    9/2006  Lampilas
2013/0225554 A1  8/2013  Maiti et al.
(Continued)

FOREIGN PATENT DOCUMENTS

CN    101406471 A    4/2009
CN    101918407 A    12/2010
(Continued)

OTHER PUBLICATIONS

Search Report dated Nov. 25, 2016, in corresponding International Application No. PCT/CN20161095837, filed Aug. 18, 2016, 12 pages.
(Continued)

*Primary Examiner* — Kahsay Habte
(74) *Attorney, Agent, or Firm* — Christensen O'Connor Johnson Kindness PLLC

(57) ABSTRACT

The present invention relates to a compound of Formula (I)-(IV) useful as β-lactamase inhibitor, a pharmaceutically acceptable salt, ester, solvate or stereoisomer thereof, wherein $R_1$, $R_2$, M and ring A have definitions as those in the specification. The present invention further relates to methods for preparing these compounds, pharmaceutical compositions comprising these compounds, and uses of these compounds. For example, the compounds of the present invention can be used as β-lactamase inhibitors, for treatment and/or prophylaxis of diseases caused by bacterial infections, solving drug-resistance problems caused by β-lactamases, especially bacterial drug-resistant diseases caused by type B metallo-β-lactamases.

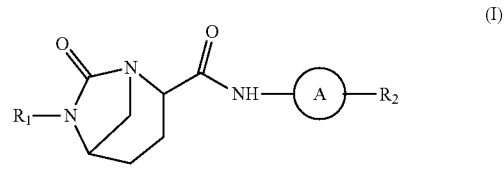

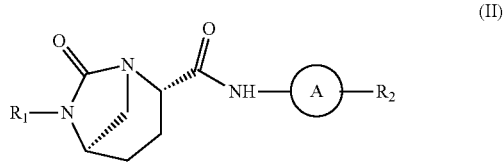

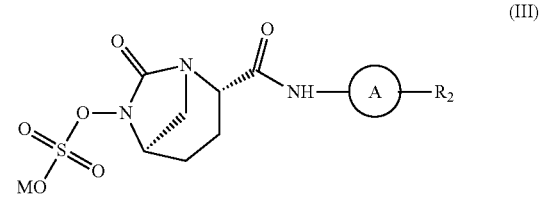

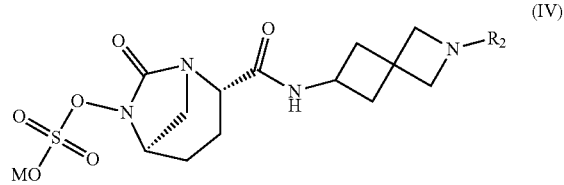

24 Claims, No Drawings

(51) Int. Cl.
A61K 31/439    (2006.01)
A61K 31/535    (2006.01)
C07D 487/08    (2006.01)
C07D 519/00    (2006.01)
A61P 31/04     (2006.01)
A61K 45/06     (2006.01)

(56)  References Cited

U.S. PATENT DOCUMENTS

2015/0374673 A1  12/2015  Das et al.
2016/0024090 A1   1/2016  Abe et al.

FOREIGN PATENT DOCUMENTS

| CN | 104334559 A    | 2/2015 |
| WO | 02/10172 A1    | 2/2002 |
| WO | 2009/091856 A2 | 7/2009 |
| WO | 2013/030733 A1 | 3/2013 |
| WO | 2013/030735 A1 | 3/2013 |
| WO | 2014/091268 A1 | 6/2014 |
| WO | 2014/122468 A1 | 8/2014 |
| WO | 2014/141132 A1 | 9/2014 |

OTHER PUBLICATIONS

Office Action dated Apr. 17, 2018, issued in Australian Application No. 2016322283, filed Aug. 18, 2016, 2 pages.
Extended European Search Report dated Jul. 12, 2018, issued in European Application No. 16845624.2, filed Aug. 18, 2016, 9 pages.
Written Opinion dated Nov. 25, 2016, issued in corresponding International Application No. PCT/CN2016/095837, filed Aug. 18, 2016, 11 pages.

β-LACTAMASE INHIBITORS AND USES THEREOF

1. TECHNICAL FIELD

The present invention relates to field of medical technology. In particular, the present invention relates to a β-lactamase inhibitor compound, a pharmaceutically acceptable salt, ester, solvate and stereoisomer thereof, a pharmaceutical composition or preparation comprising the compound, a pharmaceutically acceptable salt, ester, solvate and/or stereoisomer thereof, a method for preparing the compound, a pharmaceutically acceptable salt, ester, solvate and stereoisomer thereof, and a use of the compound, a pharmaceutically acceptable salt, ester, solvate and stereoisomer thereof.

2. BACKGROUND ART

The rapid development of antibiotics is of great significance in modern medical history. Penicillin is the first β-lactam antibiotics that is successfully used in clinic, and provides an important direction for massive application of β-lactam type antibiotics in clinic. The β-lactamases generated in cells are capable of hydrolyzing antibiotics having a β-lactam ring structure and inactivating the antibiotics, which is the most common mechanism of bacterial resistance to β-lactam antibiotics. According to differences of amino acid sequences in molecular structure, β-lactamases can be divided into two main groups: one group including A, C and D types with serine as active site, and another group including metalloenzymes with metal ions (especially $Zn^{2+}$ ion) as active sites.

With the massive application of β-lactam type antibiotics, the resistance to β-lactam type antibiotics mediated by β-lactamase has become increasingly serious.

There are two thoughts in developing β-lactamase inhibitors: (1) developing a substrate of β-lactamase, reversibly/irreversibly binding to affinity site of enzyme to amidate β-lactamase, so as to enable an antibiotic co-administrated with the substrate of β-lactamase to exert effects: (2) developing a "suicide enzyme inhibitor" with relevant mechanism or being irreversible, reacting with β-lactamase to form a non-covalent Michaelis complex, incurring a serine nucleophilic attack on amido bond to open D-lactam ring, then rearrangement and so on to inactive enzyme, in which its structure is destroyed as well, and thus it is also called as suicide enzyme inhibitor.

The β-lactamase inhibitors successfully used in clinic include Clavulanic acid. Sulbactam and Tazobactam, which structures are shown as follows:

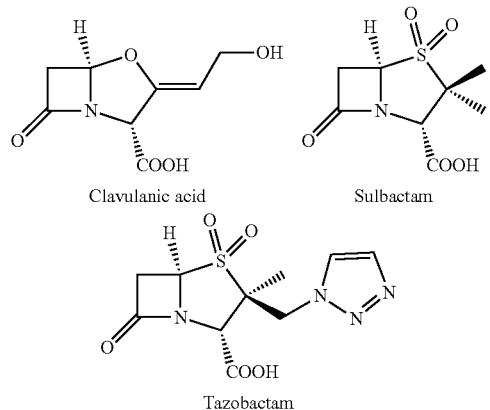

Clavulanic acid    Sulbactam

Tazobactam

Clavulanic acid was firstly separated from *Streptomyces clavuligerus* in 1970. It has a slight antibacterial activity when used alone, but it can significantly reduce minimal inhibitory concentrations of amoxicillin against *K. pneumonia, Proteus mirabilis* and *E. coli* when combined with amoxicillin. Its main enzyme spectrum is for type A β-lactamases (CTX-M, TEM-1, SHV-1, KPC, etc.), but it shows poor combination effects on resistances induced by type B metalloenzymes (IMP, NDM-1, VIM, etc.), type C enzymes (AmpC, etc.), type D enzymes (OXA, etc.) and so on. Sulbactam and Tazobactam are enzyme inhibitors separately developed in 1978 and 1980, which mainly improve inhibitory effects on type C enzymes (AmpC) and type D enzymes (OXA), but they still show poor inhibitory activity on type B metalloenzymes. In the meantime, all of the three enzyme inhibitors are structural analogues of penicillin, belong to irreversible "suicide enzyme inhibitors", and thus have short action time.

Avibactam is a diazabicyclooctanone compound, which combined with ceftazidime came into the market in the U.S. on Feb. 27, 2015. In comparison with the three β-lactamase inhibitors in the market, it is characterized by long-term of enzyme inhibitory effects, reversible covalent binding to enzyme, and not inducing generation of β-lactamases. However, it still shows poor effects on type B metalloenzymes, which significantly limits its clinical applications. In addition, since Avibactam has a short $T_{1/2}$ and multiple dosing per day is required, which results in poor compliance in patients, Avibactam does not meet clinical requirements. Like Avibactam, MK-7655 is also a diazabicyclooctanone compound, which combined with Imipenem and Cystatin in phase III clinical trials. Similar to Avibactam, its antienzymatic spectrum is broadened in comparison with the three β-lactamase inhibitors in the market, but it still shows poor pharmaceutical effects on type B metalloenzymes. In addition, its $T_{1/2}$ in clinic is only 1.7 h, requiring 4 doses per day, which would be its bottleneck in clinical applications as well. The structures of Avibactam and MK-7655 are shown as follows:

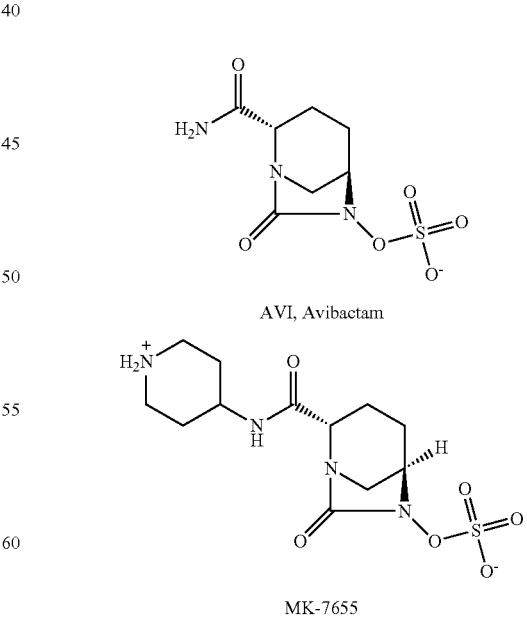

AVI, Avibactam

MK-7655

Hence, it is a new development hotspot to screen antagonizing drug-resistance β-lactamase inhibitor compounds which have a longer half-life and a low clearance rate and can be used to solve the technical problem associated with bacterial drug-resistance caused by β-lactamase. The compounds of the present invention are characterized by broader antibacterial spectrum, and can act as β-lactamase inhibitors from molecular level perspective and antibacterial agents from cellular perspective.

3. SUMMARY OF THE INVENTION

The technical problem to be solved in the present invention is to provide new compounds which can be used as β-lactamase inhibitors. The compounds can be used to solve antibiotic resistance problem caused by β-lactamases and have long half-life in vivo, and thus improving compliance in patients.

The technical solutions of the present invention are as follows:

Solution 1: A compound as shown in Formula (I), a pharmaceutically acceptable salt, ester, solvate or stereoisomer thereof,

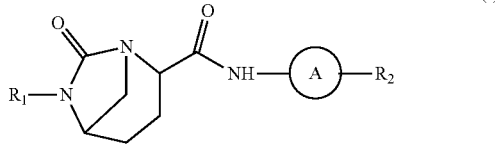

(I)

wherein, $R_1$ is —$SO_3M$, —$OSO_3M$, —$SO_2NH_2$, —$PO_3M$, —$OPO_3M$, —$CH_2CO_2M$, —$CF_2CO_2M$ or —$CF_3$;

M is selected from H or a pharmaceutically acceptable cation;

Ring A is selected from the group consisting of 5- to 15-membered bridged cyclyl, 5- to 15-membered spiro cyclyl, 5- to 15-membered bridged heterocyclyl or 5- to 15-membered spiro heterocyclyl, which is optionally substituted with substituent(s) selected from the group consisting of halogen, amino, carboxyl, hydroxyl, cyano, $C_{1-6}$ alkyl, halo $C_{1-6}$ alkyl, $C_{1-6}$ alkoxy, $C_{1-6}$ alkylamino or $C_{1-6}$ alkylcarbonyl:

$R_2$ is selected from the group consisting of hydrogen atom, halogen, amino, carboxyl, hydroxyl, $C_{1-6}$ alkyl, halo $C_{1-6}$ alkyl, hydroxyl$C_{1-6}$ alkyl, $C_{1-6}$ alkoxy, $C_{1-6}$ alkoxy-$C_{1-6}$ alkyl, halo $C_{1-6}$ alkoxy, halo $C_{1-6}$ alkoxy-$C_{1-6}$ alkyl, $C_{1-6}$ alkylamino, di($C_{1-6}$ alkyl)amino, $C_{1-6}$ alkylamino-$C_{1-6}$ alkyl, $C_{1-6}$ alkylcarbonyl, halo $C_{1-6}$ alkylcarbonyl, halo $C_{1-6}$ alkylcarbonyl-$C_{1-6}$ alkyl, $C_{1-6}$ alkylcarbonyloxy, $C_{1-6}$ alkoxycarbonyl, $C_{1-6}$ alkylcarbonyloxy-$C_{1-6}$ alkyl, $C_{1-6}$ alkylacylamino, $C_{1-6}$ alkylaminocarbonyl, di($C_{1-6}$ alkyl)aminocarbonyl, $C_{1-6}$ alkylsulfinyl, $C_{1-6}$ alkylsulfonyl, $C_{1-6}$ alkylsulfonyl$C_{1-6}$ alkyl, $C_{1-6}$ alkylsulfonylamino, $C_{1-6}$ alkylsulfonyloxy, $C_{1-6}$ alkenyl, $C_{1-6}$ alkynyl, 3- to 8-membered cycloalkyl, 3- to 8-membered cycloalkyl-$C_{1-6}$ alkyl, 6- to 8-membered aryl, 6- to 15-membered fused aryl, 4- to 15-membered fused cyclyl, 5- to 15-membered bridged cyclyl, 5- to 15-membered spiro cyclyl, 3- to 8-membered heterocyclyl, 3- to 8-membered heterocyclyl-$C_{1-6}$ alkyl, 5- to 8-membered heteroaryl, 5- to 15-membered fused heteroaryl, 4- to 15-membered fused heterocyclyl, 5- to 15-membered bridged heterocyclyl or 5- to 15-membered spiro heterocyclyl.

Solution 2: The compound, a pharmaceutically acceptable salt, ester, solvate or stereoisomer thereof according to the Solution 1, wherein the compound has the structure of Formula (II),

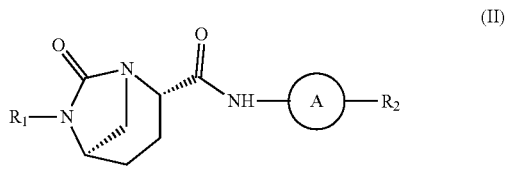

(II)

wherein, $R_1$, $R_2$, ring A are defined as those in claim 1.

Solution 3: The compound, or a pharmaceutically acceptable salt, ester, solvate or stereoisomer thereof according to any one of the Solutions 1-2, wherein the compound has the structure of Formula (III),

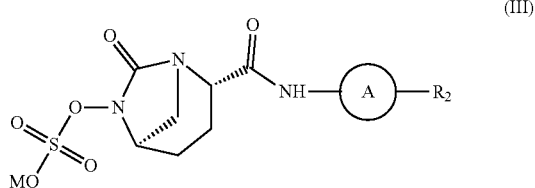

(III)

wherein,

Ring A is selected from the group consisting of 5- to 15-membered bridged heterocyclyl or 5- to 15-membered spiro heterocyclyl preferably 5- to 15-membered nitrogen-containing bridged heterocyclyl, 5- to 15-membered nitrogen-containing spiro heterocyclyl, 7- to 9-membered nitrogen-containing bridged heterocyclyl, 7- to 11-membered nitrogen-containing spiro heterocyclyl or 7- to 9-membered nitrogen-containing spiro heterocyclyl, which is optionally substituted with substituent(s) selected from the group consisting of halogen, amino, carboxyl, hydroxyl, cyano, $C_{1-6}$ alkyl, halo $C_{1-6}$ alkyl, $C_{1-6}$ alkoxy, $C_{1-6}$ alkylamino or $C_{1-6}$ alkylcarbonyl;

$R_2$ is selected from the group consisting of hydrogen atom, halogen, amino, carboxyl, hydroxyl, $C_{1-6}$ alkyl, halo $C_{1-6}$ alkyl, hydroxyl$C_{1-6}$ alkyl, $C_{1-6}$alkoxy, $C_{1-6}$ alkoxy$C_{1-6}$ alkyl, halo $C_{1-6}$ alkoxy, halo $C_{1-6}$ alkoxy$C_{1-6}$ alkyl, $C_{1-6}$ alkylamino, di($C_{1-6}$ alkyl)amino, $C_{1-6}$ alkylamino$C_{1-6}$ alkyl, $C_{1-6}$ alkylcarbonyl, halo $C_{1-6}$ alkylcarbonyl, halo $C_{1-6}$ alkylcarbonyl$C_{1-6}$ alkyl, $C_{1-6}$ alkylcarbonyloxy, $C_{1-6}$ alkoxycarbonyl, $C_{1-6}$ alkylcarbonyloxy$C_{1-6}$ alkyl, $C_{1-6}$ alkylacylamino, $C_{1-6}$ alkylaminocarbonyl, di($C_{1-6}$ alkyl) aminocarbonyl, $C_{1-6}$ alkylsulfinyl, $C_{1-6}$ alkylsulfonyl, $C_{1-6}$ alkylsulfonyl$C_{1-6}$ alkyl, $C_{1-6}$ alkylsulfonylamino, $C_{1-6}$ alkylsulfonyloxy, $C_{2-6}$ alkenyl, $C_{2-6}$ alkynyl, 3- to 8-membered cycloalkyl, 3- to 8-membered cycloalkyl-$C_{1-6}$ alkyl, 4- to 10-membered fused cyclyl, 5- to 10-membered bridged cyclyl, 5- to 10-membered spiro cyclyl, 3- to 8-membered heterocyclyl, 3- to 8-membered heterocyclyl-$C_{1-6}$ alkyl, 4- to 10-membered fused heterocyclyl, 5- to 10-membered bridged heterocyclyl or 5- to 10-membered spiro heterocyclyl;

M is selected from the group consisting of H, sodium ion, potassium ion, calcium ion, magnesium ion, zinc ion or tetra($C_{1-6}$ alkyl) quaternary ammonium ion.

Solution 4: The compound, a pharmaceutically acceptable salt, ester, solvate or stereoisomer thereof according to the Solution 3, wherein, Ring A is selected from 5- to 15-membered nitrogen-containing bridged heterocyclyl optionally substituted with substituent(s) selected from the group consisting of halogen, amino, carboxyl, hydroxyl, cyano, $C_{1-6}$ alkyl, halo $C_{1-6}$ alkyl or $C_{1-6}$alkoxy;

$R_2$ is selected from the group consisting of hydrogen atom, halogen, amino, carboxyl, hydroxyl, $C_{1-6}$ alkyl, halo $C_{1-6}$ alkyl, hydroxyl$C_{1-6}$ alkyl, $C_{1-6}$ alkoxy, halo $C_{1-6}$ alkoxy, $C_{1-6}$ alkylamino, di($C_{1-6}$ alkyl)amino, $C_{1-6}$ alkylcarbonyl, halo $C_{1-6}$ alkylcarbonyl, $C_{1-6}$ alkylcarbonyloxy, $C_{1-6}$ alkylacylamino, $C_{1-6}$ alkylsulfinyl, $C_{1-6}$ alkylsulfonyl, $C_{1-6}$ alkylsulfonylamino, 3- to 8-membered cycloalkyl, preferably 3- to 6-membered cycloalkyl, 3- to 8-membered cycloalkyl-$C_{1-6}$ alkyl, preferably 3- to 6-membered cycloalkyl-$C_{1-6}$ alkyl, 3- to 8-membered heterocyclyl, preferably 3- to 6-membered heterocyclyl, 4- to 10-membered fused heterocyclyl, 5- to 10-membered bridged heterocyclyl or 5- to 10-membered spiro heterocyclyl:

M is selected from the group consisting of H, sodium ion, potassium ion, zinc ion or tetrabutylammonium ion.

Solution 5: The compound, a pharmaceutically acceptable salt, ester, solvate or stereoisomer thereof according to the Solution 4, wherein, Ring A is selected from 5- to 9-membered nitrogen-containing bridged heterocyclyl optionally substituted with substituent(s) selected from the group consisting of halogen, amino, carboxyl, hydroxyl or $C_{1-4}$ alkyl;

$R_2$ is selected from the group consisting of hydrogen atom, halogen, amino, carboxyl, hydroxyl, $C_{1-4}$ alkyl, halo $C_{1-4}$ alkyl, $C_{1-4}$ alkoxy, halo $C_{1-4}$ alkoxy, $C_{1-4}$ alkylcarbonyl, $C_{1-4}$ alkylsulfonyl, 5- to 6-membered cycloalkyl or 5- to 6-membered heterocyclyl.

Solution 6: The compound, a pharmaceutically acceptable salt, ester, solvate or stereoisomer thereof according to the Solution 5, wherein, Ring A is selected from 7- to 9-membered nitrogen-containing heterocyclyl, preferably saturated 7- to 9-membered nitrogen-containing bridged heterocyclyl, which is optionally substituted with substituent(s) selected from the group consisting of fluorine atom, chlorine atom, bromine atom, amino, hydroxyl, methyl, ethyl or propyl;

$R_2$ is selected from the group consisting of hydrogen atom, fluorine atom, chlorine atom, amino, hydroxyl, methyl, ethyl, trifluoromethyl, methoxy, trifluoromethoxy, acetyl, methylsulfonyl, cyclopentyl, cyclohexyl, pyrrolidinyl, imidazolidinyl, oxazolidinyl, tetrahydrofuryl, tetrahydropyranyl, piperidyl or morpholinyl.

Solution 7: The compound, a pharmaceutically acceptable salt, ester, solvate or stereoisomer thereof according to the Solution 6, wherein, Ring A is selected from the group consisting of 2-azabicyclo[2.2.1]heptyl, 7-azabicyclo[2.2.1]heptyl, 3-azabicyclo[3.2.1]octyl, 8-azabicyclo[3.2.1]octyl, 2-azabicyclo[3.2.1]octyl, 2-azabicyclo[2.2.2]octyl, 2,5-di azabicyclo[2.2.1]heptyl, 3,8-diazabicyclo[3.2.1]octyl, 2-oxa-5-azabicyclo[2.2.1]heptyl, 8-oxa-3-azabicyclo[3.2.1]octyl, 3,8-diazabicyclo[3.2.1]oct-6-enyl or 3,9-diazabicyclo[3.3.1]nonyl, which is optionally substituted with substituent(s) selected from the group consisting of fluorine atom, chlorine atom, amino, hydroxyl, methyl, ethyl or propyl;

$R_2$ is selected from the group consisting of hydrogen atom, fluorine atom, chlorine atom amino, hydroxyl, methyl, ethyl, trifluoromethyl, methoxy, trifluoromethoxy, acetyl, methylsulfonyl, cyclohexyl, pyrrolidinyl, piperidyl or morpholinyl.

Solution 8: The compound, a pharmaceutically acceptable salt, ester, solvate or stereoisomer thereof according to the Solution 3, wherein, Ring A is selected from 5- to 15-membered nitrogen-containing spiro heterocyclyl optionally substituted with substituent(s) selected from the group consisting of halogen, amino, carboxyl, hydroxyl, cyano, $C_{1-6}$ alkyl, halo $C_{1-6}$ alkyl or $C_{1-6}$ alkoxy;

$R_2$ is selected from the group consisting of hydrogen atom, halogen, amino, carboxyl, hydroxyl, $C_{1-6}$ alkyl, halo $C_{1-6}$ alkyl, hydroxyl-$C_{1-6}$ alkyl, $C_{1-6}$ alkoxy, halo $C_{1-6}$ alkoxy, $C_{1-6}$ alkylamino, di($C_{1-6}$ alkyl)amino, $C_{1-6}$ alkylcarbonyl, halo $C_{1-6}$ alkylcarbonyl, $C_{1-6}$ alkylcarbonyloxy, $C_{1-6}$ alkylacylamino, $C_{1-6}$ alkylsulfinyl, $C_{1-6}$ alkylsulfonyl, $C_{1-6}$ alkylsulfonylamino, 3- to 8-membered cycloalkyl, 3- to 8-membered cycloalkyl-$C_{1-6}$ alkyl, 3- to 8-membered heterocyclyl, 5- to 9-membered fused heterocyclyl, 6- to 9-membered bridged heterocyclyl or 6- to 9-membered spiro heterocyclyl.

Solution 9: The compound, a pharmaceutically acceptable salt, ester, solvate or stereoisomer thereof according to the Solution 8, wherein, Ring A is selected from 7- to 11-membered nitrogen-containing spiro heterocyclyl optionally substituted with substituent(s) selected from the group consisting of halogen, amino, carboxyl, hydroxyl or $C_{1-4}$ alkyl;

$R_2$ is selected from the group consisting of hydrogen atom, halogen, amino, carboxyl, hydroxyl, $C_{1-4}$ alkyl, halo $C_{1-4}$ alkyl, $C_{1-4}$ alkoxy, halo $C_{1-4}$ alkoxy, $C_{1-4}$ alkylcarbonyl, $C_{1-4}$ alkylsulfonyl, 3- to 6-membered cycloalkyl, 3- to 6-membered cycloalkyl-$C_{1-4}$ alkyl or 5- to 6-membered heterocyclyl.

Solution 10: The compound, a pharmaceutically acceptable salt, ester, solvate or stereoisomer thereof according to the Solution 9, wherein, Ring A is selected from 7- to 9-membered nitrogen-containing spiro heterocyclyl, preferably saturated 7- to 9-membered nitrogen-containing spiro heterocyclyl, which is optionally substituted with substituent(s) selected from the group consisting of fluorine atom, chlorine atom, bromine atom, amino, hydroxyl, methyl, ethyl or propyl;

$R_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclopentyl, cyclohexyl, pyrrolidinyl, imidazolidinyl, oxazolidinyl, tetrahydrofuryl, tetrahydropyranyl, piperidyl or morpholinyl.

Solution 11: The compound, a pharmaceutically acceptable salt, ester, solvate or stereoisomer thereof according to the Solution 10, wherein, Ring A is selected from 8- to 9-membered nitrogen-containing spiro heterocyclyl, preferably saturated 8- to 9-membered nitrogen-containing spiro heterocyclyl, which is optionally substituted with substituent(s) selected from the group consisting of fluorine atom, chlorine atom, bromine atom, amino, hydroxyl, methyl, ethyl or propyl;

$R_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclopentyl, cyclohexyl, pyrrolidinyl, tetrahydrofuryl, tetrahydropyranyl, piperidyl or morpholinyl.

Solution 12: The compound, a pharmaceutically acceptable salt, ester, solvate or stereoisomer thereof according to the Solution 10, wherein, Ring A is selected from 7-membered nitrogen-containing spiro heterocyclyl, preferably saturated 7-membered nitrogen-containing spiro heterocyclyl, which is optionally substituted with substituent(s) selected from the group consisting of fluorine atom, chlorine atom, bromine atom amino, hydroxyl, methyl, ethyl or propyl;

$R_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclopentyl, cyclohexyl, pyrrolidinyl, tetrahydrofuryl, tetrahydropyranyl, piperidyl or morpholinyl.

Solution 13: The compound, a pharmaceutically acceptable salt, ester, solvate or stereoisomer thereof according to any one of the Solution 10 or 12, wherein, Ring A is selected from the group consisting of 5-azaspiro[2.4]heptyl, 2-azaspiro[3.3]heptyl, 2-azaspiro[3.5]nonyl, 2,6-diazaspiro[3.3]heptyl, 2-oxa-6-azaspiro[3.3]heptyl, 6-oxa-2-azaspiro[3.4]octyl, 2-azaspiro[3.4]octyl, 6-azaspiro[3.4]octyl, 2-azaspiro[4.4]nonyl, 2-oxa-7-azaspiro[4.4]nonyl, 6-azaspiro[3.4]oct-7-enyl, 2-oxa-6-azaspiro[3.4]oct-7-enyl or 2-azaspiro[4.4]non-7-enyl, which is optionally substituted with substituent(s) selected from the group consisting of fluorine atom, chlorine atom, amino, hydroxyl, methyl, ethyl or propyl;

$R_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclohexyl, pyrrolidinyl, piperidyl or morpholinyl.

In the Solution 1-13, the linking site between the ring A and 2-acylamino of parent nucleus is preferably a ring carbon atom of the ring A.

Solution 14: The compound, a pharmaceutically acceptable salt, ester, solvate or stereoisomer thereof according to the Solution 13, wherein, Ring A is selected from 2-azaspiro[3.3]heptyl optionally substituted with substituent(s) selected from the group consisting of fluorine atom, chlorine atom, amino, hydroxyl, methyl, ethyl or propyl;

$R_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclohexyl, pyrrolidinyl, piperidyl or morpholinyl.

Solution 15: The compound, a pharmaceutically acceptable salt, ester, solvate or stereoisomer thereof according to the Solution 14, wherein, Ring A is selected from 2-azaspiro[3.3]heptyl optionally substituted with substituent(s) selected from the group consisting of fluorine atom, chlorine atom, amino, hydroxyl, methyl, ethyl or propyl, wherein the 2-azaspiro[3.3]heptyl links to the acylamino of parent nucleus via a ring carbon atom;

$R_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclohexyl, pyrrolidinyl, piperidyl or morpholinyl;

M is selected from the group consisting of hydrogen atom, sodium ion, potassium ion, zinc ion or tetrabutylammonium ion.

Solution 16: The compound, a pharmaceutically acceptable salt, ester, solvate or stereoisomer thereof according to the Solution 15, wherein the compound has a structure of Formula (IV),

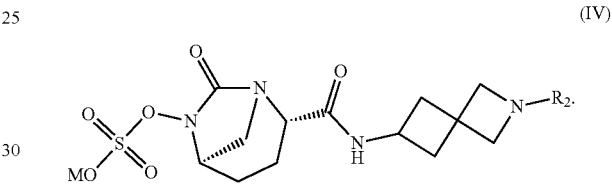

(IV)

In any one of the above solutions, any different substituents may be combined between each other to form new technical solutions, and all these new technical solutions fall into the scope of the present invention.

Solution 17: The compound, a pharmaceutically acceptable salt, ester, solvate or stereoisomer thereof according to the Solution 1, wherein the compound is selected from the group consisting of the following table:

| Comp. | Structure Formula |
|---|---|
| 1 | |
| 1-1 | |
| 1-2 | |

-continued

| Comp. | Structure Formula |
|---|---|
| 2 | |
| 2-1 | |
| 2-2 | |
| 3 | |
| 3-1 | |
| 4 | |
| 4-1 | |
| 4-2 | |

-continued

| Comp. | Structure Formula |
|---|---|
| 4-3 | |
| 4-4 | |
| 4-5 | |
| 5 | |
| 5-1 | |
| 5-2 | |
| 5-3 | |
| 5-4 | |

-continued

| Comp. | Structure Formula |
|---|---|
| 5-5 | |
| 6 | |
| 6-1 | |
| 6-2 | |
| 7 | |
| 7-1 | |
| 7-2 | |
| 8 | |

-continued
| Comp. | Structure Formula |
|---|---|
| 8-1 | 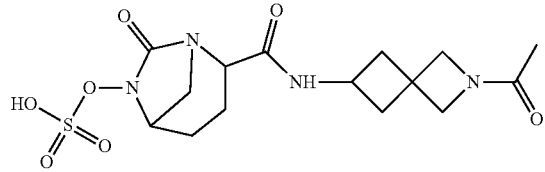 [SMILES: CC(=O)N1CC2(CC(NC(=O)[C@@H]3CC[C@@H]4CN3C(=O)N4OS(=O)(=O)O)C2)C1] |
| 9 | 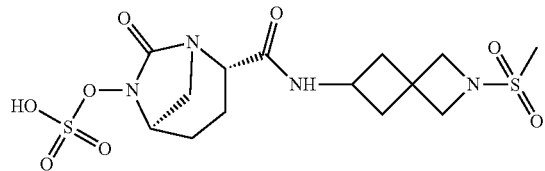 [SMILES: CS(=O)(=O)N1CC2(CC(NC(=O)[C@@H]3CC[C@@H]4CN3C(=O)N4OS(=O)(=O)O)C2)C1] |
| 9-1 | 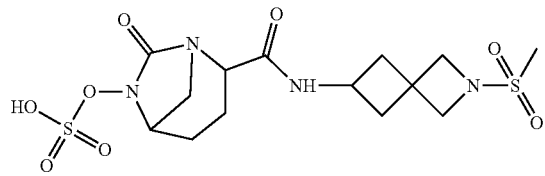 [SMILES: CS(=O)(=O)N1CC2(CC(NC(=O)C3CCC4CN3C(=O)N4OS(=O)(=O)O)C2)C1] |
| 10 | 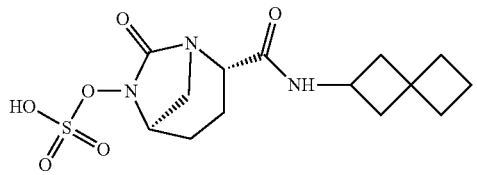 [SMILES: O=C(NC1CC2(CCC2)C1)[C@@H]1CC[C@@H]2CN1C(=O)N2OS(=O)(=O)O] |
| 10-1 | 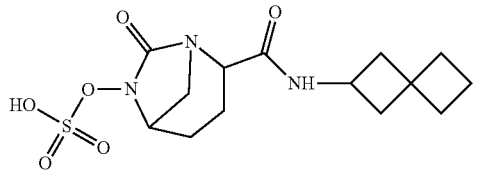 [SMILES: O=C(NC1CC2(CCC2)C1)C1CCC2CN1C(=O)N2OS(=O)(=O)O] |
| 11 | 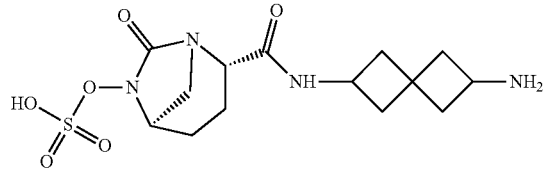 |
| 11-1 | 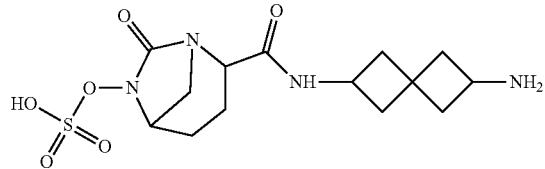 [SMILES: NC1CC2(C1)CC(NC(=O)C1CCC3CN1C(=O)N3OS(=O)(=O)O)C2] |
| 12 | 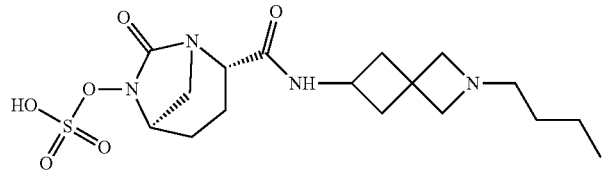 [SMILES: CCCCN1CC2(CC(NC(=O)[C@@H]3CC[C@@H]4CN3C(=O)N4OS(=O)(=O)O)C2)C1] |

-continued
| Comp. | Structure Formula |
|---|---|
| 12-1 | 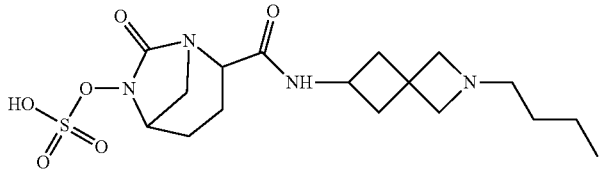 |
| 13 | 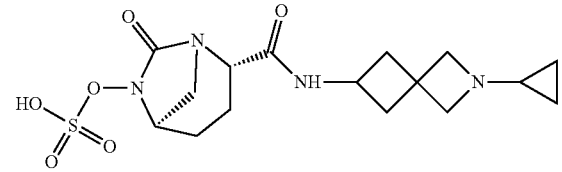 [SMILES: O=C(NC1CC2(C1)CN(C1CC1)C2)[C@@H]1CC[C@@H]2CN1C(=O)N2OS(=O)(=O)O] |
| 13-1 | 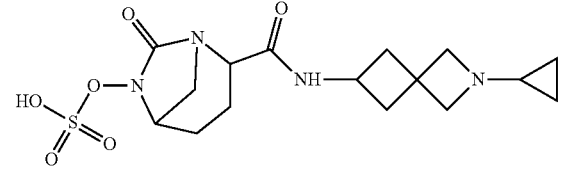 |
| 13-2 | 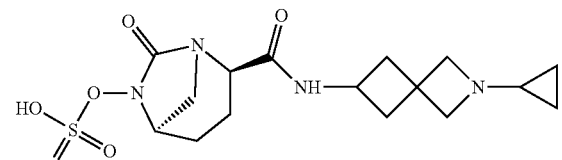 |
| 14 | 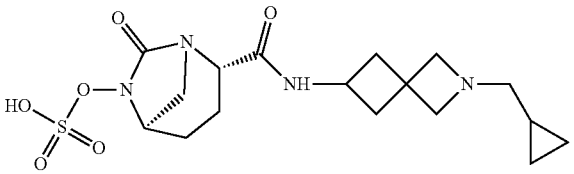 [SMILES: O=C(NC1CC2(C1)CN(CC1CC1)C2)C1CCC2CN1C(=O)N2OS(=O)(=O)O] |
| 14-1 | 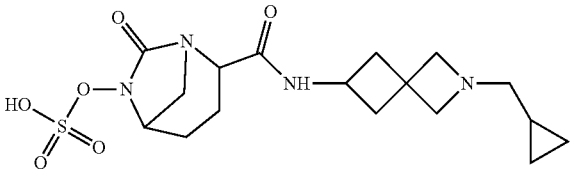 |
| 14-2 | 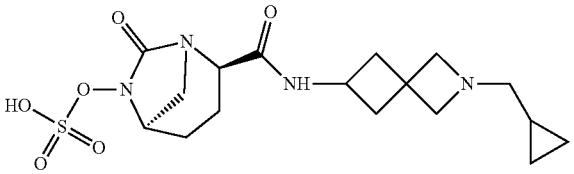 [SMILES: O=C(NC1CC2(C1)CN(CC1CC1)C2)[C@H]1CC[C@@H]2CN1C(=O)N2OS(=O)(=O)O] |
| 15 | 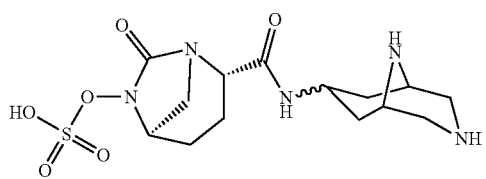 [SMILES: O=C(NC1CC2CNCC(C1)N2)[C@@H]1CC[C@@H]2CN1C(=O)N2OS(=O)(=O)O] |

| Comp. | Structure Formula |
|---|---|
| 15-1 | 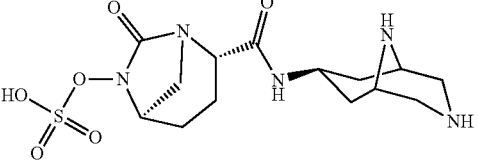 |
| 15-2 | 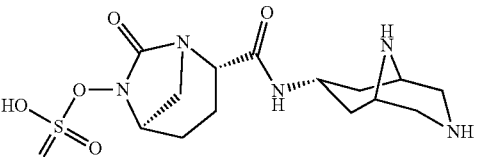 |

The present invention further relates to a variety of uses of the compounds disclosed in the present invention. Thus, the present invention further relates to the following exemplified technical solutions.

Solution 18: A pharmaceutical composition, which comprises pharmaceutical formulation of the compound, a pharmaceutically acceptable salt, ester, solvate or stereoisomer thereof according to any one of the Solutions 1-17, is characterized by comprising one or more pharmaceutically acceptable carrier and/or diluent.

Solution 19: A pharmaceutical composition, which comprises the compound, a pharmaceutically acceptable salt, ester, solvate or stereoisomer thereof according to any one of the Solutions 1-17, is characterized by comprising one or more second therapeutically active agents, wherein the second therapeutically active agents are selected from the group consisting of: antibiotics, anti-inflammatory agents, matrix metallo-proteinase inhibitors, lipoxygenase inhibitors, cytokine antagonists, immunosuppressors, anticancer agents, antiviral agents, growth factor regulators, immuno-regulators or compounds against excessive proliferation of blood vessels.

Solution 20: A use of the compound, a pharmaceutically acceptable salt, ester, solvate or stereoisomer thereof according to any one of the Solutions 1-17 in manufacture of a β-lactamase inhibitor medicament for treating and/or preventing bacterial drug-resistant diseases caused by β-lactamases, wherein the bacterial drug-resistant diseases are selected from those caused by type A β-lactamases (CTX-M, TEM-1 or SHV-1), type B metallo-β-lactamases (NDM-1, IMP or VIM), type C β-lactamases (AmpC), type D β-lactamases (OXA), preferably those caused by type B metallo-β-lactamases (NDM-1, IMP or VIM); the bacterium is selected from gram-positive bacterium or gram-negative bacterium, preferably gram-negative bacterium; the gram-positive bacterium is selected from one or more of Staphylococcus aureus, Staphylococcus epidermidis, Streptococcus agalactiae, Enterococcus faecalis, Streptococcus pneumoniae, Streptococcus pyogenes, Enterococcus faecium, or Clostridium difficile; and the gram-negative bacterium is selected from one or more of Citrobacter, Citrobacter freundii, Enterobacter cloacae, Klebsiella pneumoniae, Escherichia coli, Proteus vulgaris, salmonella, Serratia marcescens, Shiga's bacillus, Pseudomonas aeruginosa, Mucositis mora bacteria, Neisseria gonorrhoeae, Neisseria meningitidis, Diplococcus gonorrhoeae, Acinetobacter Species, Burkholderia Species, Bacterium flexuosus, Helicobacter pylori, Bacillus comma, Klebsiella, Haemophilus influenzae, Mycobacterium avium complex, Mycobacterium abscessus, Mycoboterium kansasii, Mvcobacterium ulcerans, Chlamydophila pneumoniae, Chlamydia trachomatis, Haemophilus influenzae, Streptococcus pyogenes, β-Streptococcus hemolyticus, Acinetobacter baumannii, Pseudomonas aeruginosa, Bacteroides fragilis, Bacillus cereus or Stenotrophomonas maltophilia.

Solution 21: A use of the compound, or a pharmaceutically acceptable salt, ester, solvate or stereoisomer thereof according to any one of solutions 1-17 in manufacture of a medicament for treating and/or preventing infectious diseases caused by bacteria, wherein the infectious diseases caused by bacteria, are one or more selected from the group consisting of: upper respiratory tract infection, lower respiratory tract infection, complicated urinary tract infection and other urinary tract infection, central nervous system infection, ear infection, infections of pleura, lung and bronchia, pulmonary tuberculosis, co-occurring or non-co-occurring urinary tract infection, intra-abdominal infection, cardiovascular infection, bloodstream infection, septicemia, bacteremia, CNS infection, skin or soft-tissue infection, GI infection, bone and joint infection, genital infection, eye infection, granuloma infection, co-occurring or non-co-occurring skin and skin structure infections, catheter-related infection, pharyngitis, sinusitis, otitis extern, otitis media, bronchitis, empyema, pneumonia, community-acquired bacterial pneumonia, hospital acquired pneumonia, hospital acquired bacterial pneumonia, ventilator-associated pneumonia, diabetic foot infection, vancomycin-resistant enterococcus infection, urocystitis and nephropyelitis, renal calculus, prostatitis, peritonitis, complicated intra-abdominal infections and other intra-abdominal infections, dialysis-associated peritonitis, viscera, endocarditis, myocarditis, pericarditis, infusion-related septicemia, meningitis, cerebritis, brain abscess, osteomyelitis, arthritis, genital ulcer, urethritis, vaginitis, cervicitis, gingivitis, conjunctivitis, keratitis, entophthalmia, infections in cystic fibrosis patients or infections in febrile neutropenia patients.

DETAILED DESCRIPTION OF THE INVENTION

In the description and claims of the present application, chemicals are named according to chemical structure formula: however, when name and chemical structure formula of the same one compound are not consistent, chemical structure formula or chemical reaction scheme shall prevail.

In the present application, all scientific and technological terms used herein have common meanings known by those skilled in the art unless otherwise indicated. However, some terms are provided with definitions and explanations for better understanding the present invention. In addition, when the definitions and explanations of terms as provided in the present application are not consistent with their common meanings in the art, the definitions and explanations of terms as provided in the present invention shall prevail.

In the present invention, "halo-" refers to being substituted with "halogen atom", in which "halogen atom" refers to fluorine atom, chlorine atom, bromine atom, iodine atom, etc.

In the present invention, "$C_{1-6}$ alkyl" refers to a straight or branched alkyl containing 1-6 carbon atoms, including, for example, "$C_{1-4}$ alkyl", "$C_{1-3}$ alkyl", etc, and its specific examples include but are not limited to: methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc. In the present invention, "$C_{1-4}$ alkyl" refers to specific examples of $C_{1-4}$ alkyl with 1-4 carbon atoms.

In the present invention, "halo $C_{1-6}$ alkyl" refers to a radical derived from "$C_{1-6}$ alkyl" in which one or more hydrogen atoms are substituted with one or more "halogen atoms", and the "halogen atom" and "$C_{1-6}$ alkyl" are defined as above. In the present invention, "halo $C_{1-4}$ alkyl" refers to specific examples of halo $C_{1-6}$ alkyl with 1-4 carbon atoms.

In the present invention, "hydroxyl $C_{1-6}$ alkyl" refers to a radical derived from "$C_{1-6}$ alkyl" in which one or more hydrogen atoms are substituted with one or more "hydroxyls", and the "$C_{1-6}$ alkyl" are defined as above. In the present invention, "hydroxyl $C_{1-4}$ alkyl" refers to specific examples of hydroxyl $C_{1-6}$ alkyl with 1-4 carbon atoms.

In the present invention, "$C_{2-6}$ alkenyl" refers to a straight or branched or cyclic alkenyl which contains at least one double bond and has 2-6 carbon atoms, including, for example, "$C_{2-4}$ alkenyl", etc. Its examples include but are not limited to: ethenyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl, cyclopentenyl, 1,3-cyclopentadienyl, cyclohexenyl, 1,4-cyclohexadienyl.

In the present invention, "$C_{2-6}$ alkynyl" refers to a straight or branched alkynyl which contains at least one triple bond and has 2-6 carbon atoms, including, for example, "$C_{2-4}$ alkynyl", etc. Its examples include but are not limited to: ethynyl, propynyl, 2-butynyl, 2-pentynyl, 3-pentynyl, 4-methyl-2-pentynyl, 2-hexynyl, 3-hexynyl, 5-methyl-2-hexynyl, etc.

In the present invention, "tetra($C_{1-6}$ alkyl) quaternary ammonium ion" refers to a radical derived from "quaternary ammonium ion ($H_4N^+$)", in which 4 hydrogen atoms are substituted with one or more same or different "$C_{1-6}$ alkyl", and the "$C_{1-6}$ alkyl" are defined as above.

In the present invention, the "$C_{1-6}$alkoxy, $C_{1-6}$ alkoxy-$C_{1-6}$ alkyl, halo $C_{1-6}$alkoxy, halo $C_{1-6}$ alkoxy-$C_{1-6}$ alkyl, $C_{1-6}$ alkylcarbonyl, $C_{1-6}$ alkylcarbonyloxy, $C_{1-6}$ alkoxycarbonyl, $C_{1-6}$ alkylcarbonyloxy-$C_{1-6}$ alkyl, $C_{1-6}$ alkylamino, di($C_{1-6}$ alkyl)amino, $C_{1-6}$ alkylamino-$C_{1-6}$ alkyl, halo $C_{1-6}$, alkylcarbonyl, halo $C_{1-6}$ alkylcarbonyl-$C_{1-6}$ alkyl, $C_{1-6}$ alkylacylamino, $C_{1-6}$ alkylaminocarbonyl, di($C_{1-6}$ alkyl)aminocarbo-nyl, $C_{1-6}$ alkylsulfinyl, $C_{1-6}$ alkylsulfonylamino, $C_{1-6}$ alkylsulfonyloxy, $C_{1-6}$ alkylsulfonyl-$C_{1-6}$ alkyl, $C_{1-6}$ alkylsulfonyl, $C_{1-6}$ alkylsulfonyl-$C_{1-6}$ alkoxy" refer to radicals with linkage form of $C_{1-6}$ alkyl-O—, $C_{1-6}$ alkyl-O—$C_{1-6}$ alkyl-, halo $C_{1-6}$ alkyl-O—, halo $C_{1-6}$ alkyl-O—$C_{1-6}$ alkyl-, $C_{1-6}$ alkyl-C(O)—, $C_{1-6}$ alkyl-C(O)—O—, $C_{1-6}$ alkyl-O—C(O)—, $C_{1-6}$ alkyl-C(O)—O—$C_{1-6}$ alkyl-, $C_{1-6}$ alkyl-NH—, ($C_{1-6}$ alkyl)$_2$-N—, $C_{1-6}$ alkyl-NH—$C_{1-6}$ alkyl-, halo $C_{1-6}$ alkyl-C(O)—, halo $C_{1-6}$ alkyl-C(O)—$C_{1-6}$ alkyl-, $C_{1-6}$ alkyl-C(O)—NH—, $C_{1-6}$ alkyl-NH—C(O)—, ($C_{1-6}$ alkyl)$_2$-NH—C(O)—, $C_{1-6}$ alkyl-SO—, $C_{1-6}$ alkyl-SO$_2$—NH—, $C_{1-6}$ alkyl-SO$_2$—O—, $C_{1-6}$ alkyl-SO$_2$—$C_{1-6}$ alkyl-, $C_{1-6}$ alkyl-SO$_2$—, or $C_{1-6}$ alkyl-SO$_2$—$C_{1-6}$ alkyl-O—, wherein "$C_{1-6}$ alkyl, halo $C_{1-6}$ alkyl" are defined as above. In the present invention, "$C_{1-4}$ alkoxy, $C_{1-4}$ alkoxy-$C_{1-4}$ alkyl, halo $C_{1-4}$ alkoxy, halo $C_{1-4}$ alkoxy$C_{1-4}$ alkyl, $C_{1-4}$ alkylcarbonyl, $C_{1-4}$ alkylcarbonyloxy, $C_{1-4}$ alkoxycarbonyl, $C_{1-4}$ alkylcarbonyloxy-$C_{1-4}$ alkyl, $C_{1-4}$ alkylamino, di($C_{1-4}$ alkyl)amino, $C_{1-4}$ alkylamino-$C_{1-4}$ alkyl, halo $C_{1-4}$ alkylcarbonyl, halo $C_{1-4}$ alkylcarbonyl-$C_{1-4}$ alkyl, $C_{1-4}$ alkylacylamino, $C_{1-4}$ alkylaminocarbonyl, di($C_{1-4}$ alkyl)aminocarbonyl, $C_{1-4}$ alkylsulfinyl, $C_{1-4}$ alkylsulfonylamino, $C_{1-4}$ alkylsulfonyloxy, $C_{1-6}$ alkylsulfonyl-$C_{1-4}$ alkyl, $C_{1-4}$ alkylsulfonyl, $C_{1-4}$ alkylsulfonyl-$C_{1-4}$ alkoxy" refer to above specific examples in which alkyl has 1-4 carbon atoms.

In the present invention, "3- to 8-membered cycloalkyl" refers to saturated cyclic alkyl with 3-8 carbon atoms, including, for example, "3- to 6-membered cycloalkyl", "5- to 6-membered cycloalkyl", etc. Its specific examples include but are not limited to: cyclopropyl, cyclobutyl, cyclopentyl, cyclohexyl, cycloheptyl, cyclooctyl, etc. The "5- to 6-membered cycloalkyl" refers to a saturated cyclic alkyl having 5-6 carbon atoms.

In the present invention, "6- to 8-membered aryl" refers to monocyclic aryl having 6-8 ring carbon atoms, which examples include but are not limited to: phenyl, cyclooctatetraenyl, etc.

In the present invention, "6- to 15-membered fused aryl" refers to an unsaturated, aromatic cyclic radical having 6-15 ring carbon atoms, which is formed with 2 or more cyclic structures sharing two adjacent atoms. Its specific examples include but are not limited to naphthyl, anthryl, phenanthryl, etc. The "6- to 10-membered fused aryl" refers to specific examples of "6- to 15-membered fused aryl" with 6-10 ring carbon atoms.

In the present invention, "4- to 15-membered fused cyclyl" refers to a cyclic structure having 4-15 carbon atoms, which is formed with 2 or more cyclic structures sharing two adjacent atoms, including, for example, "4- to 11-membered fused cyclyl", "6- to 11-membered fused cyclyl", "5- to 9-membered fused cyclyl", "7- to 10-membered fused cyclyl", "4- to 12-membered fused cyclyl", "9- to 10-membered fused cyclyl", "4- to 10-membered fused cyclyl", etc, in which the carbon atoms in the cyclic structures can be optionally oxidized. Its examples include but are not limited to:

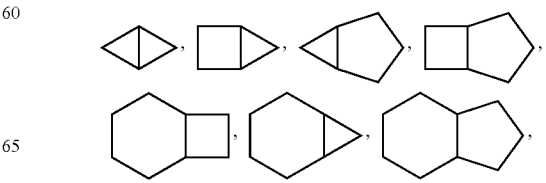

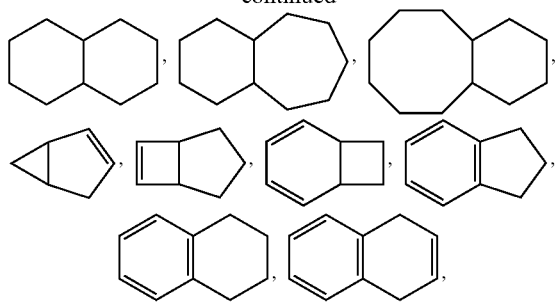

etc. The "4- to 10-membered fused cyclyl" refers to specific examples of "4- to 15-membered fused cyclyl" with 4-10 ring atoms.

In the present invention, "5- to 15-membered spiro cyclyl" refers to a cyclic structure having 5-15 ring carbon atoms, which is formed with 2 or more cyclic structures sharing one carbon atoms, in which the carbon atoms in the cyclic structures can be optionally oxidized. The examples of "5- to 15-membered spiro cyclyl" include, for example, "4- to 11-membered spiro cyclyl", "6- to 11-membered spiro cyclyl", "5- to 10-membered spiro cyclyl", "7- to 10-membered spiro cyclyl", "6- to 9-membered spiro cyclyl", "7- to 8-membered spiro cylyl" "9- to 10-membered spiro cyclyl", etc. Specific examples include but are not limited to:

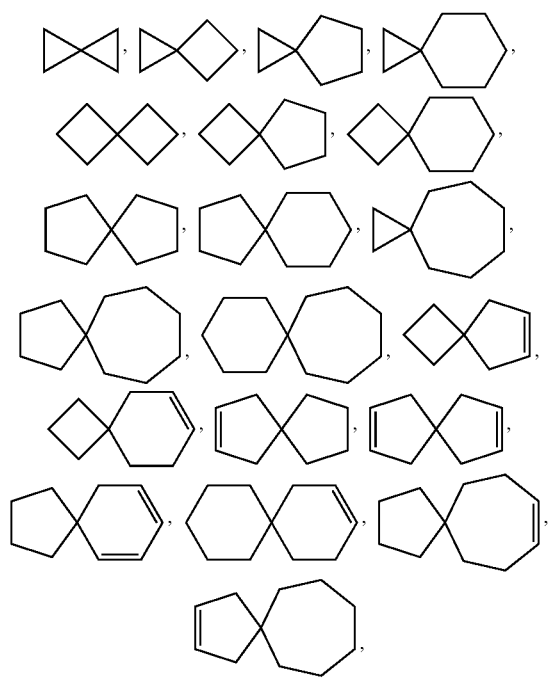

etc. The "5- to 10-membered spiro cyclyl" refer to specific examples of "5- to 15-membered spiro cyclyl" with 5-10 ring atoms.

In the present invention, "5- to 15-membered bridged cyclyl" refers to a cyclic structure having 5-15 ring carbon atoms, which is formed with 2 or more cyclic structures sharing two non-adjacent carbon atoms, in which the carbon atoms in the cyclic structures can be optionally oxidized. The examples of "5- to 15-membered bridged cyclyl" include, for example, "5- to 11-membered bridged cyclyl", "6- to 11-membered bridged cyclyl", "5- to 10-membered bridged cyclyl", "7- to 10-membered bridged cyclyl", "6- to 9-membered bridged cyclyl", "7- to 8-membered bridged cyclyl", "9- to 10-membered bridged cyclyl", etc. Specific examples include but are not limited to:

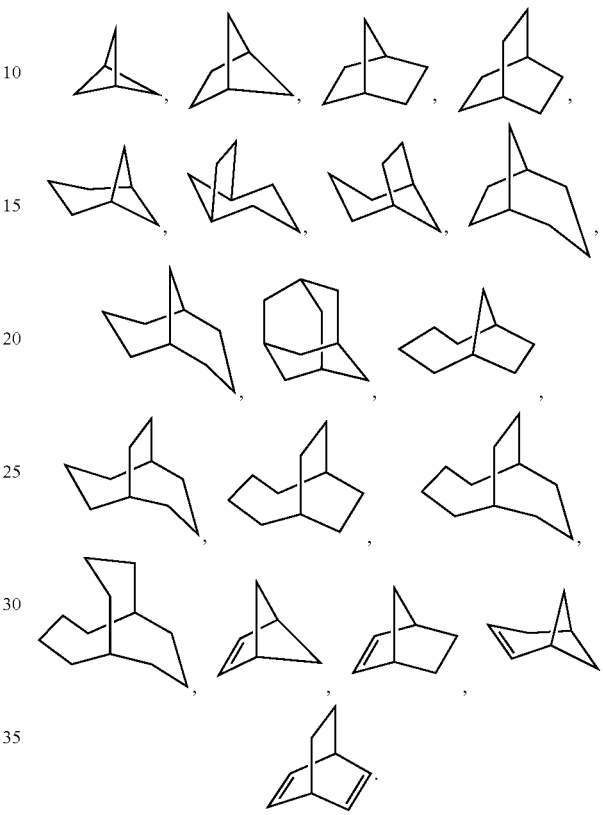

The "5- to 10-membered bridged cyclyl" refers to specific examples of "5- to 15-membered bridged cyclyl" with 5-10 ring atoms.

In the present invention, "3- to 8-membered heterocyclyl" refers to a cyclic radical with 3-8 ring atoms (wherein at least one ring atom is heteroatom, for example, nitrogen atom, oxygen atom or sulfur atom). Optionally, the ring atoms (for example, carbon atoms, nitrogen atoms or sulfur atoms) of cyclic structure can be oxidized. The examples of "3- to 8-membered heterocyclyl" include "3- to 8-membered nitrogen-containing heterocyclyl", "3- to 8-membered oxygen-containing heterocyclyl", "3- to 7-membered heterocyclyl", "3- to 6-membered heterocyclyl", "3- to 6-membered oxygen-containing heterocyclyl", "4- to 7-membered heterocyclyl", "4- to 6-membered heterocyclyl", "5- to 7-membered heterocyclyl", "5- to 6-membered heterocyclyl", "5- to 6-membered nitrogen-containing heterocyclyl", "6- to 8-membered heterocyclyl", preferably, "5- to 6-membered heterocyclyl". Specific examples include but are not limited to: azacyclopropyl, 2H-azacyclopropyl, diazacyclopropyl, 3H-diazacyclopropenyl, azacyclobutyl, 1,4-dioxacyclohexyl, 1,3-dioxacyclohexyl, 1,3-dioxacyclopentyl, 1,4-dioxacyclohexadienyl, tetrahydrofuryl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, thiazolidinyl, piperidyl, tetrahydropyridyl, piperidonyl, tetrahydropiperidonyl, dihydropiperidonyl, piperazinyl, morpholinyl, 4,5-dihydrooxazolyl, 4,5-dihydroisoxazolyl, 2,3-dihydroisoxazolyl, oxazolidinyl, 2H-1,2-oxazinyl, 6H-1,3-oxazinyl, 4H-1,3-thiazinyl, 6H-1,3-thiazinyl, 2H-pyranyl, 2H-pyran-2-onyl, 3,4-dihydro-2H-pyranyl. The "5- to 6-membered heterocyclyl" refers to specific examples of "3- to 8-membered heterocyclyl" with 5-6 ring atoms.

In the present invention, "4- to 15-membered fused heterocyclyl" refers to a cyclic structure with 4-15 ring atoms (wherein at least one ring atom is heteroatom, for example, nitrogen atom, oxygen atom or sulfur atom), which is formed with 2 or more cyclic structures sharing two adjacent atoms. Optionally, the ring atoms (for example, carbon atoms, nitrogen atoms or sulfur atoms) of cyclic structure can be oxidized. The examples of "4- to 15-membered fused heterocyclyl" include for example "4- to 12-membered fused heterocyclyl", "4- to 10-membered fused heterocyclyl", "5- to 9-membered fused heterocyclyl", "6- to 11-membered fused heterocyclyl", "7- to 9-membered fused heterocyclyl", "9- to 10-membered fused heterocyclyl", "4- to 15-membered nitrogen-containing fused heterocyclyl", "5- to 12-membered nitrogen-containing fused heterocyclyl", "6- to 10-membered nitrogen-containing fused heterocyclyl", "4- to 10-membered nitrogen-containing fused heterocyclyl", "7- to 9-membered nitrogen-containing fused heterocyclyl", "6- to 10-membered nitrogen-containing fused heterocyclyl", etc. Specific examples include but are not limited to: pyrrolidinocyclopropyl, cyclopentanoazacyclopropyl, pyrrolidinocyclobutyl, pyrrolidinopyrrolidinyl, pyrrolidinopiperidyl, pyrrolidinopiperazinyl, pyrrolidinomorpholinyl, piperdinonlmorpholinyl, benzopyrrolidinyl, tetrahydroimidazo[4,5-c]pyridyl, 3,4-dihydroquinazolinyl, 1,2-dihydroquinoxalinyl, benzo[d][1,3]dioxacyclopentenyl, 1,3-dihydroisobenzofuryl, 2H-chromenyl, 2H-chromen-2-onyl, 4H-chromenyl, 4H-chromen-4-onyl, chromanyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, benzoimidazolidinyl, octahydro-benzo[d]imidazolyl, decahydroquinolyl, hexahydrothienoimidazolyl, hexahydrofuroimidazolyl, 4,5,6,7-tetrahydro-1H-benzo[d]imidazolyl, octahydrocyclopenteno[c]pyrrolyl, dihydroindolyl, dihydroisoindolyl, benzoxazolidinyl, benzothiazolidinyl, 1,2,3,4-tetrahydroisoquinolyl, 1,2,3,4-tetrahydroquinolyl, 4H-1,3-benzooxazinyl, etc.

In the present invention, "5- to 15-membered spiro heterocyclyl" refers to a cyclic structure with 5-15 ring atoms (wherein at least one ring atom is heteroatom for example, nitrogen atom, oxygen atom or sulfur atom), which is formed with 2 or more cyclic structures sharing one ring atom, including "saturated 5- to 15-membered spiro heterocyclyl" and "partially saturated 5- to 15-membered spiro heterocyclyl". Optionally, the ring atoms (for example, carbon atoms, nitrogen atoms or sulfur atoms) of cyclic structure can be oxidized. The examples of "5- to 15-membered spiro heterocyclyl" include for example "5- to 11-membered spiro heterocyclyl", "6- to 11-membered spiro heterocyclyl", "5- to 10-membered spiro heterocyclyl", "6- to 9-membered spiro heterocyclyl", "7-9 membered spiro heterocyclyl", "9- to 10-membered spiro heterocyclyl", "5- to 15-membered nitrogen-containing spiro cyclyl", "5- to 10-membered nitrogen-containing spiro heterocyclyl", "7- to 11-membered nitrogen-containing spiro heterocyclyl", "7- to 9-membered nitrogen-containing spiro heterocyclyl", "8- to 9-membered nitrogen-containing spiro heterocyclyl", "saturated 7- to 9-membered nitrogen-containing spiro heterocyclyl", "saturated 8- to 9-membered nitrogen-containing spiro heterocyclyl", etc. Specific examples include but are not limited to:

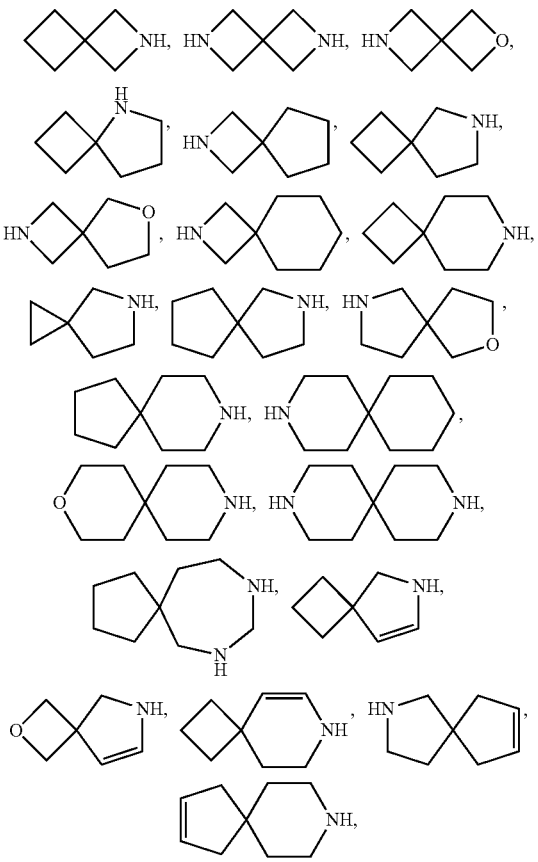

etc. The "5- to 10-membered spiro heterocyclyl" refers to specific examples of "5- to 15-membered spiro heterocyclyl" with 5-10 ring atoms.

In the present invention, "5- to 15-membered bridged heterocyclyl" refers to a cyclic structure with 5-15 ring atoms (wherein at least one ring atom is heteroatom, for example, nitrogen atom, oxygen atom or sulfur atom), which is formed with 2 or more cyclic structures sharing two non-adjacent ring atoms, including "saturated 5- to 15-membered bridged heterocyclyl" and "partially saturated 5- to 15-membered bridged heterocyclyl". Optionally, the ring atoms (for example, carbon atoms, nitrogen atoms or sulfur atoms) of cyclic structure can be oxidized. The examples of "5- to 15-membered bridged heterocyclyl" include "5- to 10-membered bridged heterocyclyl", "6- to 11-membered bridged heterocyclyl", "6- to 9-membered bridged heterocyclyl", "6- to 10-membered bridged heterocyclyl", "7- to 10-membered bridged heterocyclyl", "7- to 9-membered bridged heterocyclyl", "7- to 9-membered nitrogen-containing bridged heterocyclyl", "7- to 8-membered nitrogen-containing bridged heterocyclyl", "5- to 9-membered nitrogen-containing bridged heterocyclyl", "5- to 15-membered nitrogen-containing bridged heterocyclyl", "5- to 10-membered bridged heterocyclyl", "saturated 7- to 9-membered nitrogen-containing bridged heterocyclyl", etc. Specific examples include but are not limited to:

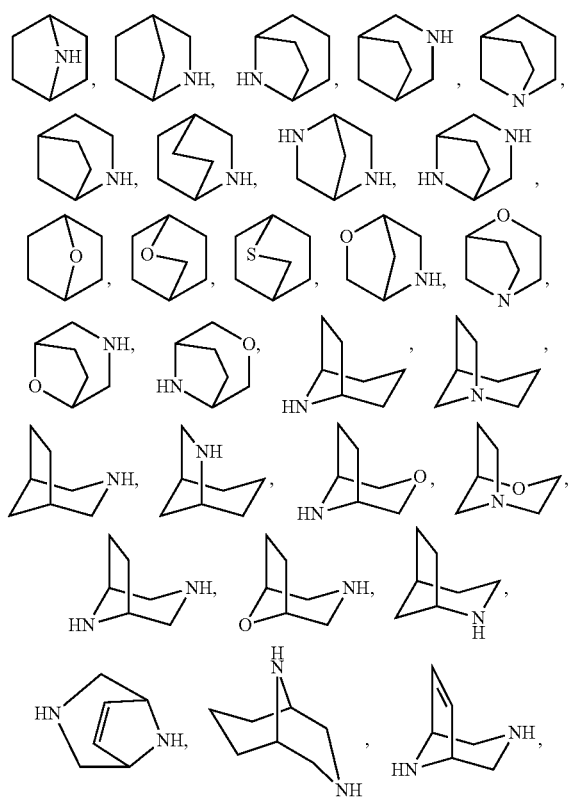

etc. The "5- to 10-membered bridged heterocyclyl" refers to specific examples of 5- to 15-membered bridged heterocyclyl with 5-10 ring atoms.

In the present invention, "5- to 8-membered heteroaryl" refers to an aromatic cyclic radical with 5-8 ring atoms (wherein at least one ring atom is heteroatom, for example, nitrogen atom, oxygen atom or sulfur atom). Optionally, the ring atoms (for example, carbon atoms, nitrogen atoms or sulfur atoms) of cyclic structure can be oxidized. The examples of "5- to 8-membered heteroaryl" include for example "5- to 7-membered heteroaryl", "5- to 6-membered heteroaryl", etc. Specific examples include but are not limited to furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidyl, pyridazinyl, pyrazinyl, 1,2,3-triazinyl, 1,3,5-triazinyl, 1,2,4,5-tetrazinyl, azacycloheptatrienyl, 1,3-diazacycloheptatrienyl, azacyclooctatetraenyl, etc. The "5- to 6-membered heteroaryl" refers to specific examples of 5- to 8-membered heteroaryl with 5-6 ring atoms.

In the present invention, "5- to 15-membered fused heteroaryl" refers to an unsaturated aromatic cyclic structure with 5-15 ring atoms (wherein at least one ring atom is heteroatom, for example, nitrogen atom, oxygen atom or sulfur atom), which is formed with 2 or more cyclic structures sharing two adjacent ring atoms. Optionally, the ring atoms (for example, carbon atoms, nitrogen atoms or sulfur atoms) of cyclic structure can be oxidized. The examples of "5- to 15-membered fused heteroaryl" include "5- to 10-membered fused heteroaryl", "7- to 10-membered fused heteroaryl", "8- to 10-membered fused heteroaryl", "9- to 10-membered fused heteroaryl", etc. Specific examples include but are not limited to: benzofuryl, benzoisofuryl, benzothienyl, indolyl, isoindolyl, benzoxazolyl, benzoimidazolyl, indazolyl, benzotriazolyl, quinolyl, 2-quinolinonyl, 4-quinolinonyl, 1-isoquinolinonyl, isoquinolyl, acridinyl, phenanthridinyl, benzopyridazinyl, phthalazinyl, quinazolinyl, quinoxalinyl, phenazinyl, pteridinyl, purinyl, naphthyridinyl, phenazinyl, phenothiazinyl, etc. The "5- to 10-membered fused heteroaryl" refers to specific examples of 5- to 14-membered fused heteroaryl with 5-10 ring atoms.

In the present invention, "carbon atoms, nitrogen atoms or sulfur atoms are oxidized" refers to the formation of C=O, N=O, S=O or SO$_2$ structures.

In the present invention, "pharmaceutically acceptable salts" of the compound of Formula (I) refers to salts formed by the acidic groups (e.g., —COOH, —OH, —SO$_3$H, etc) in the compound of Formula (I) with suitable inorganic or organic cations (alkalis), including salts formed with alkali metals or alkaline earth metals, ammonium salts, and salts formed with nitrogen-containing organic alkalis; and salts formed by the alkaline groups (e.g., —NH$_2$, etc.) in the compound of Formula (I) with suitable inorganic or organic anions (acids), including salts formed with inorganic acids or organic acids (e.g., carboxylic acids, etc.).

In the present invention, "esters" of the compound of Formula (I) refer to esters formed by esterification between the carboxyl, if existing in the compound of Formula (I), and alcohols, and esters formed by esterification between the hydroxyl, if existing in the compound of Formula (I), and organic acids, inorganic acids or salts of organic acids. The esters can be hydrolyzed to form corresponding acids or alcohols in the presence of an acid or alkali.

In the present invention, "stereoisomerism" of the compound of the present invention can be divided into conformational isomerism and configurational isomerism, and the configurational isomerism can be further divided into cis-trans isomerism and optical isomerism (enantiomerism). Conformational isomerism refers to a stereoisomerism in which an organic molecule with a certain configuration generates different steric arrangement modes of atoms or radicals caused by rotation or distortion of carbon-carbon single bond, common examples include structures of alkanes and cycloalkanes, such as chair conformation and boat conformation of cyclohexane. Optical isomers (enantiomers)" refer to that when the compound of the present invention contains one or more asymmetric centers, it can be a raceme and racemate mixture, single enantiomers, mixture of diastereomers and single diastereomers. The compound of the present invention has asymmetric centers, and these asymmetric centers can independently generate two optical isomers, respectively. The scope of the present invention covers all possible optical isomers and mixture of diastereomers and pure or partially pure compound. If the compound of the present invention contains an olefinic double bond, unless otherwise indicated, the present invention comprises its cis-isomer and trans-isomer. The compound of the present invention may exist in its tautomer forms, in which one or more double bonds shift thereby having different hydrogen-attach point. For example, ketone and its enol form are ketone-enol tautomers. All tautomers and mixtures thereof are within the scope of the compounds of the present invention. All enantiomers, diastereomers, racemes, mesomers, cis-trans isomers, tautomers, geometric isomers, epimers of the compound of formula (I) and mixtures thereof fall into the scope of the present invention.

Antibiotic resistance of bacteria is one of the most serious threat to modern health care. Infections caused by drug-resistant bacteria usually lead to longer main retention time, higher mortality rate and more therapeutic cost. Because bacteria have significant ability of generating resistance to new drugs thereby invalidating them quickly, the need of new antibiotics persistently increases. The wide use of penicillin and cephalosporins has already led to the generation of β-lactamases, and the resistance commonly mediated by β-lactamases are the key point for developing antibiotic resistance of bacteria to most of the currently used antibiotics, that is, the resistance is the result of the existence of β-lactamases. At present, available β-lactamase inhibitors are not enough to cope with ever-increasing variety of β-lactamases. Thus, more new β-lactamase inhibitors are needed. The compound of the present invention is capable of effectively combating many kinds of β-lactamases, and providing effective therapy to bacterial infections caused by microorganisms that generate type A, type B, type C and type D β-lactamases.

As used in the present invention, "β-lactamase inhibitor" refers to a compound capable of inhibiting Bβ-lactamase activity. Inhibiting β-lactamase activity refers to inhibiting activity of one or more of β-lactamases of type A, B, C and/or D. In view of anti-microorganism uses, the preferable half effective inhibition concentration is less than about 100 μg/mL, or less than about 50 μg/mL, or less than about 25 μg/mL.

As used in the present invention, "type A", "type B", "type C", "type D" β-lactamases are well known for those skilled in the art, and their meanings can be seen in Waley, The Chemistry of β-lactamase, Page Ed., Chapman & Hall, London, (1992) 198-228.

As used in the present invention, the term "β-lactamase" refers to a protein capable of inactivating β-lactam antibiotics. The β-lactamase can be an enzyme capable of catalyzing hydrolysis of β-lactam ring of β-lactam antibiotics. The present invention mainly relates to β-lactamases of microorganisms. The β-lactamase can be, for example, serine β-lactamase, including the kinds of enzymes as described in Waley, The Chemistry of β-lactamase, Page Ed., Chapman & Hall, London, (1992) 198-228. The present invention especially relates to β-lactamases including the type C β-lactamases of *Pseudomonas pyocyaneum* or *Eenterbacter cloacae*, the type B β-lactamases of *Bacteroides fragilis* (CcrA). *Klebsiella pneumoniae*, *Escherichia coli* or *Enterobacter cloacae*, *Citrobacter freundii*, *Bacillus cereus* (Bc II) or *Stenotrophomonas maltophllia* (L1), and type A and type D β-lactamases of *Klebsiella*.

As used in the present invention, the term "effective amount of β-lactamase inhibitors" refers to an amount sufficient to achieve or at least partially achieve the desired effect. For example, effective amount for prophylaxis of diseases (e.g., diseases relevant to bacterial infections) refers to an amount sufficient to prevent, stop or retard the occurrence of diseases (e.g., diseases relevant to bacterial infections); effective amount for treatment of disease refers to an amount sufficient to cure or at least partially cure diseases and complications thereof in patients. Determination of such effective amounts pertains to the ability of those skilled in the art. For example, therapeutically effective amount depends on severity of disease to be treated, general state of immune system of patient, general conditions of patient such as age, body weight and gender, manner of administration of the drug, other treatments simultaneously applied, etc.

The present invention further relates to a pharmaceutical composition comprising the compound of Formula (I), a pharmaceutically acceptable salt, ester, solvate or stereoisomer thereof, and optionally one or more pharmaceutically acceptable carriers and/or diluents. The pharmaceutical composition can be formulated to any pharmaceutically acceptable dosage forms. For example, the compound or pharmaceutical composition of the present invention can be formulated to tablets, capsules, pills, granules, solutions, suspensions, syrups, injections (including injection solution, sterile powders for injection, and concentrated solutions for injection), suppositories, inhalants or sprays.

In addition, the pharmaceutical composition of the present invention can be delivered via any suitable manners, such as oral, parenteral, rectal, intrapulmonary or topical administration to a patient or subject in need of such treatment. For oral administration, the pharmaceutical composition can be an oral preparation, for example, oral solid preparations such as tablets, capsules, pills, granules, etc.; or oral liquid preparations such as oral solutions, oral suspensions, syrups and so on. When preparing oral preparations, the pharmaceutical composition may further comprise suitable fillers, binding agents, disintegrating agents, lubricating agents and so on. For parenteral administration, the pharmaceutical composition can be injections including injection solutions, sterile powders for injection and concentrated solutions for injection. When preparing injections, the pharmaceutical composition can be produced via a conventional method in current pharmaceutical industry. When preparing injections, to the pharmaceutical composition may not be added an additive, or may be added suitable additives according to properties of medicament. For rectal administration, the pharmaceutical composition can be suppositories. For intrapulmonary administration, the pharmaceutical composition can be inhalants or sprays. In some preferable embodiments, the compound of the present invention, a pharmaceutically acceptable salt, ester, solvate or stereoisomer thereof is present in the pharmaceutical composition or medicament in a therapeutically and/or prophylactically effective amount. In some preferable embodiments, the compound of the present invention, a pharmaceutically acceptable salt, ester, solvate or stereoisomer thereof is present in the pharmaceutical composition or medicament in unit dose.

The compound of the Formula (I) of the present invention, or its pharmaceutically acceptable salts, its esters, its solvates or its stereoisomers can be administrated alone, or administrated in combination with one or more second therapeutic agents. Thus, in some preferable embodiments, the pharmaceutical composition also contains one or more second therapeutic agents. In some preferable embodiments, the second therapeutic agents are selected from the group consisting of: anti-inflammatory agents, matrix metalloproteinase inhibitors, lipoxygenase inhibitors, cytokine antagonists, immunosuppressors, anticancer agents, antiviral agents, growth factor regulators, immunoregulators or compounds against excessive proliferation of blood vessels.

The ingredients to be combined (e.g., the compound of the present invention, its pharmaceutically acceptable salts, its esters, its solvates, its stereoisomers, and second therapeutic agents) can be administrated simultaneously or separately in order. For example, the second therapeutic agents can be administrated before, at the same time or after the administration of the compound of present invention, its pharmaceutically acceptable salts, its esters, its solvates or its stereoisomers. In addition, the ingredients to be combined can also be administrated in combination in form of same one dosage form or separate different preparations.

The compound of Formula (I) of the present invention, a pharmaceutically acceptable salt, ester, solvate or stereoisomer thereof can be used for treatment and/or prophylaxis of diseases relevant to bacterial infections. Thus, the present invention further relates to use of the compound of Formula (I) of the present invention, a pharmaceutically acceptable salt, ester, solvate or stereoisomer thereof in manufacture of a medicament, the medicament is used for treatment and/or prophylaxis of diseases relevant to bacterial infections in a subject. In addition, the present invention further relates to a method for inhibiting bacteria or for treatment and/or prophylaxis of diseases relevant to bacterial infections in a subject, which comprises administrating to the subject in such need with a therapeutically and/or prophylactically effective amount of the compound of Formula (I) of the present invention, a pharmaceutically acceptable salt, ester, solvate or stereoisomer thereof, or the pharmaceutical composition of the present invention.

In some preferable embodiments, the diseases are infectious diseases caused by bacteria, and the bacterium is selected from gram-positive bacterium or gram-negative bacterium, preferably gram-negative bacterium: the gram-positive bacterium is selected from one or more of *Staphylococcus aureus, Staphylococcus epidermidis, Streptococcus agalactiae, Enterococcus faecalis, Streptococcus pneumoniae, Streptococcus pyogenes, Enterococcus faecium*, or *Clostridium difficile*; and the gram-negative bacterium is selected from one or more of *Citrobacter, Citrobacter freundii, Enterobacter cloacae, Klebsiella pneumoniae, Escherichia coli, Proteus vulgaris, salmonella, Serratia marcescens, Shiga's bacillus, Pseudomonas aeruginosa, Mucositis mora* bacteria, *Neisseria gonorrhoeae, Neisseria meningitidis, Diplococcus gonorrhoeae, Acinetobacter* Species, *Burkholderia* Species, *Bacterium flexuosus, Helicobacter pylori, Bacillus comma, Klebsiella, Haemophilus influenzae, Mycobacterium avum* complex, *Mycobacterium abscessus, Mycoboterium kansasii, Mycobacterium ulcerans, Chlamydophila pneumoniae, Chlamydia trachomatis, Haemophilus influenzae, Streptococcus pyogenes, β-Streptococcus hemolyticus, Acinetobacter baumannii, Pseudomonas aeruginosa, Bacteroides fragilis, Bacillus cereus* or *Stenotrophomonas maltophilia*.

In some preferable embodiments, the infectious diseases caused by the bacteria are selected from one or more: upper respiratory tract infection, lower respiratory tract infection, complicated urinary tract infection and other urinary tract infection, central nervous system infection, ear infection, infections of pleura, lung and bronchia, pulmonary tuberculosis, co-occurring or non-co-occurring urinary tract infection, intra-abdominal infection, cardiovascular infection, bloodstream infection, septicemia, bacteremia CNS infection, skin or soft-tissue infection, GI infection, bone and joint infection, genital infection, eye infection, granuloma infection, co-occurring or non-co-occurring skin and skin structure infections, catheter-related infection, pharyngitis, sinusitis, otitis extern, otitis media, bronchitis, empyema, pneumonia, community-acquired bacterial pneumonia, hospital acquired pneumonia, hospital acquired bacterial pneumonia, ventilator-associated pneumonia, diabetic foot infection, vancomycin-resistant enterococcus infection, urocystitis and nephropyelitis, renal calculus, prostatitis, peritonitis, complicated intra-abdominal infections and other intra-abdominal infections, dialysis-associated peritonitis, viscera, endocarditis, myocarditis, pericarditis, infusion-related septicemia, meningitis, cerebritis, brain abscess, osteomyelitis, arthritis, genital ulcer, urethritis, vaginitis, cervicitis, gingivitis, conjunctivitis, keratitis, entophthalmia, infections in cystic fibrosis patients or infections in febrile neutropenia patients.

Beneficial Effects of the Invention

In comparison with the prior art, the technical solutions of the present invention have the following merits:

(1) The compound of Formula (I) of the present invention, a pharmaceutically acceptable salt, ester, solvate or stereoisomer thereof have excellent β-lactamase inhibitor activity, showing excellent effect on combating β-lactamase.

(2) The compound of Formula (I) of the present invention, a pharmaceutically acceptable salt, ester, solvate or stereoisomer thereof have higher activity (i.e., lower $IC_{50}$) in inhibition of type C β-lactamases of *Pseudomonas pyocyaneum* or *Enterobacter cloacae*, type A and type D β-lactamases of *Klebsiella*.

(3) The compound of Formula (I) of the present invention, a pharmaceutically acceptable salt, ester, solvate or stereoisomer thereof have effective activity of inhibiting type B metal β-lactamases, which enable the compound of the present invention to be used for treatment of drug-resistant bacteria infections caused by a variety of β-lactamases, especially drug-resistant diseases caused by bacteria having type B metallo-β-lactamases (e.g., *Bacteroides fragilis* (CcrA), *Klebsiella pneumoniae, Escherichia coli* or *Enterobacter cloacae, Citrobacter freundii, Bacillus cereus* (Bc II) or *Stenotrophomonas maltophilia* (L1)), and to reduce longer main retention time, higher mortality rate and increased therapeutic cost of infections caused by drug-resistant bacteria.

(4) The compound of Formula (I) of the present invention, a pharmaceutically acceptable salt, ester, solvate or stereoisomer thereof has a longer half-life period and a lower clearance rate as viewed from pharmacokinetics properties, and is broader-spectrum β-lactamase inhibitor so that it can be used to treat drug-resistant bacterial infections caused by β-lactamase.

(5) The compound of Formula (I) of the present invention, a pharmaceutically acceptable salt, ester, solvate or stereoisomer thereof are featured in simple production process, stable quality, good physical and chemical properties, and easy for industrial production in large scale.

Embodiments of the Invention

The present invention is further illustrated with the following embodiments, but these are not intended to limit the present invention. According to the teaching of the present invention, those skilled in the art can make various modifications or changes without departing from the basic spirits and scope of the present invention.

Experimental Protocols

Exemplifying experimental schemes for some compounds of the present invention are provided as follows to illustrate the advantageous activity and beneficial technical effects of the compound of the present invention. It should be understood that the following experimental schemes are merely to exemplify the contents of the present invention, and are not intended to limit the scope of the present invention. It will be apparent to those skilled in the art that the technical solutions of the present invention may be modified or changed under the teachings of the present invention and without departing from the spirit and scope of the invention.

Experimental Example 1: Pharmacokinetics Experiments of the Compound of the Present Invention in Rats Test samples: some compounds of the present invention, which chemical names and preparation methods are shown in preparation examples of compounds.

Control drugs: Avibactam sodium salt, purchased from Jinan Xinzheng Pharmaceutical Science and Technology Co., Ltd.; MK-7655, self-made, referring to preparation method of WO2009091856A2 (published on Jul. 23, 2009).

Internal standard substance: MK-7655, dissolved in acetonitrile to form an internal standard solution containing MK-7655 (25 ng/mL): Furosemide, dissolved in acetonitrile to form an internal standard solution containing Furosemide (25 ng/mL).

Test animals: 3 male SD rats, bodyweight 200-250 g for each animal.

Preparation of Solutions of Test Samples:

(1) Method for preparing solution of test sample of Avibactam:

Sodium salt of Avibactam compound (2.02 mg) was weighed, added to DMSO (196 μL), heated and dissolved under ultrasonic, then to which was added HP-β-CD (40%, 783 μL), mixed homogeneously with vortex, kept the mixture in a 50° C. constant temperature water bath for 20 min. then sterile water for injection (2.936 mL) was added, mixed homogeneously with vortex, filtered with membrane to obtain a solution with concentration of 0.5 mg/mL.

(2) Method for preparing solution of test sample of control drug MK-7655:

MK-7655 compound (2.20 mg) was weighed, added to DMSO (209 μL), heated and dissolved under ultrasonic, then to which was added HP-1-CD (40%, 836 μL), mixed homogeneously with vortex, kept the mixture in a 50° C. constant temperature water bath for 20 min, then sterile water for injection (3.135 mL) was added, mixed homogeneously with vortex, filtered with membrane to obtain a solution with concentration of 0.5 mg/mL.

(3) Method for preparing solution of test sample of Compound 1:

Compound 1 (2.03 mg) was weighed, added to DMSO (186 μL), heated and dissolved under ultrasonic, then to which was added HP-f-CD (40%, 744 μL), mixed homogeneously with vortex, kept the mixture in a 50° C. constant temperature water bath for 20 min, then sterile water for injection (2.789 mL) was added, mixed homogeneously with vortex, filtered with membrane to obtain a solution with concentration of 0.5 mg/mL.

(4) Method for preparing solution of test sample of Compound 2:

Compound 2 (1.47 mg) was weighed, added to DMSO (132 μL), heated and dissolved under ultrasonic, then to which was added HP-β-CD (40%, 526 μL), mixed homogeneously with vortex, kept the mixture in a 50° C. constant temperature water bath for 20 min, then sterile water for injection (1.973 mL) was added, mixed homogeneously with vortex, filtered with membrane to obtain a solution with concentration of 0.5 mg/mL.

(5) Method for preparing solution of test sample of Compound 4:

Compound 4 (1.71 mg) was weighed, added to DMSO (152 μL), heated and dissolved under ultrasonic, then to which was added HP-β-CD (40%, 609 μL), mixed homogeneously with vortex, kept the mixture in a 50° C. constant temperature water bath for 20 min, then sterile water for injection (2.283 mL) was added, mixed homogeneously with vortex, filtered with membrane to obtain a solution with concentration of 0.5 mg/mL.

(6) Method for preparing solution of test sample of sodium salt of Compound 6:

Sodium salt of Compound 6 (1.5 mg) was weighed, added to 5% glucose injection solution (2.56 mL) and dissolved under vortex and ultrasound, after passing membrane and sampling, the solution with a concentration of 0.5 mg/mL was obtained.

Experimental Methods

Administration:

Test samples were administrated via intravenous push (iv), dosage of administration was 1 mg/kg, volume of administration was 2 mL/kg.

Blood Sampling:

Collecting time points: iv: after administration 0.083 h, 0.25 h, 0.5 h, 1 h, 2 h, 4 h, 6 h, 8 h, 24 h.

At each time point, about 100 μL of whole blood was sampled via caudal vein, added to $K_2EDTA$ anti-coagulative tube, centrifuged in a refrigerated centrifuge under 8000 rpm for 6 min to separate plasma, and the plasma was stored in −80° C. refrigerator.

Analysis of Plasma Samples (Using Precipitation of Protein):

(1) Analysis method for Compound 1, Compound 4, control drugs of Avibactam (AVI) sodium salt and MK-7655:

Plasma (20 μL) was taken and placed in a 96-well deep-well plate, and internal standard solution (300 μL) was added, subjected to vortex for 5 min, then centrifuged under 12000 rpm for 5 min, and then supernatant (200 μL) was taken and subjected to vortex for 3 min; to be analyzed by LC-MS/MS.

(2) Analysis method for Compound 2:

Plasma (30 μL) was taken and placed in 1.5 mL EP tube, and internal standard solution (300 μL) was added, subjected to vortex for 5 min, then centrifuged under 12000 rpm for 5 min, and then supernatant (200 μL) was taken and subjected to vortex for 3 min; to be analyzed by LC-MS/MS.

(3) Analysis method for sodium salt of Compound 6:

Plasma (30 μL) was taken and placed in a 96-well deep-well plate, and internal standard solution (200 μL) was added, subjected to vortex for 5 min, then centrifuged under 4000 rpm for 20 min, and then supernatant (100 μL) was taken and water (100 μL) was added, and subjected to vortex homogeneously; to be analyzed by LC-MS/MS.

Experimental Results:

TABLE 1

Results of PK evaluation of the compounds of the present invention in SD rat (iv: 1 mg/kg)

| Test sample | $T_{1/2}$ (h) | $AUC_{last}$ (h*ng/mL) | $Cl\_{obs}$ (mL/h/kg) | $Vss\_{obs}$ (mL/kg) |
|---|---|---|---|---|
| Compound 1 | 1.01 | 2327 | 466 | 294 |
| Compound 2 | 0.74 | 2504 | 400 | 261 |
| Compound 4 | 2.04 | 1391 | 724 | 348 |
| Compound 6 sodium salt | 0.25 | 1841 | 545 | 219 |
| AVI sodium salt | 0.41 | 1140 | 894 | 535 |
| MK-7655 | 0.39 | 1023 | 1002 | 409 | wherein, $T_{1/2}$ was half-life period; $AUC_{last}$ was area under the curve 0→t; CL was clearance rate; Vss was apparent volume of distribution.

Experimental Conclusion:

It could be seen in the experimental results of Table 1 that the compounds of the present invention had longer half-life period, lower clearance rate, higher exposure dose in comparison with the two control drugs, Avibactam (AVI) sodium salt and MK-7655, so that the compound of the present invention had good pharmacokinetics properties.

Experimental Example 2: In Vitro Antibacterial Activity of the Compounds of the Present Invention Experimental strains: all experimental standard bacterial strains for enzyme production were purchased from ATCC, and the clinically separated CRE strain was purchased from Southwest Hospital of the Third Military Medical University.

Test samples: some of the compounds of the present invention, which chemical names and preparation methods were shown in the preparation examples of compounds.

Control Drugs: Avibactam (AVI) sodium salt, MK-7655 were self-made by Shandong Xuanzhuo Pharma Co., Ltd., which structure formulas were shown in the section of Background Art.

Experimental Method: Agar dilution method, referring to M100-S23: Performance Standards for Antimicrobial Susceptibility Testing: Twenty-Third Informational Supplement (Clinical And Laboratory Standards Institute, 2013). Minimal inhibitory concentration (MIC, μg/mL) was calculated.

Experimental Results:

TABLE 2

In vitro antibacterial activities of the compounds of the present invention on standard bacterial strains for enzyme production from ATCC (μg/mL)

| Strain No. | Strain Name | Enzyme production information | AVI sodium salt | MK-7655 | Comp. 2 | Comp. 6 | Comp. 7 sodium salt | Comp. 13 | Comp. 14 |
|---|---|---|---|---|---|---|---|---|---|
| BAA-1900 ™ | Klebsiella pneumoniae | KPC | >8 | >16 | 1 | 2 | 8 | 8 | 4 |
| BAA-2146 ™ | Klebsiella pneumoniae | NDM-1 | >8 | >16 | 2 | 4 | / | / | 8 |
| BAA-2524 ™ | Klebsiella pneumoniae | OXA-48 | >8 | >16 | 2 | 2 | 8 | 4 | 4 |
| BAA-2340 ™ | Escherichia coli | KPC | 8 | >16 | 0.5 | / | / | / | / |
| BAA-2452 ™ | Escherichia coli | NDM-1 | >8 | >16 | 1 | 2 | 4 | 4 | 2 |
| BAA-2523 ™ | Escherichia coli | OXA-48 | 8 | >16 | 1 | 1 | 4 | 4 | 2 |
| BAA-196 ™ | Escherichia coli | TEM-10 | >8 | >16 | 1 | / | 8 | 16 | 8 |
| BAA-2341 ™ | Enterobacter cloacae | KPC | >8 | >16 | 2 | 2 | 8 | / | 8 |
| BAA-2082 ™ | Enterobacter hormaechei | KPC | >8 | >16 | 2 | 2 | 8 | 16 | 8 |
| ATCC-51983 ™ | Klebsiella oxytoca | SHV-5 | >8 | >16 | 2 | 4 | / | 8 | 8 |

Slash "/" means: not determined.

TABLE 3

In vitro antibacterial activities of the compounds of the present invention on clinically separated CRE strains (μg/mL)

| Strain No. | Strain Name | Enzyme production information | AVI sodium salt | MK-7655 | Comp. 2 | Comp. 6 |
|---|---|---|---|---|---|---|
| 7450kpn-597 | Klebsiella pneumoniae | KPC, ESBLs | >8 | >8 | 2 | 2 |
| 7526kpn-640 | Klebsiella pneumoniae | KPC, ESBLs | >8 | >8 | 4 | / |
| 7460kpn-607 | Klebsiella pneumoniae | NDM, ESBLs | >8 | >8 | 2 | / |
| 7477kpn-624 | Klebsiella pneumoniae | NDM, ESBLs | >8 | >8 | 2 | / |
| 7484kpn-631 | Klebsiella pneumoniae | IMP, ESBLs | >8 | >8 | 2 | 4 |
| 7463kpn-610 | Klebsiella pneumoniae | ESBLs | 8 | >8 | 2 | 2 |
| 7438eco-639 | Escherichia coli | NDM, ESBLs | 8 | >8 | 2 | 2 |
| 7440eco-641 | Escherichia coil | ESBLs | 8 | >8 | 2 | / |
| 7494ecl-295 | Enterobacter cloacae | NDM, ESBLs, AmpC | >8 | >8 | 2 | 2 |
| 7511ecl-312 | Enterobacter cloacae | NDM, ESBLs, AmpC | >8 | >8 | 2 | / |
| 7495ecl-296 | Enterobacter cloacae | IMP, ESBLs, AmpC | >8 | >8 | 2 | 2 |
| 7498ecl-299 | Enterobacter cloacae | ESBLs, AmpC | >8 | >8 | 2 | 2 |
| 7513ecl-314 | Enterobacter cloacae | AmpC | >8 | >8 | 2 | 2 |
| 7520cfr-167 | Citrobacter freundii | NDM, OXA-10, ESBLs | >8 | >8 | 2 | 2 |
| 7521cfr-169 | Citrobacter freundii | NDM, ESBLs, AmpC | 8 | >8 | 2 | 2 |

Note:
ESBLs represents "extended-spectrum β-lactamases";
slash "/" means "not determined"

TABLE 4

In vitro antibacterial activities of the compounds of the present invention on strains for enzyme production (μg/mL)

| Strain No. | Strain Name | Enzyme production information | AVI sodium salt | Comp. 2-2 | Comp. 6-2 |
|---|---|---|---|---|---|
| BAA-1900 ™ | Klebsiella pneumoniae | KPC | 16 | 4 | 8 |
| BAA-2146 ™ | Klebsiella pneumoniae | NDM-1 | 8 | 2 | 16 |
| BAA-2452 ™ | Escherichia coli | NDM-1 | 16 | 4 | 8 |
| BAA-2523 ™ | Escherichia coli | OXA-48 | 16 | 4 | 8 |
| BAA-196 ™ | Escherichia coli | TEM-10 | 16 | 4 | 8 |
| 7484kpn-631 | Klebsiella pneumoniae | IMP, ESBLs | 16 | 2 | 4 |
| 7463kpn-610 | Klebsiella pneumoniae | ESBLs | 32 | 2 | 8 |
| 7513ecl-314 | Enterobacter cloacae | AmpC | 32 | 2 | 4 |

Experimental Conclusions:

According to the experimental results of Tables 2, 3 and 4, it could be determined that the compounds of the present invention had remarkably advantageous inhibition effect against antibiotic-resistant bacteria caused by β-Lactamase, especially for antibiotic-resistant bacteria caused by type B of β-Lactamase compared to the control drugs Avibactam (AVI) sodium salt or MK-7655. The compounds of the present invention had antibacterial activities to the experimental strains above, which indicated that the compounds of the present invention had good potency in clinical applications.

Experimental Example 3: In Vitro Tests of Enzymatic Activity of the Compounds of the Present Invention Test samples: some of the compounds of the present invention, which chemical names and preparation methods were shown in the preparation examples of the compounds.

Control Drugs: Avibactam (AVI) sodium salt, MK-7655 self-made by Shandong Xuanzhuo Pharma Co., Ltd., which structure formulas were shown in the section of Background Art.

Experimental Methods:

Nitrocefin, a kind of cephalosporin antibiotics, is sensitive to most of β-lactamases, and changes in color after being hydrolyzed. The hydrolysis rate of Nitrocefin was measured by real-time recording corresponding absorbance of reaction system. β-Lactamase inhibitors could inhibit hydrolysis of the enzymes to Nitrocefin, and reduce hydrolysis rate. By measuring reaction rates in the same reaction system under different inhibitor concentrations, the $IC_{50}$ (half maximal inhibitory concentration) values of inhibitors were calculated.

1. Preparation of Reagents

Nitrocefin was dissolved in DMSO to form a solution with concentration of 2 mM, which was sub-packaged and stored at −20° C. The concentration of purchased β-lactamases mother liquor was 1 mg/mL, and the mother liquor was dissolved in 50% glycerol. A part of mother liquor was taken and diluted by 1000 times in reaction solution, sub-packaged and stored at ~20° C.

2. Preparation of Compound Solutions

The compounds to be tested were dissolved in DMSO to form a mother liquor with concentration of 10 mM. If not used that day, the mother liquor was stored at −20° C. Its test final concentrations were: 100 μM, 25 μM, 6.25 μM, 1.563 μM, 390.6 nM, 97.66 nM, 24.41 nM, 6.10 nM, 1.53 nM, 0.381 nM, 0.095 nM. EDTA-Na2 was used as control for NDM-1 test and had an initial final concentration of 20 mM.

3. Reaction System

| Type | β-lactamases | Final concentration of enzyme (nM) | Substrate (Nitrocefin) final concentration (mM) | Reaction buffer solution |
|---|---|---|---|---|
| Ex. 1 | TEM-1 | 0.25 | 0.1 | 1 × PBS, pH 7.4, 0.1 mg/mL BSA |
| | KPC-2 | 320 | 0.1 | 1 × PBS, pH 7.4, 0.1 mg/mL BSA |
| | AmpC | 0.4 | 0.1 | 1 × PBS, pH 7.4, 0.1 mg/mL BSA |
| | NDM-1 | 4 | 0.1 | 50 mM Hepes, 100 μM $ZnCl_2$ |
| Ex. 2 | TEM-1 | 1 | 0.1 | 1 × PBS, pH 7.4, 0.1 mg/mL BSA |
| | KPC-2 | 1.28 | 0.1 | 1 × PBS, pH 7.4, 0.1 mg/mL BSA |
| | AmpC | 1.6 | 0.1 | 1 × PBS, pH 7.4, 0 1 mg/mL BSA |
| | CTX-M-1 | 0.2 | 0.1 | 1 × PBS, pH 7.4, 0.1 mg/mL BSA |
| Ex. 3 | OXA-10 | 10 | 0.1 | 1 × PBS, pH 7.4, 0.1 mg/ml BSA |

Results of Experiment 1:

TABLE 4

Inhibition activities of the compounds of the present invention to β-lactamases ($IC_{50}$)

| Compound | ESBLs type TEM-1 (nM) | Type A KPC-2 (nM) | Type C AmpC (nM) |
|---|---|---|---|
| AVI sodium salt | 57.43 | 67.69 | 100.9 |
| MK-7655 | 281.8 | 119.9 | 49.53 |
| Compound 1 | 28.2 | 81.7 | 22.9 |
| Compound 2 | 28.5 | 61.1 | 32.6 |
| Compound 4 | 20.5 | 23.1 | / |
| Compound 5 | 66.5 | 27.4 | 84.1 |

Slash "/"means: not determined.

Results of Experiment 2:

TABLE 5

Inhibition activities of the compounds of the present invention to β-lactamases ($IC_{50}$, nM)

| Compound | Type A KPC-2 | ESBLs type TEM-1 | ESBLs type CTX-M-1 | Type C AmpC |
|---|---|---|---|---|
| Compound 2 | 34.69 | 15.19 | 42.27 | 17.42 |
| Compound 6 | 42.3 | 30.13 | 40.78 | 17.74 |

Results of Experiment 3:

TABLE 6

Inhibition activities of the compounds of the present invention to β-lactamases ($IC_{50}$)

| Compound | Type D OXA-10 ($IC_{50}$, μM) |
|---|---|
| AVI sodium salt | 25.93 |
| Compound 2 | 12.21 |
| Sodium salt of Compound 6 | 21.68 |

Experimental Conclusions:

According to the table above, it could be determined that the compounds of the present invention had good inhibition effects on Beta-Lactamases, which were superior to or equivalent to the inhibition activity of control drugs Avibactam (AVI) sodium salt or MK-7655.

4. Examples

The above contents of the present invention are further illustrated in details by specific embodiments in the following examples. However, it should be understood that the protection scope of the present invention should not be limited to the following examples. All technical solutions based on the foregoing contents of the present invention fall into the scope of the present invention.

The meanings of abbreviations used in the following examples are shown as follows:
Pd/C: palladium on carbon
DCM: dichloromethane
THF: tetrahydrofuran
DMSO: dimethylsulfoxide
LC-MS: liquid chromatography-mass spectrometry Preparation Example 1: Preparation of (2S,5R)-6-(benzyloxy)-7-oxo-1,6-diazabicyclo[3.2.1]octane-2-carboxylic acid

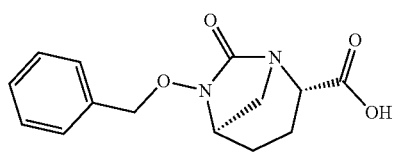 [SMILES: O=C(O)[C@@H]1CC[C@@H]2CN1C(=O)N2OCc1ccccc1]

(1) Preparation of ethyl (S)-2-((tert-butoxycarbonyl)amino)-6-(dimethyl(oxo)-λ⁶-sulfanylidene)-5-oxohexanoate

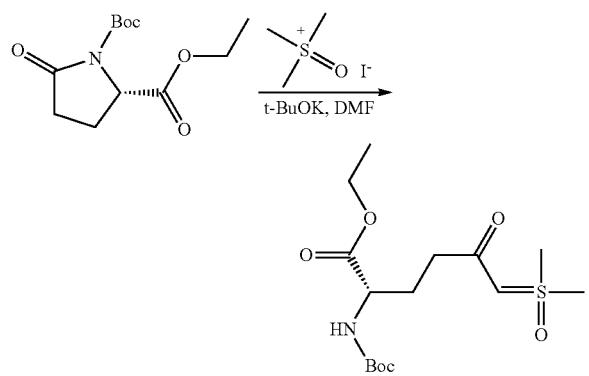

Trimethylsulfoxide iodide (343.2 g, 1.56 mol) was dissolved in N,N-dimethylformamide (2300 mL), and potassium tert-butoxide (156.9 g, 1.40 mol) was added in batches. The reaction solution was stirred at room temperature for 1 h, 1-(Tert-butyl) 2-ethyl (S)-5-oxopyrrolidine-1,2-dicarboxylate (350 g, 1.36 mol) was added in batches, then stirred at room temperature for 2 h, water (4000 mL) was added for quenching, extraction was performed using ethyl acetate (3000 mL×5), the organic phases were combined, washed with saturated brine (3000 mL), dried over anhydrous sodium sulfate, concentrated, the crude product was purified with silica gel chromatography (dichloromethane:methanol=10:1) to obtain the title compound as a pale yellow oil (280 g, yield 59%).

(2) Preparation of (S)-1-(tert-butyl) 2-ethyl 5-oxopiperidine-1,2-dicarboxylate

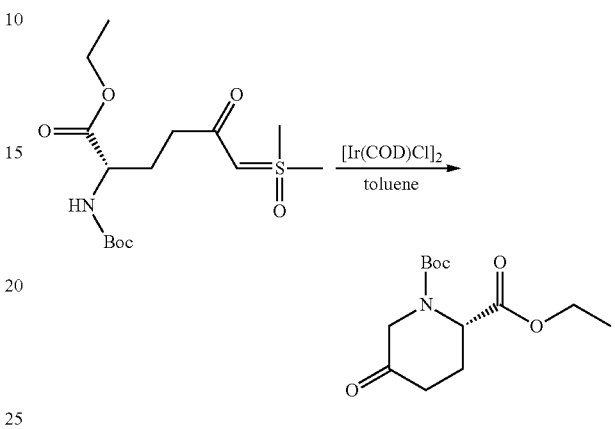

Ethyl (S)-2-((tert-butoxycarbonyl)amino)-6-(dimethyl(oxo)-λ⁶-sulfanylidene)-5-oxohexanoate (280 g, 801.28 mmol) was dissolved in toluene (8000 mL), 1,5-cyclooctadiene iridium chloride dimer (4.1 g, 7.95 mmol) was added. The reaction solution was reacted at 80° C. overnight under nitrogen gas protection. After vacuum concentration, the crude product was purified with silica gel chromatography (ethyl acetate:petroleum ether=1:5 to 1:3) to obtain the title compound as a pale yellow oil (132 g, yield 61%).

(3) Preparation of (2S,5S)-1-(tert-butyl) 2-ethyl 5-hydroxylpiperidine-1,2-dicarboxylate

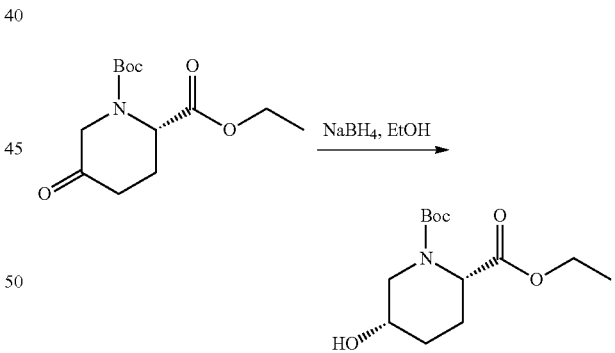

(S)-1-(tert-butyl) 2-ethyl 5-oxopiperidine-1,2-dicarboxylate (132 g, 486.53 mmol) was dissolved in ethanol (1500 mL), to which at 0° C. sodium borohydride (20.4 g, 539.25 mmol) was added in batches, then reacted at 0° C. for 20 min. The saturated aqueous solution (200 mL) of ammonium chloride was added for quenching, the resultant solution was diluted by adding water (3000 mL), extracted with ethyl acetate (1000 mL×3), and then the organic phases were combined, washed with saturated brine (1000 mL), dried over anhydrous sodium sulfate, concentrated, and the crude product was purified with silica gel chromatography (ethyl acetate:petroleum ether=1:3) to obtain the title compound as a colorless oil (130 g, yield 98%).

(4) Preparation of (2S,5R)-1-(tert-butyl) 2-ethyl 5-(N-(benzyloxy)-2-nitrophenylsulfonamido)piperidine-1,2-dicarboxylate

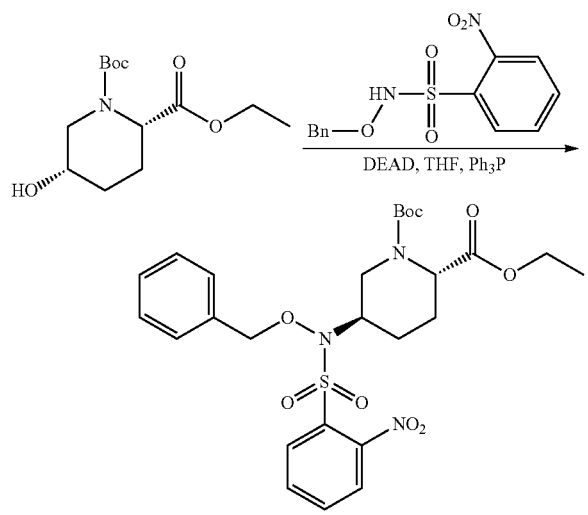

(2S,5S)-1-(tert-butyl) 2-ethyl 5-hydroxylpiperidine-1,2-dicarboxylate (130 g, 475.62 mmol), triphenylphosphine (212 g, 809.16 mmol) and N-(benzyloxy)-2-nitrophenyl-1-sulfamide (161.4 g, 523.5 mmol) were dissolved in tetrahydrofuran (1500 mL), cooled to 0° C., diethyl azodicarboxylate (149.1 g, 856.16 mmol) was added dropwise under nitrogen gas protection, after adding, the reaction solution was heated to room temperature and stirred overnight, concentrated, and the crude product was purified by silica gel chromatograph (ethyl acetate:petroleum ether=1:5) to obtain the title compound as a yellow oil (210 g, yield 78%).

(5) Preparation of (2S,5S) 1 (tert butyl) (2S,5R)-1-(tert-butyl) 2-ethyl 5-((benzyloxy)amino)piperidine-1,2-dicarboxylate

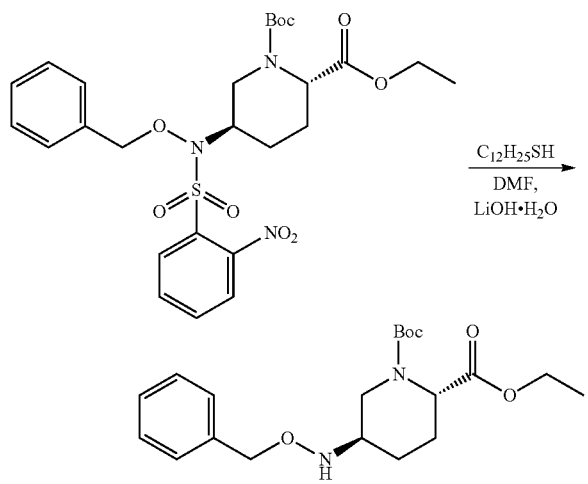

(2S,5R)-1-(tert-butyl) 2-ethyl 5-(N-(benzyloxy)-2-nitrophenylsulfonamido)piperidine-1,2-dicarboxylate (210 g, 372.59 mol) was dissolved in N,N-dimethylformamide (2000 mL), to which lithium hydroxide monohydrate (31.1 g, 741.11 mmol) and n-dodecanethiol (149.5 g, 738.63 mmol) were added, reacted at room temperature overnight. Water (4000 mL) was added, extracted with ethyl acetate (1000 mL×3), the organic phases were combined, washed with saturated brine (1000 mL), dried over anhydrous sodium sulfate, concentrated, and the crude product was purified by silica gel chromatography (ethyl acetate: petroleum ether=1:5) to obtain the title compound as yellow oil (90 g, yield 64%).

(6) Preparation of (2S,5R)-ethyl 5-((benzyloxy)amino)piperidine-2-carboxylate

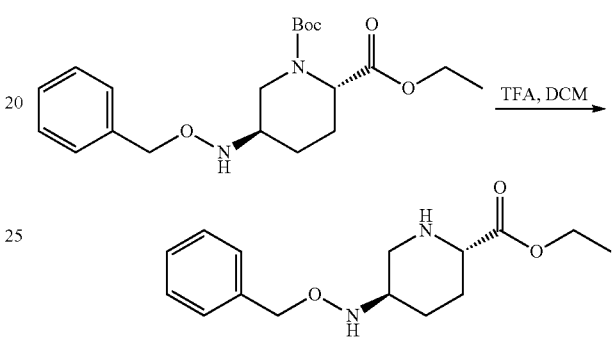

(2S,5R)-1-(tert-butyl) 2-ethyl 5-((benzyloxy)amino)piperidine-1,2-dicarboxylate (90 g, 237.8 mmol) was dissolved in dichloromethane (700 mL), cooled to 0° C., trifluoroacetic acid (200 mL) was added dropwise. After addition, the reaction was performed at room temperature overnight, and saturated sodium dicarbonate solution was used to regulate pH as 10, the phases were separated. The aqueous phase was extracted with dichloromethane (300 mL×3), and the organic phases were combined, washed with saturated brine (200 mL), dried over anhydrous sodium sulfate, concentrated. The crude product was purified by silica gel chromatography (dichloromethane:methanol=20:1) to obtain the title compound as pale yellow oil (70 g of crude product).

(7) Preparation of (2S,5R)-ethyl 6-(benzyloxy)-7-oxo-1,6-diazabicyclo[3.2.1]octane-2-carboxylate

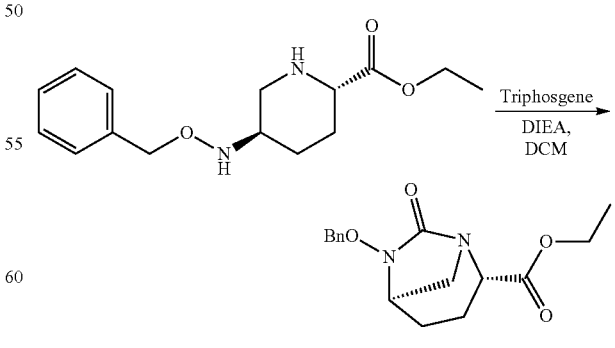

(2S,5R)-ethyl 5-((benzyloxy)amino)piperidine-2-carboxylate (70 g, 251.48 mmol) and N,N-diisopropyl ethyl amine (129 g, 1000 mmol) were dissolved in dichloromethane (1400 mL), cooled to 0° C., triphosgene (29.4 g, 99 mmol) was added in batches, heated to room temperature after addition and stirred overnight. The resultant solution was washed in sequence with 10% phosphoric acid solution (400 mL×2), a saturated solution (400 mL×2) of sodium decarbonate and saturated brine (400 mL×2), dried over anhydrous sodium sulfate, concentrated, and the crude product was purified by silica gel chromatography (ethyl acetate: petroleum ether=1:5 to 1:2) to obtain the title compound as a white solid (40.8 g, yield 50%).

(8) Preparation of (2S,5R)-6-(benzyloxy)-7-oxo-7-oxo-1,6-diazabicyclo[3.2.1]octane-2-carboxylic acid

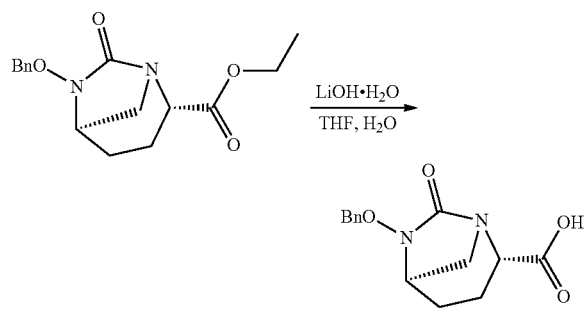

(2S,5R)-ethyl6-(benzyloxy)-7-oxo-1,6-diazabicyclo [3.2.1]octane-2-carboxylate (40.8 g, 134.06 mmol) was dissolved in tetrahydrofuran (900 mL), a solution of lithium hydroxide monohydrate (5.5 g, 131.08 mmol) in water (300 mL) was added dropwise. After addition, the reaction was performed at room temperature overnight. Water (200 mL) was added, ethyl acetate (500 mL×2) was used for extraction, the aqueous phase was collected, regulated with 1 mol/L hydrochloric acid to pH=3, extracted with dichloromethane (200 mL×3), the organic phases were combined, dried over anhydrous sodium sulfate, concentrated to obtain the title compound as a white solid (25 g, yield 67%).

Molecular Formula: $C_{13}H_{20}N_4O_6S$ Molecular Weight: 276.29 LC-MS (m/z): 277[M+H]$^+$ $^1$H-NMR (300 MHz, CDCl$_3$) δ: 7.55-7.35 (m, 5H), 5.08 (d, J=11.1 Hz, 1H), 4.91 (d, J=11.4 Hz, 1H), 4.14 (m, 1H), 3.35 (m, 1H), 3.11 (m, 1H), 2.90 (m, 1H), 2.28-1.98 (m, 3H), 1.75-1.56 (m, 1H).

Preparation Example 2: Preparation of tert-butyl 6-hydroxyl-2-azaspiro[33]heptane-2-carboxylate

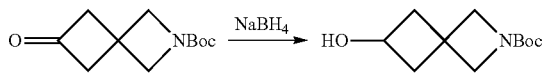 [SMILES: CC(C)(C)OC(=O)N1CC2(CC(=O)C2)C1 ; "NaBH4" ; CC(C)(C)OC(=O)N1CC2(CC(O)C2)C1]

Tert-butyl 6-oxo-2-azaspiro[3.3]heptane-2-carboxylate (4.22 g, 20 mmol) was added in methanol (30 mL), cooled under nitrogen gas protection to 0° C., and sodium borohydride (1.52 g, 40 mmol) was added. After addition, the reaction solution was heated to 25° C. and stirred for 1 h, after completing reaction as measured by LC-MS, water (1 mL) was added to quench reaction, solvent was removed by vacuum distillation, water (100 mL) and ethyl acetate (100 mL) were added, the phases were separated, the organic phase was washed with hydrochloric acid (1 mol/L, 50 mL), dried over anhydrous sodium sulfate, filtered, the filtrate was concentrated to obtain the title compound in white color (4.0 g, yield 93.7%).

Preparation Example 3: Preparation of tert-butyl 6-(1,3-dioxoisoindolin-2-yl)-2-azaspiro[3.3]heptane-2-carboxylate

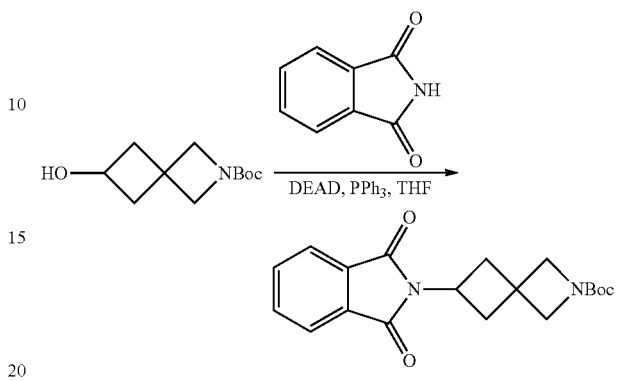

Under nitrogen gas protection, tert-butyl 6-hydroxyl-2-azaspiro[3.3]heptane-2-carboxylate (4.0 g, 18.8 mmol), phthalimide (3.86 g, 26.2 mmol) and triphenylphosphine (5.92 g, 22.6 mmol) were added to tetrahydrofuran (100 mL), cooled to 0° C., diethyl azodicarboxylate (3.93 g, 22.6 mmol) was slowly added dropwise. After addition, the reaction solution was heated to 25° C. and stirred for 16 h. After complete reaction as measured by LC-MS, water (1 mL) was added to quench the reaction, concentration was performed by removing solvent under reduced pressure, water (150 mL) and ethyl acetate (150 mL) were added, the phases were separated, the aqueous phase was extracted with ethyl acetate (100 mL×2), and the organic phases were combined, concentrated. The crude product was purified by silica gel chromatography (petroleum ether:ethyl acetate=10:1) to obtain the title compound in white color (6.0 g, yield 93.3%).

Preparation Example 4: Preparation of tert-butyl 6-amino-2-azaspiro[3.3]heptane-2-carboxylate

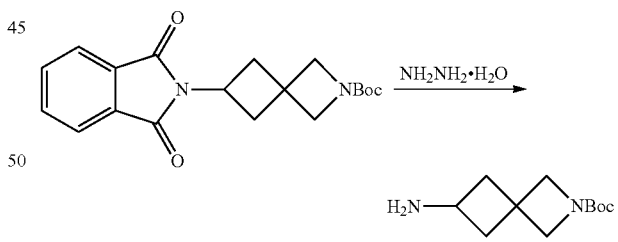

Tert-butyl 6-(1,3-dioxoisoindol-2-yl)-2-azaspiro[3.3]heptane-2-carboxylate (6.0 g, 17.5 mmol) was dissolved in ethanol (160 mL), hydrazine hydrate (16 mL) was added under stirring. The stirring was kept at 25° C. for 1.5 h and a large amount of white precipitates occurred in the reaction solution. After the reaction was completed as measured by LC-MS, filtration was performed, the filtrate was concentrated, ether (200 mL) was added, shaken under ultrasonic, filtration was performed, the filtrate was concentrated, the crude product was purified by silica gel column chromatography (dichloromethane:methanol=50:1, 0.1% aqueous ammonia added) to obtain the title compound in white color (2.9 g, yield 78.2%).

Preparation Example 5: Preparation of tert-butyl 6-((2S,5R)-6-(benzyloxy)-7-oxo-1,6-diazabicyclo[3.2.1]octane-2-carboxamido)-2-azaspiro[3.3]heptane-2-carboxylate

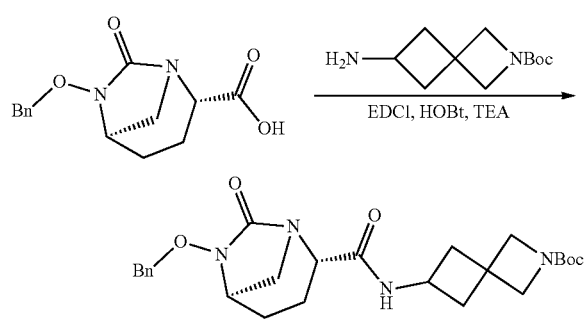

(2S,5R)-6-(benzyloxy)-7-oxo-1,6-diazabicyclo[3.2.1]octane-2-carboxylic acid (3.77 g, 13.6 mmol) and tert-butyl 6-amino-2-azaspiro[3.3]heptane-2-carboxylate (2.9 g, 13.7 mmol) was dissolved in dichloromethane (100 mL), cooled to 0° C. under protection of nitrogen gas, to which 1-hydroxylbenzotriazole (2.76 g, 20.4 mmol), triethylamine (3.16 g, 31.3 mmol) and 1-ethyl-(3-dimethylaminopropyl)carbodiimide hydrochloride (3.91 g, 20.4 mmol) were added, and the reaction solution was heated to 25° C. and stirred for 16 h. After completion of the reaction as measured by LC-MS, water (100 mL) and dichloromethane (100 mL) were added, after the phases were separated, the organic phase was concentrate, the crude product was purified by silica gel column chromatography (petroleum ether:ethyl acetate=4:1 to 1:1) to obtain the title compound (4.5 g, yield 70.3%).

Preparation Example 6: Preparation (2S,5R)-6-(benzyloxy)-7-oxo-N-(2-azaspiro[3.3]heptan-6-yl)-1,6-diazabicyclo[3.2.1]octane-2-carboxamide

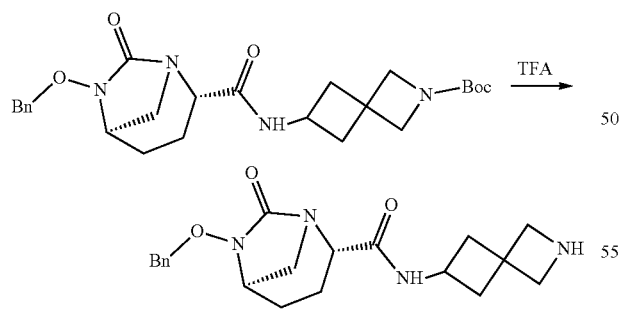

Tert-butyl 6-((2S,5R)-6-(benzyloxy)-7-oxo-1,6-diazabicyclo[3.2.1]octane-2-formamido)-2-azaspiro[3.3]heptane-2-carboxylate (1.1 g, 2.34 mmol) was dissolved in dichloromethane (15 mL), trifluoroacetic acid (5 mL) was added at 25° C., stirred and reacted for 1.0 h. After completion of the reaction as measured by LC-MS, concentration was performed under a reduced pressure, and the resultant product was directly used in the next reaction step.

Example 1: Preparation of (2S,5R)-2-(7-azaspiro[3.5]nonan-2-ylcarbamoyl)-7-oxo-1,6-diazabicyclo[3.2.1]octan-6-yl hydrogen sulfate (Compound 1)

(1) Preparation of tert-butyl 2-((2S,5R)-6-(benzyloxy)-7-oxo-1,6-diazabicyclo[3.2.1]octane-2-carboxamido)-7-azaspiro[3.5]nonane-7-carboxylate

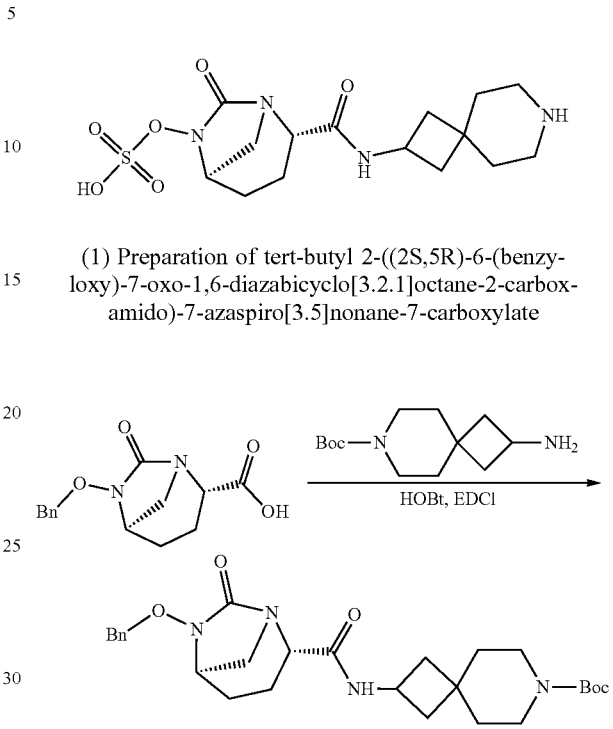

(2S,5R)-6-(benzyloxy)-7-oxo-1,6-diazabicyclo[3.2.1]octane-2-carboxylic acid (767 mg, 2.8 mmol) was dissolved in dichloromethane (35 mL), tert-butyl 2-amino-7-azaspiro[3.5]nonane-7-carboxylate (1.0 g, 4.2 mmol), 1-hydroxylbenzotriazole (567 mg, 4.2 mmol), triethylamine (848 mg, 8.4 mmol) and 1-ethyl-(3-dimethylaminopropyl)carbodiimide hydrochloride (806 mg, 4.2 mmol) were serially added, stirred at 25° C. for 16 h. Water (200 mL) and dichloromethane (200 mL) were added, the phases were separated, the organic phase was washed with saturated brine (200 mL), dried over anhydrous sodium sulfate, concentrated, and the crude product was purified by silica gel column chromatography (petroleum ether:ethyl acetate=1:1) to obtain the title compound (1.0 g, yield 71.7%).

(2) Preparation of (2S,5R)-2-((7-(tert-butyloxycarbonyl)-7-azaspiro[3.5]nonan-2-yl) carbamoyl)-7-oxo-1,6-diazabicyclo[3.2.1]octan-6-yl sulfuric acid tetra(n-butyl)ammonium salt

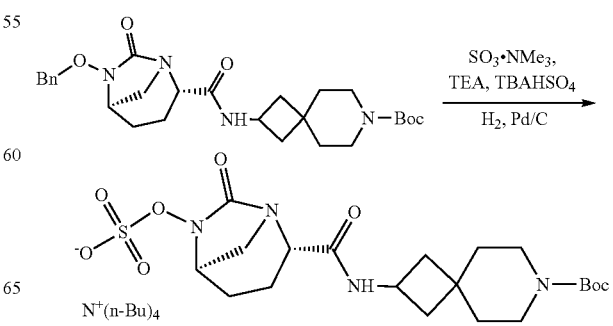

Tert-butyl 2-((2S,5R)-6-(benzyloxy)-7-oxo-1,6-diazabicyclo[3.2.1]octane-2-formamido)-7-azaspiro[3.5]nonane-7-carboxylate (500 mg, 1.0 mmol) was dissolved in a mixture solvent of isopropanol (6 mL) and water (6 mL), triethylamine (0.1 mL), sulfur trioxide-trimethylamine complex (167 mg, 1.2 mmol) and Pd/C (100 mg) were serially added, stirred under hydrogen gas atmosphere for 2 h. Suck filtration was performed to remove catalyst, water (20 mL) and ethyl acetate (20 mL) was added to the filtrate, the phases were separated, to the aqueous phase was added an aqueous solution of tetrabutylammonium hydrogen sulfate (1 mol/L, 3 mL). After shaking vigorously, dichloromethane (100 mL×2) was added for extraction, the organic phases were combined, dried over anhydrous sodium sulfate, concentrated to 10 mL, and directly used in the next reaction step.

(3) Preparation of (2S,5R)-2-(7-azaspiro[3.5]nonan-2-ylcarbamoyl)-7-oxo-1,6-diazabicyclo[3.2.1]octan-6-yl hydrogen sulfate

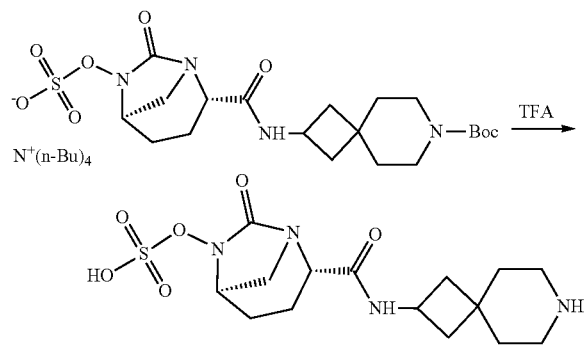

The solution obtained in the above step was cooled to 0° C., trifluoroacetic acid (4 mL) was slowly added dropwise with stirring. After the end of addition, the stirring was kept for 1 h. Concentration was performed to obtain 2 mL, and ethyl ether (5 mL) was added slowly under stirring. A large amount of white solid was precipitated, suck filtrated, and the resultant white solid was washed with acetonitrile (15 mL×2), vacuum dried to obtain white title compound (227 mg, two-step yield 58.5%).

Molecular Formula: $C_{15}H_{24}N_4O_6S$ Molecular Weight: 388.4 LC-MS (m/z): 389.2[M+H]$^{+1}$H-NMR (400 MHz, $D_2O$) δ: 4.28-4.20 (m, 1H), 4.15-4.11 (m, 1H), 3.95-3.90 (m, 1H), 3.28-3.20 (m, 1H), 3.17-3.09 (m, 2H), 3.08-3.03 (m, 2H), 2.99-2.91 (m, 1H), 2.35-2.25 (m, 2H), 2.15-2.08 (m, 1H), 2.04-1.95 (m, 1H), 1.86-1.62 (m, 8H).

Example 2: Preparation of (2S,5R)-2-((2-azaspiro[3.3]heptan-6-yl)carbamoyl)-7-oxo-1,6-diazabicyclo[3.2.1]octan-6-yl hydrogen sulfate (Compound 2)

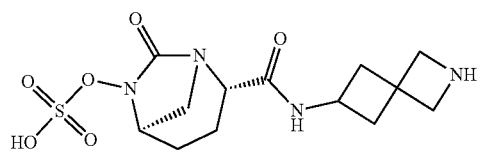 [SMILES: O=C(NC1CC2(CNC2)C1)[C@@H]1CC[C@@H]2CN1C(=O)N2OS(=O)(=O)O]

(1) Preparation of (2S,5R)-2-((2-(tert-butyloxycarbonyl)-2-azaspiro[3.3]heptan-6-yl) carbamoyl)-7-oxo-1,6-diazabicyclo[3.2.1]octan-6-ylsulfuric acid tetra(n-butyl)ammonium salt

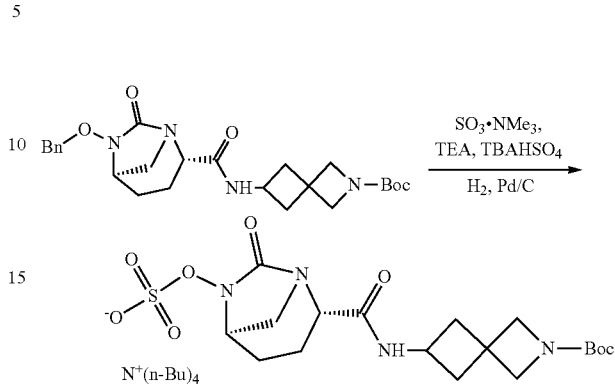

Tert-butyl 6-((2S,5R)-6-(benzyloxy)-7-oxo-1,6-diazabicyclo[3.2.1]octane-2-carboxamido)-2-azaspiro[3.3]heptane-2-carboxylate (2.5 g, 5.31 mmol) was dissolved in a mixture solvent of isopropanol (50 mL) and water (50 mL), Pd/C (250 mg, mass fraction 10%), sulfur trioxide-trimethylamine complex (887 mg, 6.37 mmol) and triethylamine (134 mg, 1.33 mmol) ware serially added, the system was purged with hydrogen gas, stirred at 25° C. for 16 h. After completion of the reaction as measured by LC-MS, filtration was performed, to the filtrate were added water (100 mL) and ethyl acetate (200 mL), the phases were separated, to the aqueous phase was added tetrabutylammonium hydrogen sulfate (1.98 g, 5.83 mmol), and the system was stirred at 25° C. for 20 min, dichloromethane (150 mL) was added, the phases were separated, the aqueous phase was extracted with dichloromethane (100 mL×2), the organic phases were combined, dried over anhydrous sodium sulfate, suck filtrated, and the filtrate was distilled to dryness to obtain the title compound in white color (3.4 g, yield 91.4%).

(2) Preparation of (2S,5R)-2-((2-azaspiro[3.3]heptan-6-yl)carboxamido)-7-oxo-1,6-diazabicyclo[3.2.1]octan-6-yl hydrogen sulfate

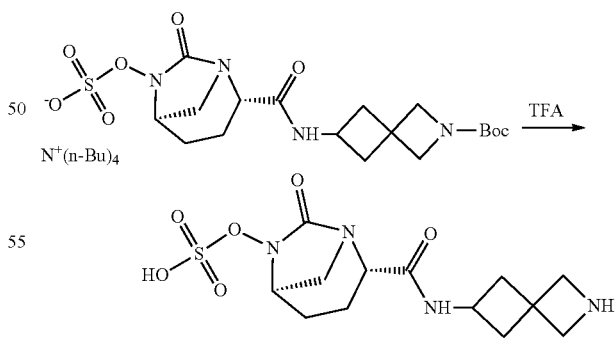

(2S,5R)-2-((2-(tert-butyloxycarbonyl)-2-azaspiro[3.3]heptan-6-yl)carboxamido)-7-oxo-1,6-diazabicyclo[3.2.1]octan-6-ylsulfuric acid tetra(n-butyl)ammonium salt (3.4 g, 4.85 mmol) was added in dichloromethane (16 mL), cooled to 0° C., trifluoroacetic acid (8 mL) was added. Reaction was performed at 0° C. for 0.5 h, LC-MS was used to detect the end of reaction. Solvent was removed by vacuum distillation, and acetonitrile (150 mL) was added under ultrasonic to get a large amount of with precipitate. After suck filtration, the filter cake was washed with acetonitrile (20 mL×3), dried in vacuum to obtain the title compound (1.52 g, 86.9%).

Molecular Formula: $C_{13}H_{20}N_4O_6S$ Molecular Weight: 360.4 LC-MS (m/z): 361.1[M+H]$^+$ The title compound was processed to obtain an aqueous solution of 5 mg/ml, and the specific rotation of the title compound was determined to be −44±−2° according to the Optical Rotation Determination Method 0621 as described in the General Rule of the Chinese Pharmacopoeia 2015 edition.

$^1$H-NMR (400 MHz, D$_2$O) δ: 4.14-4.10 (m, 4H), 4.02 (s, 2H), 3.91 (d, J=6.4 Hz, 1H), 3.22 (d, J=12.4 Hz, 1H), 2.95 (d, J=12.4 Hz, 1H), 2.66-2.60 (m, 2H), 2.27-2.22 (m, 2H), 2.12-2.06 (m, 1H), 2.01-1.96 (m, 1H), 1.86-1.79 (m, 1H), 1.74-1.68 (m, 1H).

Example 2-A: Preparation of (2R,5R)-2-((2-azaspiro[3.3]heptan-6-yl) carbamoyl)-7-oxo-1,6-diazabicyclo[3.2.1]octan-6-yl hydrogen sulfate (Compound 2-2)

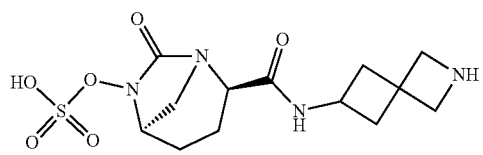 [SMILES: O=C(NC1CC2(CNC2)C1)[C@H]1CC[C@@H]2CN1C(=O)N2OS(=O)(=O)O]

(1) Preparation of ethyl (R)-2-((tert-butoxy carbonyl)amino-6-(dimethyl(oxo)-λ$^6$-sulfanylidene)-5-oxo-hexanoate

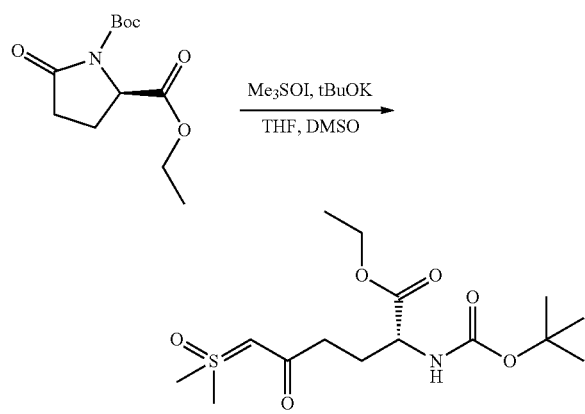

DMSO (240 mL) was added to a solution of trimethylsulfoxonium iodide (41 g, 186.3 mmol) and potassium tert-butoxide (20 g, 178.2 mmol) in THF (200 mL), reacted at 25° C. for 2 h, then cooled to −15° C. A solution of 1-(tert-butyl) 2-ethyl (R)-5-oxopyrrolidine-1,2-dicarboxylate (40 g, 155.5 mmol) in THF (120 mL) was added dropwise to the reaction system, then reacted for 3 h.

After completion of the reaction, it was quenched with a saturated solution of ammonium chloride (200 mL), extracted with ethyl acetate (200 mL×3), and the organic layers were combined, dried over anhydrous sodium sulfate, filtered, and the filtrate was concentrated to obtain the crude product (50 g).

(2) Preparation of ethyl (R,Z)-5-((benzyloxy)imino)-2-((tert-butoxylcarbonyl)amino)-6-chloro-hexanoate

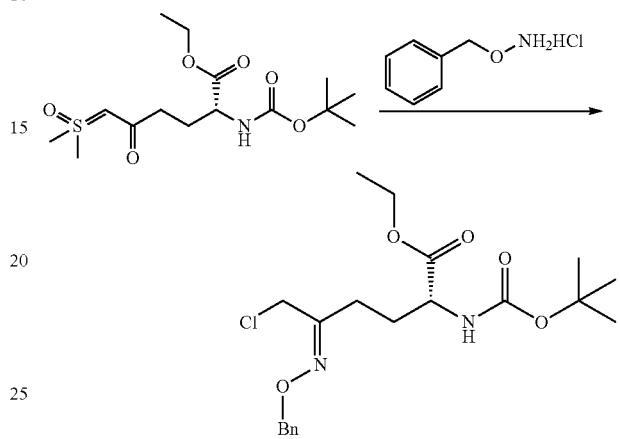

Ethyl (R)-2-((tert-butoxylcarbonyl)amino-6-(dimethyl (oxo)-λ$^6$-sulfanylidene)-5-oxo-hexanoate (50 g, crude product) was dissolved in ethyl acetate (200 mL), then O-benzylhydroxylamino hydrochloride (26 g, 162.9 mmol) was added, reacted at 60° C. for 3 h; after completion of the reaction, the reaction solution was washed with saturated brine (200 mL) to obtain the crude product (50 g).

(3) Preparation of ethyl (R,E)-5-((benzyloxy)imino) piperidine-2-carboxylate

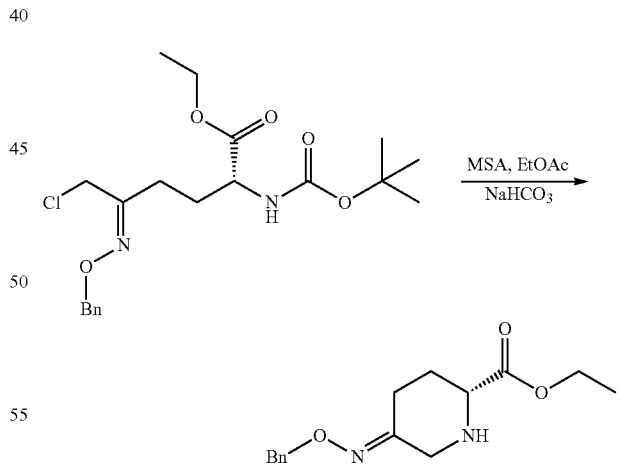

Ethyl (R,Z)-5-((benzyloxy)imino)-2-((tert-butoxycarbonyl)amino)-6-chlorohexanoate (50 g, crude product) was dissolved in ethyl acetate (200 mL), methylsulfonic acid (30 mL) was added dropwise, reacted at 50° C. for 3 h; after completion of the reaction, it was cooled to 25° C., added dropwise with a saturated solution of sodium hydrogen carbonate until no more bubble was generated, then sodium hydrogen carbonate (10 g, 119.0 mmol) was added, the reaction system was heated to 50° C., stirred vigorously for 3 h. After completion of the reaction, separation was carried out, and the organic layer was washed with saturated brine (200 mL), and concentrated to obtain the crude product (25 g).

(4) Preparation of ethyl (2R)-5-((benzyloxy)amino)piperidine-2-carboxylate

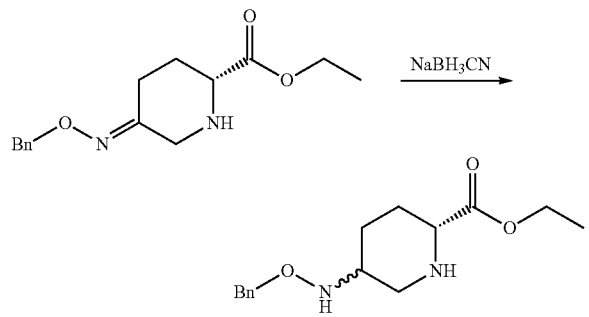

Ethyl (R,E)-5-((benzyloxy)imino)piperidine-2-carboxylate (25 g, crude product) was dissolved in a mixture solvent of ethyl acetate (300 mL) and concentrated sulfuric acid (20 mL); at 25° C., sodium cyanoborohydride (10 g, 158.7 mmol) was added in batches, the reaction was continued for 3 h; after completion of the reaction, water (200 mL) was added for extraction, the aqueous layer was adjusted with sodium hydrogen carbonate to pH=7, then extracted with ethyl acetate (200 mL×3), and the organic layers were combined, concentrated to obtain the crude product (25 g).

(5) Preparation of ethyl (2R,5R)-5-((benzyloxy)amino)piperidine-2-carboxylate

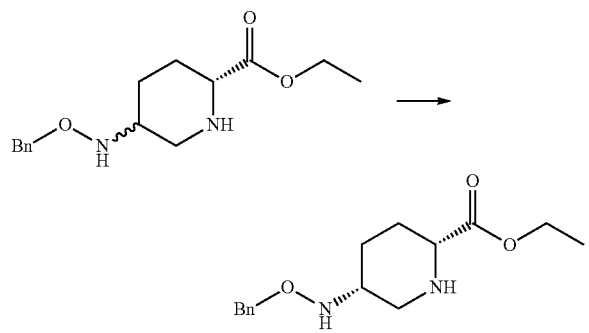

Ethyl (2R)-5-((benzyloxy)amino)piperidine-2-carboxylate (25 g, crude product) was dissolved in ethanol (80 mL), heated to 40° C., then a solution of oxalic acid (9.0 g, 100 mmol) in ethanol (50 mL) was added dropwise; after addition, the system was stirred for 1 h. A white solid was precipitated, warm filtrated, the filtrate was concentrated, the residue was dissolved in water (150 mL), adjusted with sodium hydrogen carbonate to pH=7, then extracted with ethyl acetate (150 mL×3), the organic layers were combined, concentrated, and the residue was subjected to reverse phase silica gel column chromatography (acetonitrile/water=0%-30%) to obtain a product (2.5 g, yield of the five steps was 5.8%).

(6) Preparation of ethyl (2R,5R)-6-(benzyloxyl)-7-oxo-1,6-diazabicyclo[3.2.1]octane-2-carboxylate

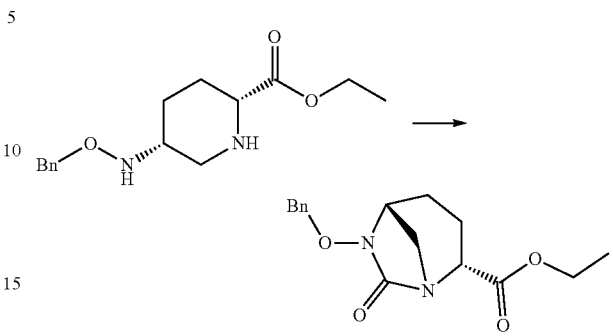

Ethyl (2R,5R)-5-((benzyloxy)amino)piperidine-2-carboxylate (2.5 g, 8.98 mmol) and DIEA (4.6 g, 35.6 mmol) were dissolved in DCM (80 mL), cooled to −10° C., triphosgene (1.0 g, 3.37 mmol) was slowly added, then the system was moved and reacted at 25° C. for 16 h. After completion of the reaction, the system was concentrated, and the residue was purified with silica gel column chromatography (petroleum ether:ethyl acetate=1:1) to obtain the product (1.5 g, yield was 54.9%).

(7) Preparation of (2R,5R)-6-(benzyloxy)-7-oxo-1,6-diazabicyclo[3.2.1]octane-2-carboxylic acid

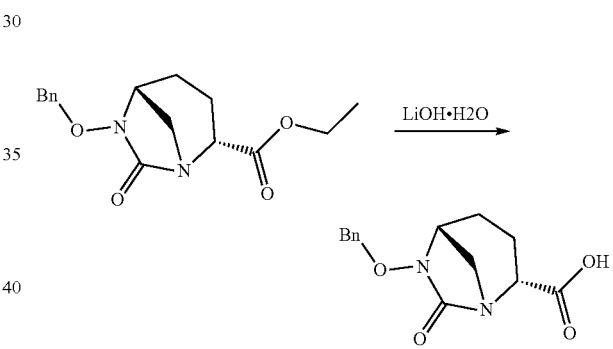

At 0° C., a solution of lithium hydroxide monohydrate (414 mg, 9.86 mmol) in water (4 mL) was added dropwise to ethyl (2R,5R)-6-(benzyloxy)-7-oxo-1,6-diazabicyclo[3.2.1]octane-2-carboxylate (1.5 g, 4.93 mmol) in a mixture solvent of THF (12 mL) and water (4 mL), reacted at 0° C. for 4 h, after completion of the reaction, ethyl acetate (80 mL) was added for extraction, and the aqueous layer was cooled to 0° C. adjusted with diluted hydrochloric acid (1M) to pH=2, then extracted with DCM (50 mL×3). The organic phases were combined, dried over anhydrous sodium sulfate, filtrated, and the filtrate was concentrated to obtain a product (0.12 g, yield was 8.8%).

(8) Preparation of tert-butyl 6-((2R,5R)-6-(benzyloxy)-7-oxo-1,6-diazabicyclo[3.2.1]octane-2-carboxamido)-2-azaspiro[3.3]heptane-2-carboxylate

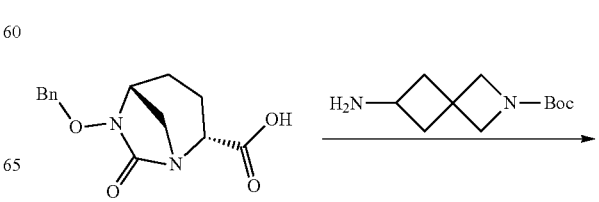

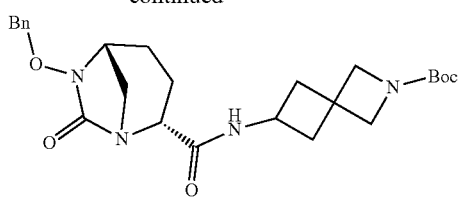

(2R,5R)-6-(benzyloxy)-7-oxo-1,6-diazabicyclo[3.2.1]octane-2-carboxylic acid (0.12 g, 0.43 mmol), tert-butyl 6-amino-2-azaspiro[3.3]heptane-2-carboxylate (92 mg, 0.43 mmol), triethylamine (96 mg, 0.95 mmol). HOBT (87 mg, 0.64 mmol), EDCI (165 mg, 0.86 mmol) were serially added to DCM (20 mL), reacted at 25° C. for 3 h; the reaction solution was concentrated after completion of the reaction, and the residue was purified with silica gel column chromatography (petroleum ether:ethyl acetate=1:1) to obtain the product (0.15 g, yield was 73.4%).

(9) Preparation of tetra(n-butyl)ammonium (2R,5R)-2-((2-(tert-butoxylcarbonyl)-2-azaspiro[3.3]heptan-6-yl)carbamoyl)-7-oxo-1,6-diazabicyclo[3.2.1]octan-6-yl sulfate

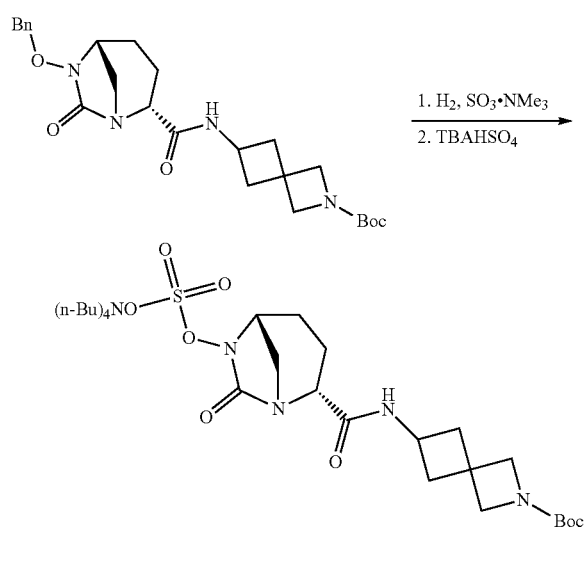

Tert-butyl 6-((2R,5R)-6-(benzyloxy)-7-oxo-1,6-diazabicyclo[3.2.1]octan-2-carboxamido)-2-azaspiro[3.3]heptane-2-carboxylate (0.15 g, 0.32 mmol), Pd/C (30 mg, 10%), sulfur trioxide trimethylamine (53 mg, 0.38 mmol), and triethylamine (13 mg, 0.13 mmol) were serially added to isopropanol/water (10 mL, 1:1), reacted under hydrogen atmosphere and 25° C. for 16 h. After completion of the reaction, the reaction solution was filtrated, the filtrate was distilled to remove isopropanol, the aqueous layer was washed with ethyl acetate (10 mL), then to the aqueous layer was added tetrabutylammonium hydrogen sulfate (120 mg, 0.35 mmol), stirred at 25° C. for 1 h, then the aqueous layer was extracted with DCM (50 mL×3), and the organic layers were combined, dried over anhydrous sodium sulfate, filtrated, the filtrate was concentrated to obtain the product (0.17 g, yield was 75.7%).

(10) Preparation of (2R,5R)-2-((2-azaspiro[3.3]heptan-6-yl)carbamoyl)-7-oxo-1,6-diazabicyclo[3.2.1]octan-6-yl hydrogen sulfate

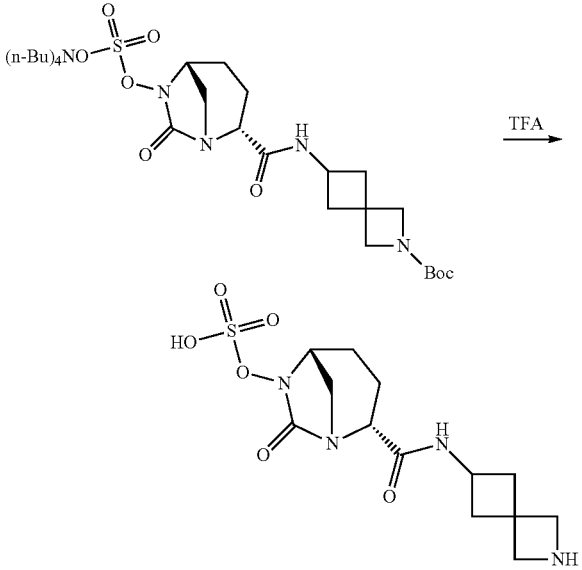

At 0° C., tetra(n-butyl)ammonium (2R,5R)-2-((2-(tert-butoxylcarbonyl)-2-azaspiro[3.3]heptan-6-yl)carbamoyl)-7-oxo-1,6-diazabicyclo[3.2.1]octan-6-yl sulfate (0.17 g, 0.24 mmol) was dissolved in DCM (2 mL), then trifluoroacetic acid (1 mL) was added. After reaction for 0.5 h, the reaction solution was poured into acetonitrile (10 mL), solid was precipitated, then isopropanol (5 mL) was added, filtrated, the filter cake was washed with acetonitrile (10 mL), and dried to obtain the product (50 mg, yield was 57.8%), Molecular formula: $C_{13}H_{20}N_4O_6S$ Molecular weight: 360.39 LC-MS (m/z): 361.2 (M+H$^+$)

$^1$H-NMR (400 MHz, D$_2$O) δ: 4.08-4.12 (m, 4H), 4.02 (s, 2H), 3.90 (d, J=6.8 Hz, 1H), 3.20 (d, J=12.0 Hz, 1H), 2.93 (d, J=12.0 Hz, 1H), 2.59-2.65 (m, 2H), 2.20-2.26 (m, 2H), 2.06-2.09 (m, 1H), 1.94-2.06 (m, 1H), 1.78-1.84 (m, 1H), 1.66-1.78 (m, 1H).

Example 3: Preparation of (2S,5R)-2-((2-azaspiro[3.5]nonan-7-yl)carbamoyl)-7-oxo-1,6-diazabicyclo[3.2.1]octan-6-yl hydrogen sulfate trifluoroacetic acid salt (Compound 3)

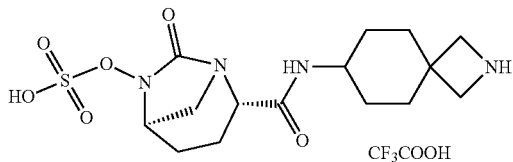 [SMILES: O=C(NC1CCC2(CC1)CNC2)[C@@H]1CC[C@@H]2CN1C(=O)N2OS(=O)(=O)O ; "CF3COOH"]

(1) Preparation of ethyl 1,4-dioxaspiro[4.5]decane-8-carboxylate

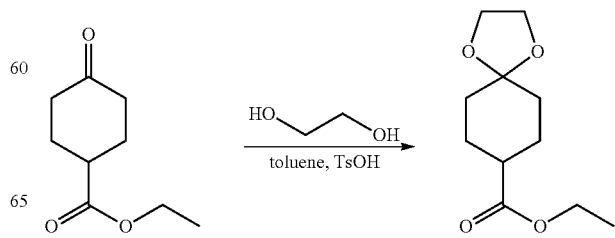

To a reaction flask, ethyl 4-oxocyclohexane-1-carboxylate (50 g, 293.76 mmol), toluene (300 mL), ethylene glycol (20 g, 322.23 mmol) and p-methylphenyl sulfonic acid (1 g, 5.81 mmol) were added. The reaction solution was stirred at room temperature overnight, ethyl acetate (200 mL) was added for dilution, washed sequentially with sodium hydrogen carbonate solution (200 mL×2) and water (200 mL×3), dried over anhydrous sodium sulfate, concentrated, and the residue was purified by silica gel column chromatography (ethyl acetate: petroleum ether=1:20-1:10) to obtain the title compound as yellow oil (33 g, yield 52.0%).

(2) Preparation of diethyl 1,4-dioxaspiro[4.5]decane-8,8-dicarboxylate

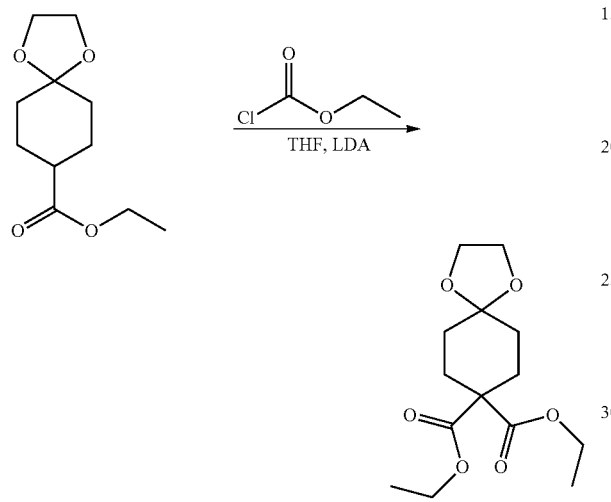

To a reaction flask, diisopropylamine (10 g, 98.82 mmol) and tetrahydrofuran (250 mL) were added, purged with nitrogen gas for 3 times, to the system was added dropwise n-butyl lithium (41 mL) under nitrogen gas protection at −30° C., after the end of adding material, the reaction was performed at −30° C. for 30 min. Then, ethyl 1,4-dioxaspiro[4.5]decane-8-carboxylate (20 g, 93.35 mmol) in tetrahydrofuran (100 mL) solution was added dropwise at −78° C., the reaction was performed at −78° C. for 1 h; ethyl chloroformate (12 g, 110.57 mmol) in tetrahydrofuran (50 mL) solution was added dropwise, the reaction was performed at −78° C. for 0.5 h. Water (50 mL) was added to quench the reaction, and ethyl acetate (300 mL) was added for dilution, after the phases were separated, the organic phase was washed with water (200 mL×3), dried over anhydrous sodium sulfate, concentrated, and the residue was purified by silica gel column chromatography (ethyl acetate: petroleum ether=1:20-1:15) to obtain the title compound as yellow oil (23 g, yield 86.5%).

(3) Preparation of 1,4-dioxaspiro[4.5]decane-8,8-diyl)dimethanol

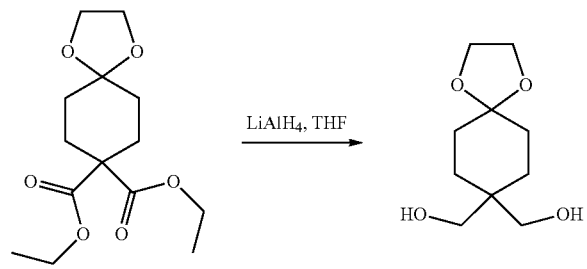 [SMILES: CCOC(=O)C1(C(=O)OCC)CCC2(CC1)OCCO2 ; OCC1(CO)CCC2(CC1)OCCO2]

Under protection of nitrogen gas, aluminum lithium tetrahydride (7.3 g, 192.4 mmol) and tetrahydrofuran (500 mL) were added to a reaction flask. A solution of diethyl 1,4-dioxaspiro[4.5]decane-8,8-dicarboxylate (23 g, 80.33 mmol) in tetrahydrofuran (300 mL) was added dropwise at 0° C., stirred at 0° C. for 30 min. Water (7.3 mL) was added for quenching, filtrated, the filter cake was washed with tetrahydrofuran (300 mL×3), and the organic layer was separated, dried over anhydrous sodium sulfate, concentrated in vacuum, then the residue was purified by silica gel column chromatography (ethyl acetate:petroleum ether=1:15-1:5) to obtain the title compound as a white solid (14 g, yield 87.5%).

(4) Preparation of 2-(2,4-dimethoxybenzyl)-8,11-dioxa-2-azadispiro[3.2.4$^7$.2$^4$]tridecane

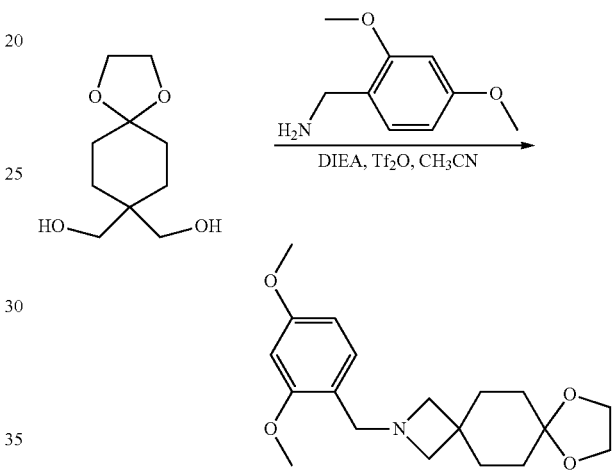

(1,4-dioxaspiro[4.5]decane-8,8-diyl)dimethanol (8 g, 39.56 mmol) was dissolved in acetonitrile (160 mL), to which was added N,N-diisopropylamine (15.3 g, 118.38 mmol), and trifluoromethylsulfonic anhydride (24.6 g, 87.19 mmol) was added dropwise at −30° C., then reacted at −30° C. for 30 min, N,N-diisopropylamine (15.3 g, 118.38 mmol) and (2,4-dimethoxyphenyl)methylamine (7.9 g, 47.25 mmol) was added, and the system was heated to 80° C. and reacted for 1.5 h. Ethyl acetate (200 mL) was added for dilution, water (300 mL×3) was used for washing, anhydrous sodium sulfate was used for drying. After concentration, the residue was purified by silica gel column chromatography (dichloromethane:methanol=1:50-1:10) to obtain the title compound as a white solid (4 g, yield 30%).

(5) Preparation of tert-butyl 8,11-dioxa-2-azadispiro[3.2.4$^7$.2$^4$]tridecane-2-carboxylate

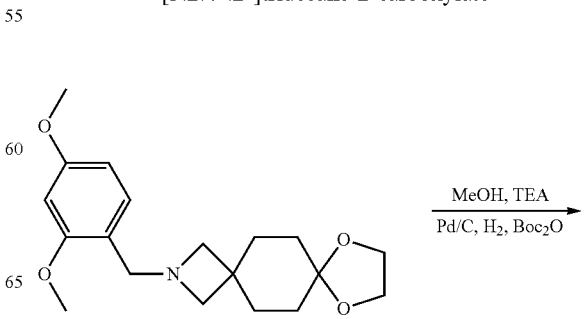

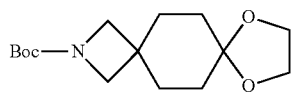

In a high-pressure autoclave, 2-(2,4-dimethoxybenzyl)-8,11-dioxa-2-azadispiro[3.2.4⁷.2⁴]tridecane (4 g, 12.00 mmol), methanol (200 mL), Pd/C (10%, 800 mg), triethylamine (3.64 g, 35.97 mmol) and ditert-butyl dicarbonate (3.14 g, 14.39 mmol) were added, purged with hydrogen gas, reacted at 80° C. overnight. The reaction solution was cooled, concentrated, and the residue was purified by silica gel column chromatography (ethyl acetate:petroleum ether=1:10-1:5) to obtain the title compound as a white solid (2.1 g, yield 62%).

(6) Preparation of tert-butyl 7-oxo-2-azaspiro[3.5]nonane-2-carboxylate

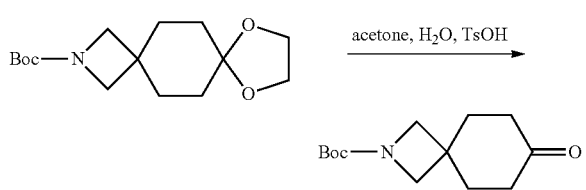

Tert-butyl 8,11-dioxa-2-azadispiro[3.2.4⁷.2⁴]tridecane-2-carboxylate (2 g, 7.06 mmol) and p-toluenesulfonic acid (244 mg, 1.42 mmol) were dissolved in a mixture solvent of acetone and water (10:1, 30 mL), stirred at 45° C. overnight. The reaction was cooled, concentrated in vacuum, and the residue was purified by silica gel column chromatography (ethyl acetate:petroleum ether=1:10-1:2) to obtain the title compound as a white solid (1.2 g, yield 71.0%).

(7) Preparation of tert-butyl 7-amino-2-azaspiro[3,5]nonane-2-carboxylate

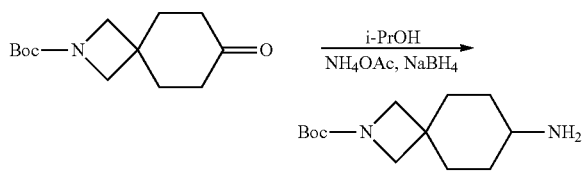

Tert-butyl 7-oxo-2-azaspiro[3,5]nonane-2-carboxylate (1.2 g, 5.01 mmol) and ammonium acetate (1.55 g, 20.11 mmol) were dissolved in isopropanol (30 mL), sodium borohydride (380.76 mg, 10.02 mmol) was added at −20° C. in batches, and the reaction solution was stirred at room temperature for 1 h, diluted with ethyl acetate (50 mL), washed with water (30 mL×3), dried over anhydrous sodium sulfate, concentrated, the residue was purified by silica gel column chromatography (ethyl acetate:petroleum ether=1:10-1:1) to obtain the title compound as a white solid (800 mg, yield 67%).

(8) Preparation of tert-butyl 7-((2S,5R)-6-(benzyloxy)-7-ooxo-1,6-diazabicyclo[3.2.1]octane-2-carboxamido)-2-azaspiro[3.5]nonane-2-carboxylate

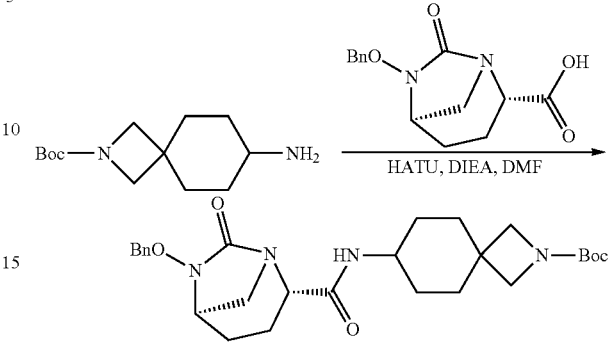

Under protection of nitrogen gas, (2S,5R)-6-(benzyloxy)-7-oxo-1,6-diazabicyclo[3.2.1]octane-2-carboxylic acid (1.09 g, 3.95 mmol) was dissolved in DMF (20 mL) and N,N-diisopropylamine (1.28 g, 9.90 mmol), and at 0° C. HATU (1.88 g, 4.95 mmol) was added, stirred for 30 min, then tert-butyl 7-amino-2-azaspiro[3.5]nonane-2-carboxylate (800 mg, 3.33 mmol) was added, the reaction solution was stirred at room temperature for 2 h. Ethyl acetate (50 mL) was added, the reaction solution was washed with water (30 mL×3), dried over anhydrous sodium sulfate, concentrated, and the residue was purified by silica gel column chromatography (ethyl acetate:petroleum ether=1:5-1:1) to obtain the title compound as a white solid (600 mg, yield 36.5%).

(9) Preparation of tetra(n-butyl)ammonium (2S,5R)-2-((2-(tert-butyloxycarbonyl)-2-azaspiro[3.5]nonane-7-yl)carbamoyl)-7-oxo-1,6-diazabicyclo[3.2.1]octan-6-yl sulfate

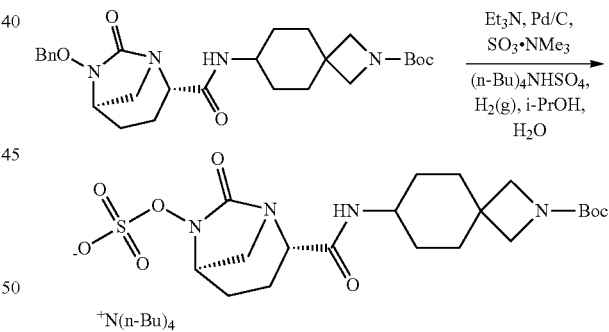

Tert-butyl 7-((2S,5R)-6-(benzyloxy)-7-oxo-1,6-diazabicyclo[3.2.1]octane-2-carboxamido)-2-azaspiro[3.5]nonane-2-carboxylate (600 mg, 1.20 mmol) was dissolved in a mixture solvent of isopropanol and water (1:1, 10 mL), to which were added SO₃NMe₃ (250 mg) and triethylamine (363 mg, 3.59 mmol), then added Pd/C (mass fraction 10%, 100 mg), purged with nitrogen gas for 3 times, purged with hydrogen gas, the reactants were stirred at room temperature for 1 h, filtered, the filtrate was extracted with ethyl acetate (20 mL×2), to the aqueous phase was added water (10 mL) and tetrabutylammonium sulfate (2 mL), then extracted with dichloromethane (20 mL×3). The organic phases were combined, dried over anhydrous sodium sulfate, concentrated in vacuum to obtain the title compound as a white solid (400 mg, yield 45.6%).

(10) Preparation of (2S,5R)-2-((2-azaspiro[3.5]nonane-7-yl)carbamoyl)-7-oxo-1,6-diazabicyclo[3.2.1]octan-6-yl hydrogen sulfate.trifluoroacetate

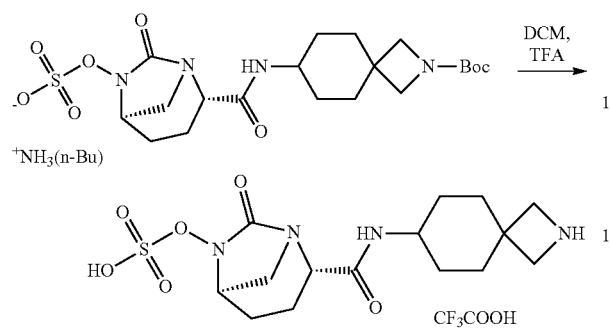

Tetra(n-butyl)ammonium (2S,5R)-2-((2-(tert-butyloxycarbonyl)-2-azaspiro[3.5]nonane-7-yl) carbamoyl)-7-oxo-1,6-diazabicyclo[3.2.1]octan-6-yl sulfate (400 mg, 0.55 mmol) was dissolved in dichloromethane (10 mL), at 0° C. trifluoroacetic acid (1 mL) was added dropwise. The system was reacted at 0° C. for 1 h, and ethyl ether (30 mL) was added, filtrated to obtain a solid. The solid was purified by high performance liquid chromatography to obtain the title compound as a yellow solid (12 mg, yield 6%).

Molecular Formula: $C_{17}H_{25}F_3N_4O_8S$, Molecular Weight: 502.46, LC-MS (ES, m/z): 389[M+H]+ $^1$H-NMR (300 MHz, $D_2O$) δ: 4.15 (s, 1H), 3.95 (d, J=6 Hz, 1H), 3.91-3.70 (m, 5H), 3.67-3.54 (m, 2H), 3.41-3.34 (m, 1H), 3.27-3.20 (m, 1H), 2.24-1.92 (m, 4H), 1.89-1.51 (m, 5H), 1.33-1.21 (m, 2H).

Example 4: Preparation of (2S,5R)-2-((8-azabicyclo[3.2.1]octane-3-yl) carbamoyl)-7-oxo-1,6-diazabicyclo[3.2.1]octan-6-yl hydrogen sulfate (Compound 4)

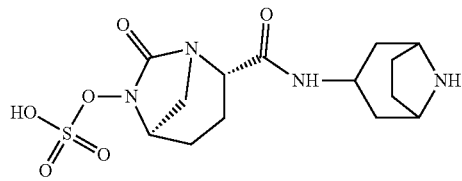 [SMILES: O=C(NC1CC2CCC(C1)N2)[C@@H]1CC[C@@H]2CN1C(=O)N2OS(=O)(=O)O]

(1) Preparation of benzyl (2S)-2-((tert-butoxycarbonyl)amino-6-(dimethyl(oxo)-λ$^6$-sulfanylidene)-5-oxohexanoate

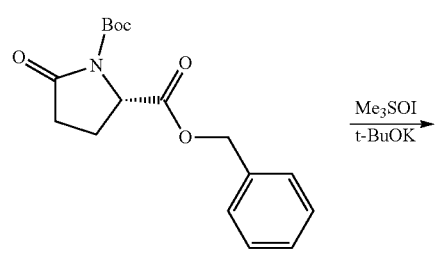

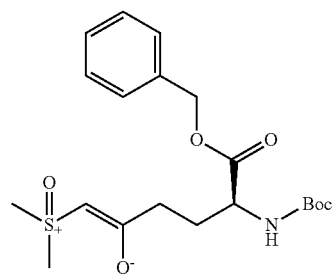

Trimethylsulfonyl iodide (16 g, 72.7 mmol) and potassium tert-butoxide (8 g, 71.3 mmol) were added to tetrahydrofuran (100 mL), DMSO (100 mL) was added, stirred and reacted at 25° C. for 2 h, cooled to about −10° C. The solution of (S)-2-benzyl 1-tert-butyl 5-oxopyrrolidine-1,2-dicarboxylate (20 g, 62.6 mmol) in tetrahydrofuran (60 mL) was added. After addition, the reaction was performed at a low temperature under stirring for 8 h. The reaction solution was quenched with an aqueous saturated solution (100 mL) of ammonium chloride, ethyl acetate (100 mL×3) was added for extraction, and the organic phases were combined, dried over anhydrous sodium sulfate, filtrated, concentrated to 120 mL. The crude product was directly used in the next reaction step.

(2) Preparation of benzyl (S)-5-((benzyloxy)imido)-2-((tert-butoxycarbonyl)amino)-6-chlorohexanoate

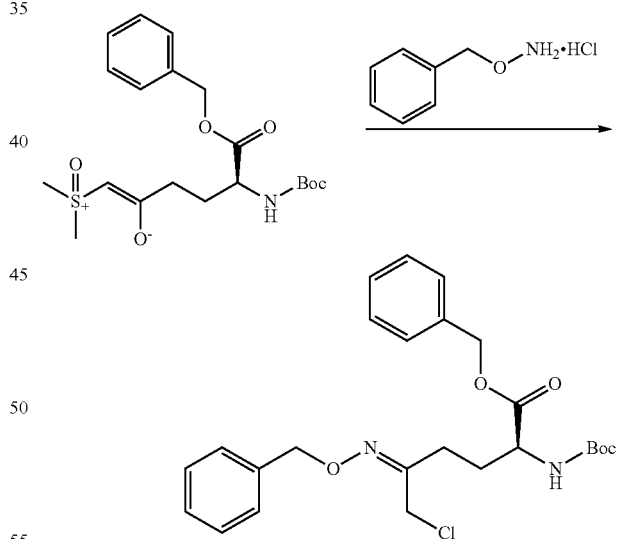

O-benzylhydroxylamine hydrochloride (10.5 g, 65.8 mmol) was added to a solution of the compound as obtained in the previous step in ethyl acetate (120 mL), then ethyl acetate (80 mL) was added. The reaction solution was heated to 80° C. stirred and reacted for 6 h, and then cooled to 25° C. An aqueous saturated solution of sodium chloride was added for washing, the phases were separated, and the separated organic phase was dried over anhydrous sodium sulfate, filtrated, concentrated to 100 mL, and directly used in the next reaction step.

(3) Preparation of benzyl (S)-5-((benzyloxy)imido)piperidine-2-carboxylate

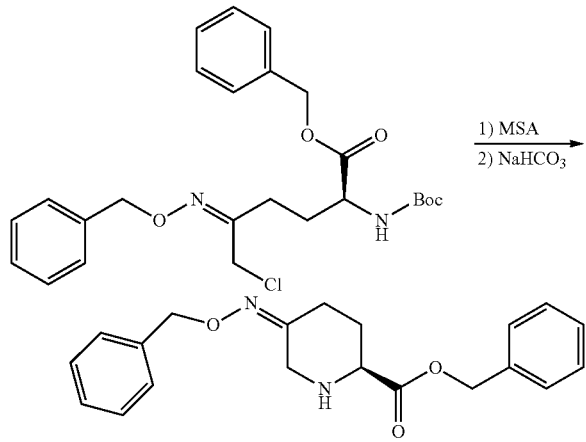

Methylsulfonic acid (12 mL, 0.185 mmol) was added to a solution of benzyl (S)-5-((benzyloxy)imido)-2-((tert-butoxycarbonyl)amino)-6-chlorohexanoate as obtained in the previous step in ethyl acetate (100 mL), heated to 40° C., stirred and reacted for 2 h, and then the reaction solution was cooled to 0° C., an aqueous saturated solution (100 mL) of sodium hydrogen carbonate was slowly added, heated to 50° C., stirred and reacted for 2 h. The phases were separated, and the organic phase was washed with an aqueous saturated solution (100 mL) of sodium chloride, dried over anhydrous sodium sulfate, filtrated, concentrated. The crude product was purified by silica gel column chromatography (petroleum ether:ethyl acetate=2:1) to obtain the title compound (9.2 g, yield 43.4%).

(4) Preparation of benzyl (2S)-5-((benzyloxy)amino)piperidine-2-carboxylate

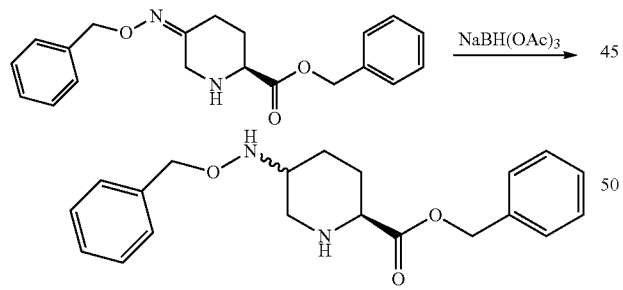

Benzyl (S)-5-((benzyloxy)imido)piperidine-2-carboxylate (9 g, 26.6 mmol) was dissolved in ethyl acetate (100 mL), concentrated sulfuric acid (7 mL) was added, the system was cooled to −20° C., and NaBH(OAc)₃ (11 g, 51.9 mmol) was added. The reaction solution was stirred and reacted at 25° C. for 6 h, and then water (100 mL) was added. The reaction solution was regulated with aqueous ammonia to pH 7, and the phases were separated. The organic phase was washed with water (100 mL), dried over anhydrous sodium sulfate, filtrated, concentrated to 50 mL. The crude product was directly used in the next reaction step.

(5) Preparation of benzyl (2S,5R)-5-((benzyloxy)amino)piperidine-2-carboxylate oxalate

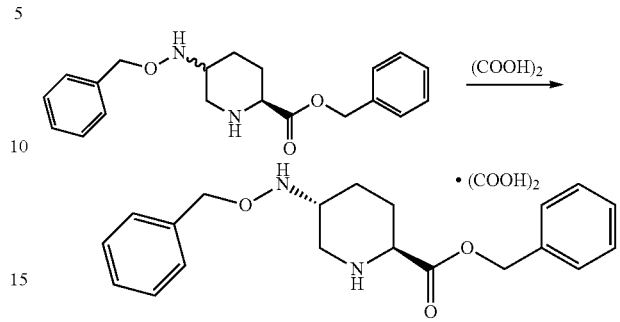

The benzyl (2S)-5-((benzyloxy)amino)piperidine-2-carboxylate solution (50 mL) as obtained in the previous step was heated to 45° C., 40° C. methanol (20 mL) and oxalic acid (2.4 g, 26.7 mmol) in methanol (5 mL) solution were added, and the system was cooled to 0° C., still stood for 6 h, filtrated, and the filter cake was washed with ethyl acetate (20 mL), added to methanol (25 mL), heated to 80° C., dissolved completely, cooled to 25° C. still stood for 2 h, filtered, and the filter cake was washed with methanol (5 mL), dried to obtain the title compound in white color (4.3 g, yield 37.7%).

(6) Preparation of benzyl (2S,5R)-6-(benzyloxy)-7-oxo-1,6-diazabicyclo[3.2.1]octane-2-carboxylate

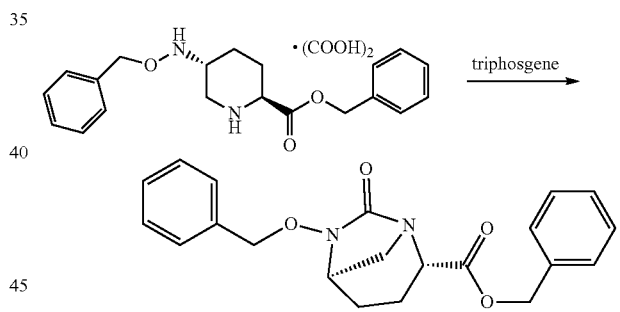

Benzyl (2S,5R)-5-(benzyloxy)amino)piperidine-2-carboxylate oxalate (3.7 g, 8.6 mmol) was added in ethyl acetate (50 mL), washed by adding an aqueous saturated solution (25 mL) of sodium hydrogen carbonate, the phases were separated, and the organic phase was dried over anhydrous sodium sulfate, filtered, concentrated in vacuum, dissolved by adding acetonitrile (50 mL), and then triethylamine (1.8 g, 17.8 mmol) was added, cooled to 0° C., triphosgene (1.2 g, 4 mmol) was added. After addition, the system was stirred and reacted at 25° C. for 30 min, then 4-dimethylaminopyridine (0.1 g, 0.8 mmol) was added, continuously reacted for 16 h. An aqueous saturated solution (100 mL) of sodium hydrogen carbonate and dichloromethane (100 mL) were added, and the phases were separated. The aqueous phase was extracted with dichloromethane (100 mL), and the organic phases were combined, dried over anhydrous sodium sulfate, filtrated, concentrated. The crude product was purified by silica gel column chromatography (petroleum ether:ethyl acetate=1:1) to obtain the title compound as colorless oil (2.2 g, yield 71.0%).

(7) Preparation of (2S,5R)-6-(benzyloxy)-7-oxo-1,6-diazabicyclo[3.2.1]octane-2-carboxylic acid

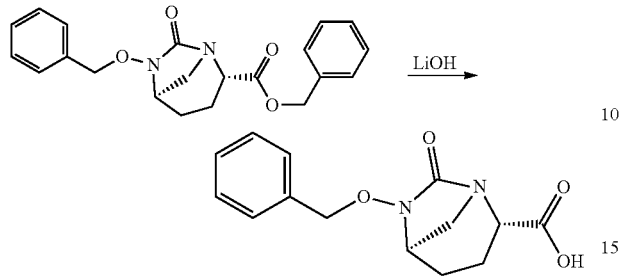

Benzyl (2S,5R)-6-(benzyloxy)-7-oxo-1,6-diazabicyclo[3.2.1]octane-2-carboxylate (2 g, 5.46 mmol) was dissolved in tetrahydrofuran (20 mL), the solution of lithium hydroxide monohydrate (0.3 g, 7.14 mmol) in water (5 mL) was added, stirred and reacted at 25° C. for 16 h. Water (20 mL) and ethyl acetate (20 mL) were added, stirred for 5 min. The phases were separated, and the aqueous phase was washed with ethyl acetate (10 mL). Diluted hydrochloric acid (1 mol/L) was added to regulate pH value to 2-3. The aqueous phase was extracted with ethyl acetate (20 mL×3), and the organic phases were combined, dried over anhydrous sodium sulfate, filtrated, concentrated to obtain the title compound as a white solid (1.2 g, yield 80%).

(8) Preparation of tert-butyl 3-((2S,5R)-6-(benzyloxy)-7-oxo-1,6-diazabicyclo[3.2.1]octane-2-carboxamido)-8-azabicyclo[3.2.1]octane-8-carboxylate

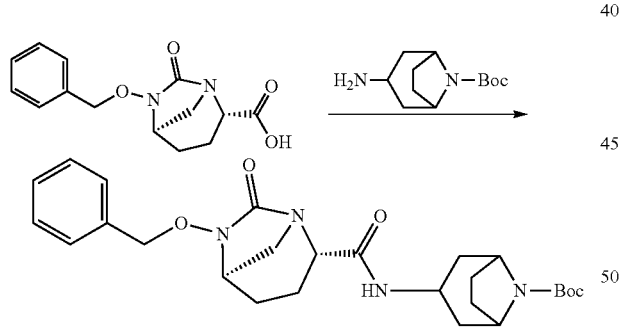

(2S,5R)-6-(benzyloxy)-7-oxo-1,6-diazabicyclo[3.2.1]octane-2-carboxylic acid (0.5 g, 1.8 mmol), tert-butyl 3-amino-8-azabicyclo[3.2.1]octane-8-carboxylate (0.4 g, 1.8 mmol), 1-hydroxylbenzotriazole (0.25 g, 1.8 mmol), 1-ethyl-(3-dimethylaminopropyl)carbodiimide hydrochloride (0.7 g, 3.6 mmol) and triethylamine (0.4 g, 3.9 mmol) were dissolved in dichloromethane (10 mL), stirred and reacted under nitrogen gas protection at 25° C. for 16 h. The reaction solution was distilled in vacuum, and the crude product was purified by silica gel column chromatography (petroleum ether:ethyl acetate=1:1) to obtain the title compound as colorless oil (0.4 g, yield 46.5%).

(9) Preparation of tert-butyl 3-((2S,5R)-6-hydroxyl-7-oxo-1,6-diazabicyclo[3.2.1]octane-2-carboxamido)-8-azabicyclo[3.2.1]octane-8-carboxylate

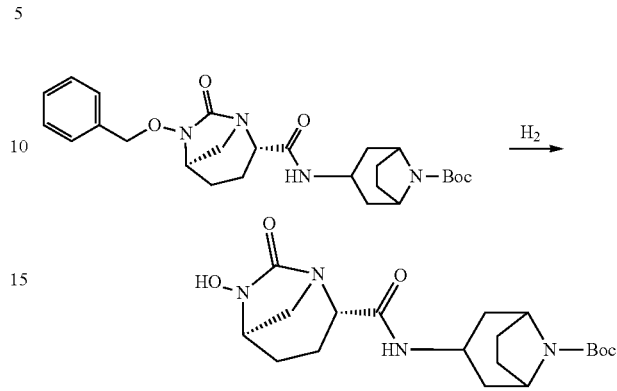

Tert-butyl 3-((2S,5R)-6-(benzyloxy)-7-oxo-1,6-diazabicyclo[3.2.1]octane-2-carboxamido)-8-azabicyclo[3.2.1]octane-8-carboxylate (0.4 g, 0.82 mmol) was dissolved in methanol (10 mL), and Pd/C (50 mg) was added. The reaction solution was stirred and reacted under compressed hydrogen gas at 25° C. for 6 h, filtrated, and the filtrate was concentrated in vacuum to obtain the title compound (0.3 g, yield 93.8%).

(10) Preparation of tetra(n-butyl)ammonium (2S,5R)-2-((8-(tert-butyloxycarbonyl)-8-azabicyclo[3.2.1]octane-3-yl)carbamoyl)-7-oxo-1,6-diazabicyclo[3.2.1]octan-6-yl sulfatesalt

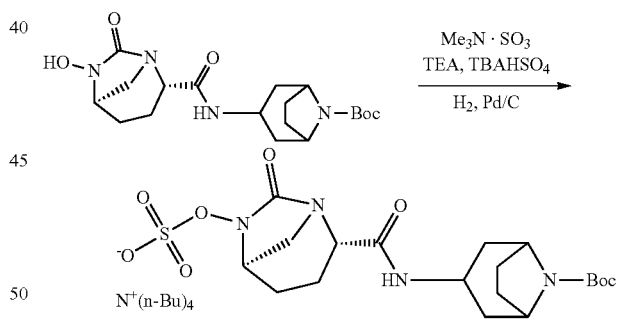

Tert-butyl 3-((2S,5R)-6-hydroxyl-7-oxo-1,6-diazabicyclo[3.2.1]octane-2-carboxamido)-8-azabicyclo[3.2.1]octane-8-carboxylate (0.3 g, 0.76 mmol) was dissolved in isopropanol (3 mL) and water (3 mL), and triethylamine (20 mg, 0.2 mmol) and sulfur trioxide-trimethylamine complex (0.15 g, 1.1 mmol) were added. The reaction solution was stirred and reacted at 25° C. for 12 h, and ethyl acetate (10 mL) and water (10 mL) were added. The phases were separated, to the aqueous phase was added an aqueous solution of tetrabutylammonium hydrogen sulfate (0.26 g, 0.76 mmol), extracted with dichloromethane (10 mL×3), and the organic phases were combined, dried over anhydrous sodium sulfate, filtrated, concentrated to obtain the title compound in white color (0.32 g, yield 59.2%).

(11) Preparation of (2S,5R)-2-((8-azabicyclo[3.2.1]octane-3-yl)carbamoyl)-7-oxo-1,6-diazabicyclo[3.2.1]octan-6-yl hydrogen sulfate (Compound 4)

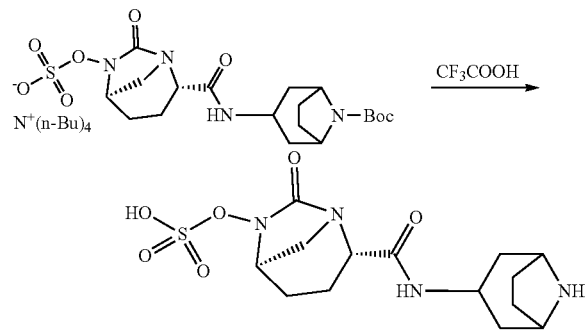

(2S,5R)-2-((8-(tert-butyloxycarbonyl)-8-azabicyclo[3.2.1]octane-3-yl)carbamoyl)-7-oxo-1,6-diazabicyclo[3.2.1]octan-6-yl sulfuric acid tetra(n-butyl)ammonium salt (0.32 g, 0.45 mmol) was dissolved in dichloromethane (5 mL), and trifluoroacetic acid (1 mL) was added. The reaction system was stirred and reacted at 25° C. for 1 h, and then the reaction solution was concentrated, ethyl ether (10 mL) was added, stirred for 30 min, filtrated. The obtained filter cake was added to acetone (10 mL), stirred, and a solution of sodium isooctoate in acetone was added. The system was regulated to pH=5, filtrated, and the resultant filter cake was separated and purified by Combiflash automatic rapid purification chromatography (mobile phase was water) to obtain the title compound as a white solid (30 mg, yield 17.6%).

Molecular Formula: $C_{14}H_{22}N_4O_6S$ Molecular Weight: 374.4 LC-MS (m/z): 375.3[M+H]+ 1H-NMR (400 MHz, MeOD) δ: 4.19 (s, 1H), 4.08-4.05 (m, 3H), 3.35-3.31 (m, 1H), 3.05-3.01 (m, 1H), 2.38-2.06 (m, 10H), 1.98-1.81 (m, 2H).

Example 5: Preparation of (2S,5R)-2-((3-azabicyclo[3.2.1]octan-8-yl) carbamoyl)-7-oxo-1,6-diazabicyclo[3.2.1]octan-6-yl hydrogen sulfate (Compound 5)

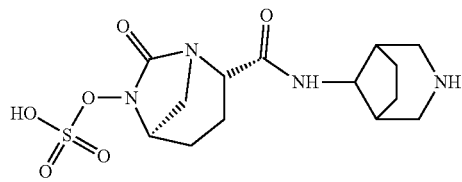

(1) Preparation of tert-butyl 8-(2,4-dimethoxybenzylamino)-3-azabicyclo[3.2.1]octane-3-carboxylate

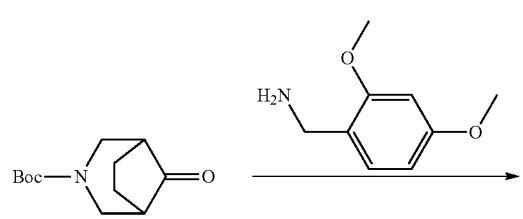

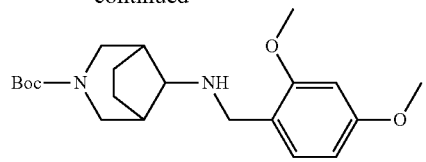

Tert-butyl 8-oxo-3-azabicyclo[3.2.1]octane-3-carboxylate (0.8 g, 3.55 mmol) and (2,4-dimethoxyphenyl)methylamine (0.6 g, 3.59 mmol) was dissolved in dichloromethane (10 mL), acetic acid (20 μL) and sodium triacetyloxyborohydrate (2 g, 9.44 mmol) were added, stirred and reacted at 25° C. for 2 h. The reaction solution was quenched with water (10 mL), the phases were separated, extracted with dichloromethane (20 mL×3), and the organic phases were combined, dried over anhydrous sodium sulfate, filtrated, concentrated. The crude product was separated and purified by silica gel column chromatography (petroleum ether:ethyl acetate=3:1) to obtain the title compound as colorless oil (0.8 g, yield 61.5%).

(2) Preparation of tert-butyl 8-amino-3-azabicyclo[3.2.1]octane-3-carboxylate

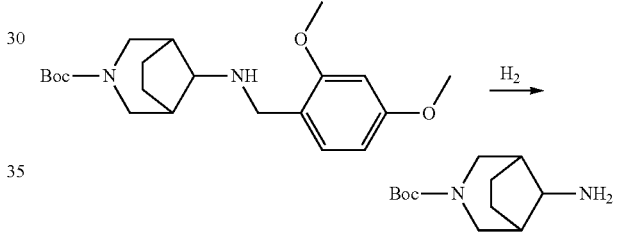

Tert-butyl 8-(2,4-dimethoxybenzylamino)-3-azabicyclo[3.2.1]octane-3-carboxylate (0.8 g, 2.12 mmol) was dissolved in methanol (10 mL), and Pd/C (0.1 g) was added. The reaction system was stirred and reacted at 25° C. under compressed hydrogen gas for 16 h, filtered, and the filtrate was concentrated in vacuum to obtain the title compound as colorless oil (0.46 g, yield 95.8%).

(3) Preparation of tert-butyl 8-((2S,5R)-6-(benzyloxy)-7-oxo-1,6-diazabicyclo[3.2.1]octane-2-carboxamido)-3-azabicyclo[3.2.1]octane-3-carboxylate

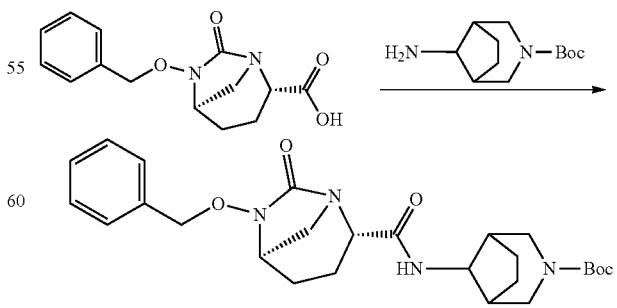

(2S,5R)-6-(benzyloxy)-7-oxo-1,6-diazabicyclo[3.2.1]octane-2-carboxylic acid (0.56 g, 2.03 mmol), tert-butyl 8-amino-3-azabicyclo[3.2.1]octane-3-carboxylate (0.46 g, 2.03 mmol), 1-hydroxylbenzotriazole (0.3 g, 2.22 mmol), 1-ethyl-(3-dimethylaminopropyl)carbodiimide hydrochloride (0.8 g, 4.17 mmol) and triethylamine (0.4 g, 3.9 mmol) were dissolved in dichloromethane (10 mL), stirred and reacted under nitrogen gas protection at 25° C. for 16 h. The reaction solution was concentrated, and the obtained crude product was separated and purified by silica gel column chromatography (petroleum ether:ethyl acetate=1:1) to obtain the title compound as a colorless gum (0.52 g, yield 53.1%).

(4) Preparation of tert-butyl 8-((2S,5R)-6-hydroxyl-7-oxo-1,6-diazabicyclo[3.2.1]octane-2-carboxamido)-3-azabicyclo[3.2.1]octane-3-carboxylate

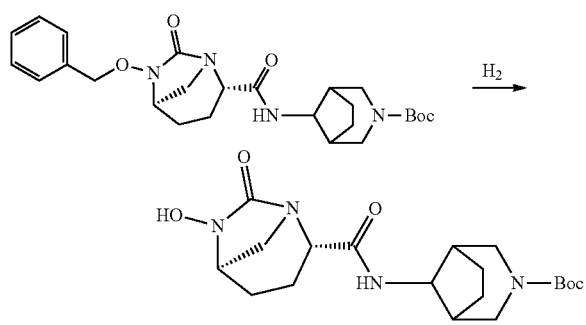

Tert-butyl 8-((2S,5R)-6-(benzyloxy)-7-oxo-1,6-diazabicyclo[3.2.1]octane-2-carboxamido)-3-azabicyclo[3.2.1]octane-3-carboxylate (0.5 g, 1.03 mmol) was dissolved in methanol (10 mL), and Pd/C (50 mg) was added. The reaction system was stirred and reacted at 25° C. under compressed hydrogen gas for 16 h, filtrated, and the filtrate was concentrated in vacuum to obtain the title compound in colorless form (0.37 g, yield 90.2%).

(5) Preparation of tert-butyl 8-((2S,5R)-7-oxo-6-(sulfoxy)-1,6-diazabicyclo[3.2.1]octane-2-carboxamido)-3-azabicyclo[3.2.1]octane-3-carboxylate

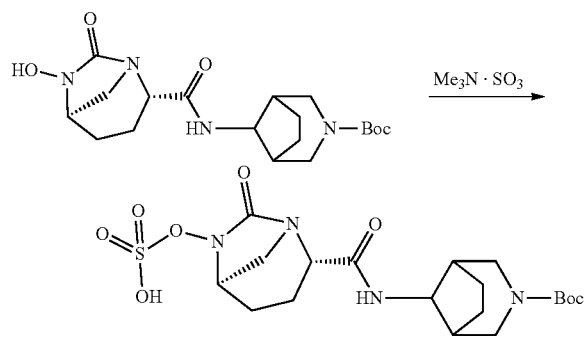

Tert-butyl 8-((2S,5R)-6-hydroxyl-7-oxo-1,6-diazabicyclo[3.2.1]octane-2-formamido)-3-azabicyclo[3.2.1]octane-3-carboxylate (0.37 g, 0.94 mmol) was dissolved in isopropanol (3 mL) and water (3 mL), and then triethylamine (25 mg, 0.25 mmol) and sulfur trioxide-trimethylamine complex (0.15 g, 1.08 mmol) were added. The reaction system was stirred and reacted at 25° C. for 16 h. Ethyl acetate (10 mL) and water (10 mL) were added, after stirring, the phases were separated. To the aqueous phase was added Bu₄NHSO₄ (0.33 g, 0.97 mmol), and the aqueous phase was extracted with dichloromethane (10 mL×3). The organic phases were combined, dried over anhydrous sodium sulfate, filtrated, and concentrated to obtain the title compound in colorless form (0.42 g, yield 95.4%).

(6) Preparation of (2S,5R)-2-((3-azabicyclo[3.2.1]octan-8-yl)carbamoyl)-7-oxo-1,6-diazabicyclo[3.2.1]octan-6-yl hydrogen sulfate (Compound 5)

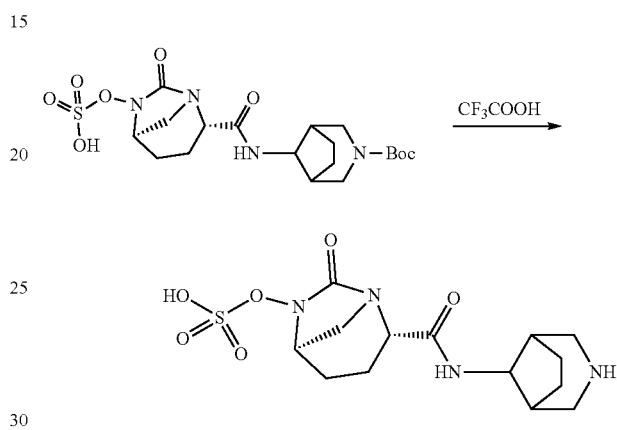

Tert-butyl 8-((2S,5R)-7-oxo-6-(sulfooxy)-1,6-diazabicyclo[3.2.1]octane-2-carboxamido)-3-azabicyclo[3.2.1]octane-3-carboxylate (0.42 g, 0.88 mmol) was dissolved in dichloromethane (5 mL), and then trifluoroacetic acid (1 mL) was added. The reaction solution was stirred and reacted at 25° C. for 1 h, concentrated, and acetone (10 mL) was added. The reaction solution was stirred for 10 min, and the solution of sodium iso-octoate in acetone was added. The reaction system was regulated to have pH of 5, stirred for 10 min, filtrated, and the obtained filter cake was separated and purified by Combiflash automatic rapid purification chromatography (mobile phase was water) to obtain the title compound in white color form (30 mg, yield 9.1%).

Molecular Formula: $C_{14}H_{22}N_4O_6S$ Molecular Weight: 374.4 LC-MS (m/z): 375.1 [M+H]⁺

¹H-NMR (400 MHz, MeOD) δ: 4.43 (d, J=13.6 Hz, 1H), 4.17 (s, 1H), 4.09 (d, J=6.4 Hz, 1H), 3.85-3.83 (m, 1H), 3.59 (d, J=13.2 Hz, 1H), 3.08-3.02 (m, 3H), 2.59-2.55 (m, 2H), 2.25-2.20 (m, 1H), 2.09-2.06 (m, 4H), 1.95-1.81 (m, 4H).

Example 6: Preparation of sodium (2S,5R)-2-((2-methyl-2-azaspiro[3.3]heptan-6-yl)carbamoyl)-7-oxo-1,6-diazabicyclo[3.2.1]octan-6-yl sulfate (sodium salt of Compound 6) (Method I)

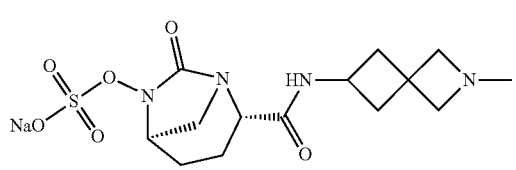

(1) Preparation of tert-butyl (2-methyl-2-azaspiro[3,3]heptan-6-yl)carbamate

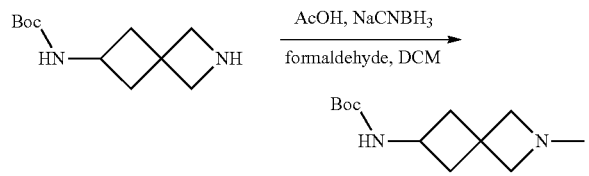

Tert-butyl 2-azaspiro[3.3]heptan-6-ylcarbamate (1 g, 4.71 mmol) was dissolved in dichloromethane (20 mL), added at 0° C. with formaldehyde aqueous solution (mass fraction 40%, 1.9 g, 63.28 mmol), acetic acid (141 mg, 2.35 mmol) and sodium cyanoborohydride (592 mg, 9.42 mmol). After addition of materials, the reaction solution was stirred at room temperature for 2 h, diluted by adding dichloromethane (30 mL), washed with water (30 mL×3), dried over anhydrous sodium sulfate, concentrated in vacuum, the crude product was purified by silica gel column chromatography (dichloromethane:methanol=50:1 to 10:1) to obtain the title compound as a white solid (900 mg, yield 84.0%).

(2) Preparation of 2-methyl-2-azaspiro[3.3]heptane-6-amine hydrochloride

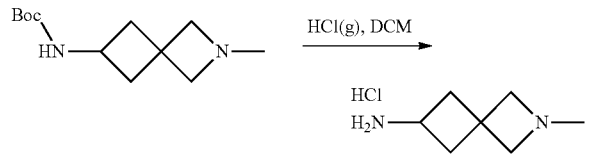

Tert-butyl (2-methyl-2-azaspiro[3.3]heptan-6-yl) carbamate (900 mg, 3.98 mmol) was dissolved in dichloromethane (30 mL), purged with hydrogen chloride gas for 30 min. The reaction solution was stirred at room temperature for 2 h, concentrated in vacuum to obtain the title compound as a white solid (600 mg crude product).

(3) Preparation of (2S,5R)-6-(benzyloxy)-N-(2-methyl-2-azaspiro[3.3]heptan-6-yl)-7-oxo-1,6-diazabicyclo[3.2.1]octane-2-carboxamide

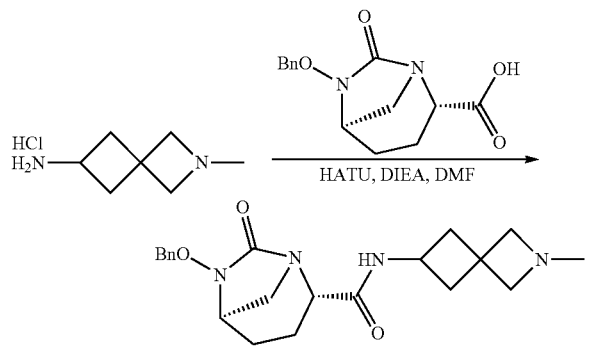

(2S,5R)-6-(benzyloxy)-7-oxo-1,6-diazabicyclo[3.2.1]octane-2-carboxylic acid (1.2 g, 4.34 mmol) was dissolved in N,N-dimethylformamide (30 mL), 2-(7-azabenzotriazole)-N,N,N',N'-tetramethylurea hexafluorophosphate (2.11 g, 5.55 mmol) and N,N-diisopropylethylamine (1.7 g, 13.15 mmol) were added, stirred at room temperature for 0.5 h, 2-methyl-2-azaspiro[3.3]heptane-6-amine hydrochloride (600 mg, 3.69 mmol) was added, stirred at room temperature overnight, diluted by adding ethyl acetate (50 mL), washed with water (30 mL×3), the organic phase was dried over anhydrous sodium sulfate, concentrated, the crude product was purified by silica gel column chromatography (dichloromethane:methanol=50:1-5:1) to obtain the title compound as a white solid (400 mg, yield 26.0%).

(4) Preparation of trimethylammonium (2S,5R)-2-((2-methyl-2-azaspiro[3.3]heptan-6-yl)carbamoyl)-7-oxo-1,6-diazabicyclo[3.2.1]octan-6-yl sulfate

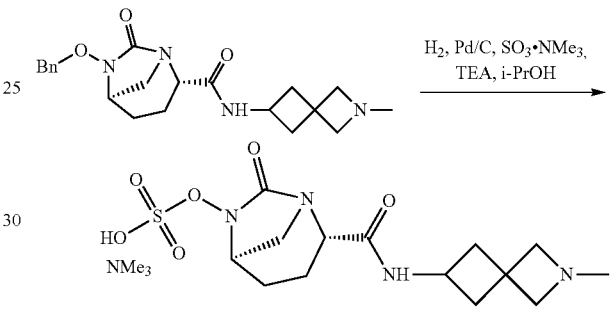

(2S,5R)-6-(benzyloxy)-N-(2-methyl-2-azaspiro[3.3]heptan-6-yl)-7-oxo-1,6-diazabicyclo[3.2.1]octane-2-carboxamide (350 mg, 0.91 mmol) was dissolved in a mixture solvent of isopropanol and water (1:1, 15 mL), triethylamine (275 mg, 2.72 mmol) sulfur trioxide-trimethylamine complex (253 mg, 1.81 mmol) and Pd/C (80 mg) are added, the system was vacuumed and purged with nitrogen gas for 3 times, then purged with hydrogen gas, stirred at room temperature for 1.5 h. Filtration was performed to remove catalyst, the filtrate was separated by high performance liquid chromatography to obtain the title compound as a white solid (100 mg, yield 25%).

(5) Preparation of sodium (2S,5R)-2-((2-methyl-2-azaspiro[3.3]heptan-6-yl) carbamoyl)-7-oxo-1,6-diazabicyclo[3.2.1]octan-6-yl sulfate

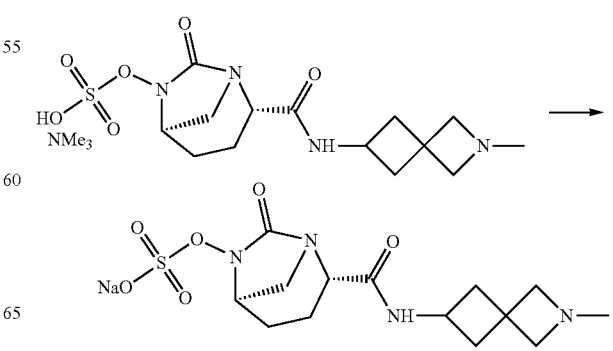

Trimethylammonium (2S,5R)-2-((2-methyl-2-azaspiro[3.3]heptan-6-yl) carbamoyl)-7-oxo-1,6-diazabicyclo[3.2.1]octan-6-yl sulfate (100 mg, 0.23 mmol) was dissolved in methanol (5 mL), sodium iso-octoate (191 mg, 1.15 mmol) was added. After addition, stirred at room temperature overnight, the crude product was separated by preparative high-performance liquid chromatography to obtain the title compound as a white solid (15 mg, yield 16%).

Molecular Formula: $C_{15}H_{21}N_4NaO_6S$ Molecular Weight: 396.4 LC-MS (m/z): 375[M+H]$^+$ $^1$H-NMR (300 MHz, DMSO-d$_6$) δ: 4.69-3.78 (m, 7H), 3.41-3.16 (m, 1H), 2.93 (d, J=12.6 Hz, 1H), 2.79 (s, 3H), 2.64-2.53 (m, 2H), 2.35-2.23 (m, 2H), 2.10-1.95 (m, 2H), 1.87-1.68 (m, 2H).

Example 6: Preparation of sodium (2S,5R)-2-((2-methyl-2-azaspiro[33]heptan-6-yl) carbamoyl)-7-oxo-1,6-diazabicyclo[3.2.1]octan-6-yl hydrogen sulfate (Compound 6) (Method II)

(1) Preparation of sodium (2S,5R)-2-((2-methyl-2-azaspiro[3.3]heptan-6-yl) carbamoyl)-7-oxo-1,6-diazabicyclo[3.2.1]octan-6-yl hydrogen sulfate

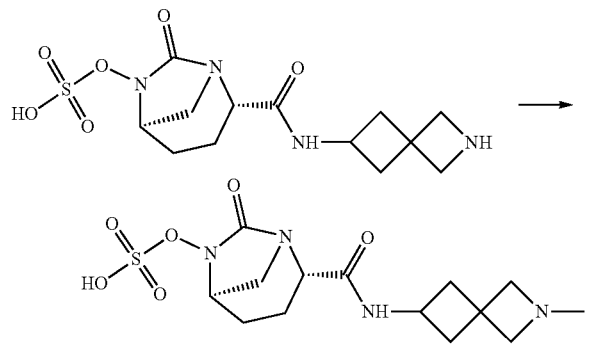

(2S,5R)-2-((2-azaspiro[3.3]heptan-6-yl) carbamoyl)-7-oxo-1,6-diazabicyclo[3.2.1]octan-6-yl hydrogen sulfate (46.0 g, 0.127 mol, its preparation method could be referred to Example 2) was added to water (460 mL), and to this system, an aqueous solution of formaldehyde (51.53 g, 0.635 mol), methanol (65 mL) and Pd/C (4.6 g) were added, the system was purged with hydrogen gas for 3 times, and reacted at 25° C. for 48 h, the completion of reaction was determined by analyzing raw materials with HPLC. The reaction solution was filtrated, the filtrate was concentrated to have a residue of about 90 mL, and the filtrate was then dropped into isopropanol (1380 mL) to precipitate solid, after filtration, the filter cake was washed with anhydrous methanol (100 mL) to obtain the title compound (26 g, yield was 54.4%).

Molecular formula $C_{14}H_{22}N_4O_6S$ Molecular weight: 374.4 LC-MS (M/e): 375.2 (M+H$^+$)

The title compound was processed to obtain an aqueous solution of 5 mg/ml, and the specific rotation of the title compound was determined to be −46±−2° according to the Optical Rotation Determination Method 0621 as described in the General Rule of the Chinese Pharmacopoeia 2015 edition.

$^1$H-NMR (400 MHz, D$_2$O) δ: 4.34-4.37 (d, J=12.0 Hz, 1H), 4.20-4.23 (d, J=12.0 Hz, 1H), 4.10-4.14 (m, 2H), 4.0-4.03 (d, J=12 Hz, 1H), 3.88-3.95 (m, 2H), 3.19-3.22 (d, J=12.0 Hz, 1H), 2.92-2.95 (d, J=14.0 Hz, 1H), 2.78 (s, 3H), 2.58-2.62 (m, 2H), 2.21-2.27 (m, 2H), 1.93-2.10 (m, 2H), 1.75-1.82 (m, 1H), 1.66-1.70 (m, 1H).

Example 6-A: Preparation of (2R,5R)-2-((2-methyl-2-azaspiro[3.3]heptan-6-yl) carbamoyl)-7-oxo-1,6-diazabicyclo[3,2,1]octan-6-yl hydrogen sulfate (Compound 6-2)

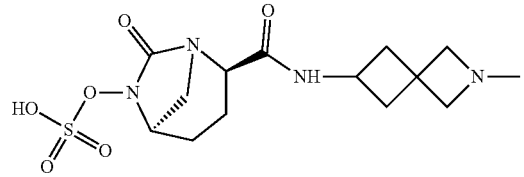 [SMILES: CN1CC2(CC(NC(=O)[C@H]3CC[C@@H]4CN3C(=O)N4OS(=O)(=O)O)C2)C1]

(1) Preparation of (2R,5R)-2-((2-azaspiro[3.3]heptan-6-yl)carbamoyl)-7-oxo-1,6-diazabicyclo[3.2.1]octan-6-yl hydrogen sulfate The method for preparing this compound could be referred to Example 2-A, and the title compound was finally obtained (60 mg, yield 72.3%).

(2) Preparation of (2R,5R)-2-((2-methyl-2-azaspiro[3,3]heptan-6-yl)carbamoyl)-7-oxo-1,6-diazabicyclo[3,2,1]octan-6-yl hydrogen sulfate

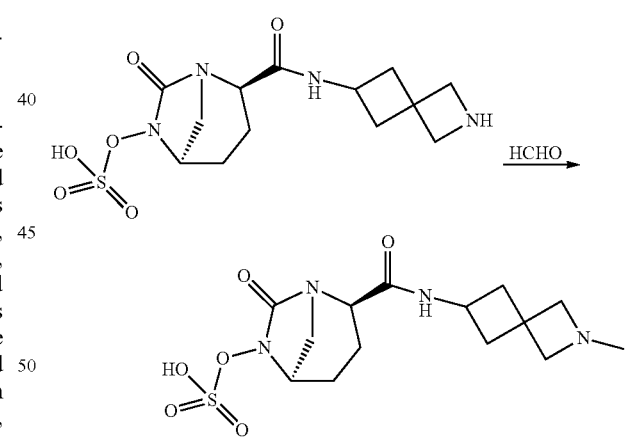

(2R,5R)-2-((2-azaspiro[3,3]heptan-6-yl)carbamoyl)-7-oxo-1,6-diazabicyclo[3,2,1]octan-6-yl hydrogen sulfate (50 mg, 0.139 mmol) was dissolved in a mixture solvent of water (50 mL) and methanol (3 mL), then to the system was added an aqueous solution of formaldehyde (0.5 mL, 37%), Pd/C (20 mg), purged with hydrogen at 25° C. for 16 h, distilled to remove methanol, the residue was purified with reverse phase silica gel column chromatography (acetonitrile/water=09%-20%) to obtain the title compound (9 mg, yield 17.3%).

Molecular Formula: $C_{14}H_{22}N_4O_6S$ Molecular weight: 374.41 LC-MS (m/z): 375.1 (M+H$^+$)

Example 7: Preparation of sodium (2S,5R)-2-((2-ethyl-2-azaspiro[3.3]heptan-6-yl) carbamoyl)-7-oxo-1,6-diazabicyclo[3.2.1]octan-6-yl sulfate (Compound 7)

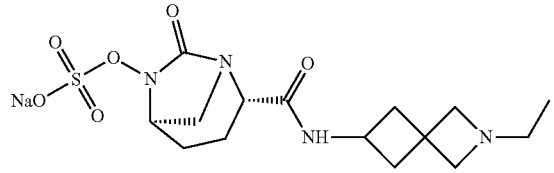

(1) Preparation of tert-butyl (2-ethyl-2-azaspiro[3.3]heptan-6-yl)carbamate

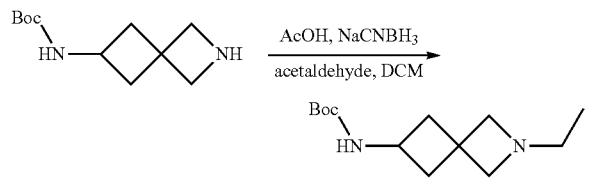

Tert-butyl 2-azaspiro[3.3]heptan-6-ylcarbamate (900 mg, 4.24 mmol) was dissolved in dichloromethane (30 mL), acetaldehyde aqueous solution (mass fraction 40%, 2.3 g, 52.21 mmol) and acetic acid (127 mg, 2.11 mmol) were added at 0° C. Sodium cyanoborohydride (534 mg, 8.50 mmol) was added in batches. After addition of materials, the reaction solution was stirred at room temperature for 2 h, diluted by adding dichloromethane (30 mL), washed with water (30 mL×3), dried over anhydrous sodium sulfate, concentrated in vacuum, the crude product was purified by silica gel column chromatography (dichloromethane:methanol=50:1-10:1) to obtain the title compound as a white solid (800 mg, yield 78.6%).

(2) Preparation of 2-ethyl-2-azaspiro[3.3]heptane-6-amine hydrochloride

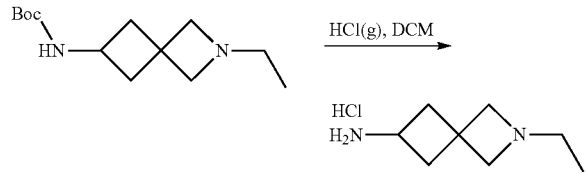

Tert-butyl (2-ethyl-2-azaspiro[3.3]heptan-6-yl)carbamate (800 mg, 3.33 mmol) was dissolved in dichloromethane (15 mL), purged with hydrogen chloride gas, the reaction solution was stirred at room temperature for 2 h, concentrated in vacuum to the title compound as a white solid (480 mg crude product).

(3) Preparation of (2S,5R)-6-(benzyloxy)-N-(2-ethyl-2-azaspiro[3.3]heptan-6-yl)-7-oxo-1,6-diazabicyclo[3.2.1]octane-2-carboxamide

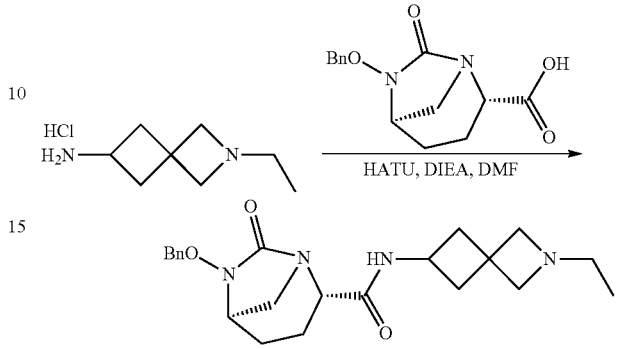

(2S,5R)-6-(benzyloxy)-7-oxo-1,6-diazabicyclo[3.2.1]octane-2-carboxylic acid (828 mg, 3.00 mmol) was dissolved in N,N-dimethylformamide (30 mL), N,N-diisopropylethylamine (990 mg, 7.66 mmol) and 2-(7-azobenzotriazole)-N,N,N',N'-tetramethylurea hexafluorophosphate (1.46 g, 3.84 mmol) were added, stirred at room temperature for 0.5 h, 2-ethyl-2-azaspiro[3.3]heptane-6-amine hydrochloride (480 mg, 2.72 mmol) was added, stirred at room temperature overnight, diluted by adding ethyl acetate (50 mL), washed with water (30 mL×3), the organic phase was dried over anhydrous sodium sulfate, concentrated in vacuum, the crude product was purified by silica gel column chromatography (dichloromethane:methanol=50:1-5:1) to obtain the title compound as a white solid (300 mg, yield 27.7%).

(4) Preparation of trimethylammonium (2S,5R)-2-((2-ethyl-2-azaspiro[3.3]heptan-6-yl) carbamoyl)-7-oxo-1,6-diazabicyclo[3.2.1]octan-6-yl sulfate

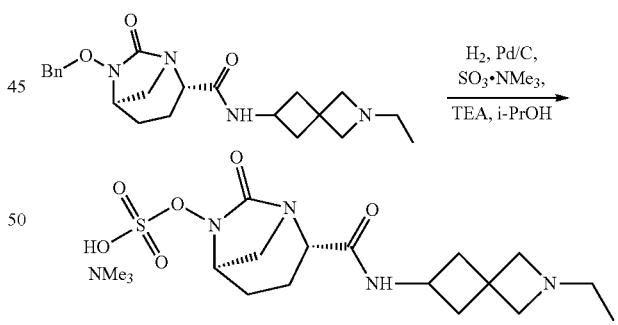

(2S,5R)-6-(benzyloxy)-N-(2-ethyl-2-azaspiro[3.3]heptan-6-yl)-7-oxo-1,6-diazabicyclo[3.2.1]octane-2-carboxamide (300 mg, 0.75 mmol) was dissolved in a mixture solution of isopropanol and water (1:1, 10 mL), triethylamine (227 mg, 2.25 mmol), sulfur trioxide-trimethylamine complex (208 mg, 1.49 mmol) and Pd/C (50 mg) were added, the system was vacuumed and purged with nitrogen gas for 3 times, then purged with hydrogen gas, stirred at room temperature for 1.5 h. Suck filtration was performed to remove catalyst, the filtrate was separated by preparative high-performance liquid chromatography to obtain the title compound as a white solid (50 mg, yield 15%).

(5) Preparation of sodium (2S,5R)-2-((2-ethyl-2-azaspiro[3.3]heptan-6-yl) carbamoyl)-7-oxo-1,6-diazabicyclo[3.2.1]octan-6-yl sulfate

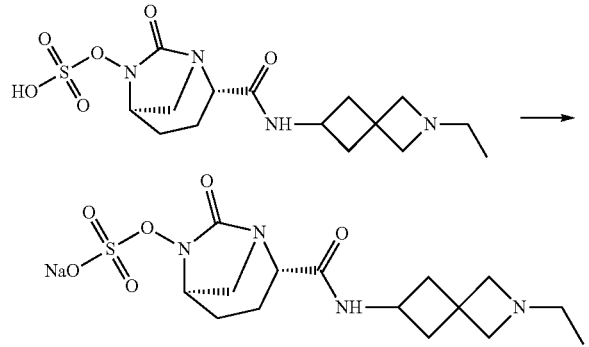

Trimethylammonium (2S,5R)-2-((2-ethyl-2-azaspiro[3.3]heptan-6-yl) carbamoyl)-7-oxo-1,6-diazabicyclo[3.2.1]octan-6-yl sulfate (50 mg, 0.11 mmol) was dissolved in methanol (5 mL), sodium iso-octoate (93 mg, 0.56 mmol) was added. After addition, stirred at room temperature for 24 h, the crude product was separated by preparative high-performance liquid chromatography to obtain the title compound as a white solid (3 mg, yield 7%).

Molecular Formula: $C_{15}H_{23}N_4NaO_6S$ Molecular Weight: 410.4 LC-MS (m/z): 389[M+H]$^+$ $^1$H-NMR (300 MHz, D$_2$O) δ: 4.17-3.88 (m, 6H), 3.20-3.15 (m, 1H), 3.05-1.90 (m, 3H), 2.60-2.40 (m, 2H), 2.27-2.20 (m, 2H), 2.04-1.94 (m, 2H), 1.84-1.70 (m, 2H), 1.10-1.00 (m, 3H).

Example 8: Preparation of sodium (2S,5R)-2-((2-acetyl-2-azaspiro[3.3]heptan-6-yl) carbamoyl)-7-oxo-1,6-diazabicyclo[3.2.1]octan-6-yl sulfate (Compound 8)

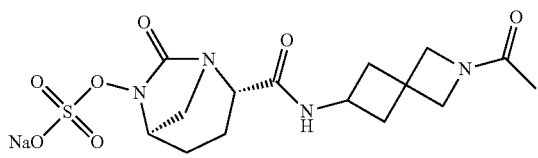

(1) Preparation of (2S,5R)—N-(2-acetyl-2-azaspiro[3.3]heptan-6-yl)-6-(benzyloxy)-7-oxo-1,6-diazabicyclo[3.2.1]octane-2-carboxamide

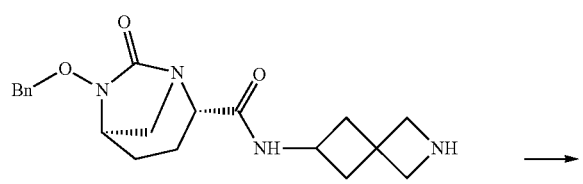

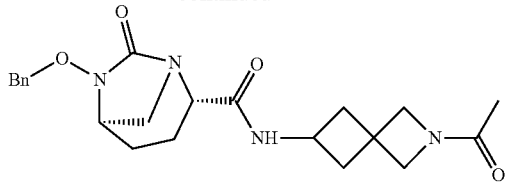

The reaction crude product was dissolved in dichloromethane (20 mL), acetic anhydride (0.2 mL) and triethylamine (710 mg, 7.0 mmol) were added at 25° C., stirred and reacted for 4.0 h. After completion of the reaction as measured by LC-MS, vacuum concentration was performed, the crude product was purified by silica gel column chromatography (dichloromethane:methanol=50:1-30:1) to obtain the title compound as oil (890 mg, yield 89.1%).

(2) Preparation of tetra(n-butyl)ammonium (2S,5R)-2-((2-acetyl-2-azaspiro[3.3]heptan-6-yl) carbamoyl)-7-oxo-1,6-diazabicyclo[3.2.1]octan-6-yl sulfate (2S,5R)—N-(2-acetyl-2-azaspiro[3.3]heptan-6-yl)-6-(benzyloxy)-7-oxo-1,6-diazabicyclo[3.2.1]octane-2-carboxamide (0.89 g, 2.16 mmol) was dissolved in a mixture solvent of isopropanol (20 mL) and water (20 mL), Pd/C (89 mg, mass fraction 10%), sulfur trioxide-trimethylamine complex (361 mg, 2.59 mmol) and triethylamine (54.6 mg, 0.54 mmol) were serially added, purged with hydrogen gas, stirred at 25° C. for 16 h. After completion of the reaction as measured by LC-MS, suck filtration was performed, the filtrate was concentrated, water (50 mL) and ethyl acetate (100 mL) were added, the phases were separated to obtain the aqueous phase, tetrabutylammonium hydrogen sulfate (807 mg, 2.38 mmol) was added, stirred at 25° C. for 0.5 h, then dichloromethane (100 mL) was added, the phases were separated to obtain the organic phase, which was dried over anhydrous sodium sulfate, suck filtrated, the filtrate was concentrated to obtain the title compound in white color (1.2 g, yield 86.3%).

(3) Preparation of sodium (2S,5R)-2-((2-acetyl-2-azaspiro[3.3]heptan-6-yl) carbamoyl)-7-oxo-1,6-dizabicylco[3.2.1]octan-6-yl sulfate

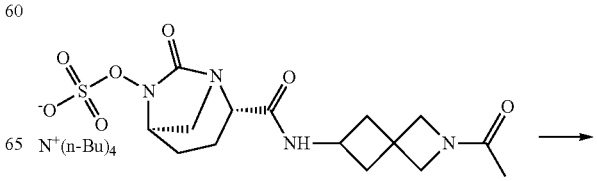

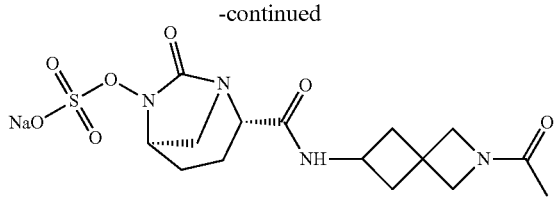

Tetra(n-butyl)ammonium (2S,5R)-2-((2-acetyl-2-azaspiro[3.3]heptan-6-yl) carbamoyl)-7-oxo-1,6-diazabicyclo[3.2.1]octan-6-yl sulfate (0.2 g, 0.31 mmol) was dissolved in a mixture solvent of isobutanol (5 mL) and water (0.05 mL), sodium iso-octoate (103 mg, 0.62 mmol) was added under stirring, stirred at 25° C. for 2.0 h, concentrated in vacuum, isobutanol (1 mL) was added, shaken under ultrasonic, suck filtrated to obtain white solid, the solid was dissolved in methanol (5 mL), concentrated, separated by reversed-phase preparative chromatography (acetonitrile:water=0~37%) to obtain the title compound in white color (30 mg, 22.8%).

Molecular Formula: $C_{15}H_{21}N_4NaO_7S$ Molecular Weight: 424.4 LC-MS (m/z): 403.1 [M+H]$^+$ $^1$H-NMR (400 MHz, D$_2$O) δ: 4.25 (s, 1H), 4.15-4.11 (m, 3H), 4.00 (s, 1H), 3.93-3.88 (m, 2H), 3.27-3.22 (m, 1H), 2.97 (d, J=12.4 Hz, 1H), 2.58-2.52 (m, 2H), 2.22-2.17 (m, 2H), 2.12-1.97 (m, 2H), 1.84-1.70 (m, 5H).

Example 9: Preparation of (2S,5R)-2-((2-(methylsulfonyl)-2-azaspiro[3.3]heptan-6-yl) carbamoyl)-7-oxo-1,6-diazabicyclo[3.2.1]octan-6-yl hydrogen sulfate (Compound 9)

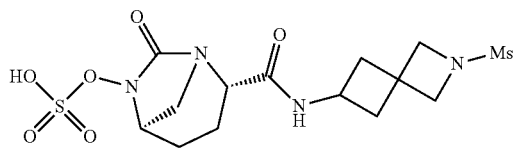 [SMILES: CS(=O)(=O)N1CC2(CC(NC(=O)[C@@H]3CC[C@@H]4CN3C(=O)N4OS(=O)(=O)O)C2)C1]

(1) Preparation of (2S,5R)-6-(benzyloxy)-N-(2-(methylsulfonyl)-2-azaspiro[3.3]heptan-6-yl)-7-oxo-1,6-diazabicyclo[3.2.1]octane-2-carboxamide

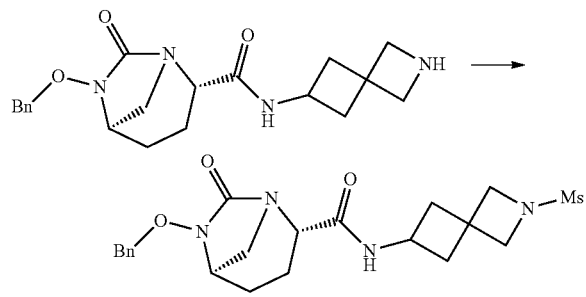

(2S,5R)-6-(benzyloxy)-7-oxo-N-(2-azaspiro[3.3]heptan-6-yl)-1,6-diazabicyclo[3.2.1]octane-2-carboxamide and triethylamine (773 mg, 7.65 mmol) were added to dichloromethane (16 mL), cooled to 0° C., methylsulfonyl chloride (436 mg, 3.82 mmol) was slowly added dropwise, after addition dropwise, heated to 25° C. and stirred for 2 h. After completion of the reaction, water (100 mL) and dichloromethane (100 mL) were added, layered to obtain the organic phase, concentrated, and purified by silica gel column chromatography (petroleum ether:ethyl acetate=4:1-1:1) to obtain the title compound (750 mg, two-step yield 65.8%).

(2) Preparation of (2S,5R)-6-hydroxyl-N-(2-(methylsulfonyl)-2-azaspiro[3.3]heptan-6-yl)-7-oxo-1,6-diazabicyclo[3.2.1]octane-2-carboxamide

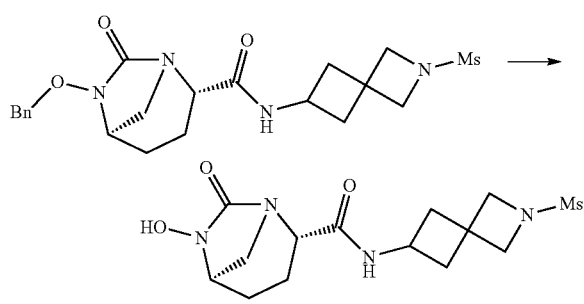

(2S,5R)-6-(benzyloxy)-N-(2-(methylsulfonyl)-2-azaspiro[3.3]heptan-6-yl)-7-oxo-1,6-diazabicyclo[3.2.1]octane-2-carboxamide (400 mg, 0.9 mmol) was dissolved in methanol (30 mL), Pd/C (40 mg, 10% w/w) was added, purged with hydrogen gas, stirred at 25° C. for 16 h. After completion of the reaction, suck filtration was performed, the filtrate was distilled to dryness to obtain the title compound, which was directly used in the next step without purification.

(3) Preparation of (2S,5R)-2-((2-(methylsulfonyl)-2-azaspiro[3.3]heptan-6-yl) carbamoyl)-7-oxo-1,6-diazabicyclo[3.2.1]octan-6-yl hydrogen sulfate

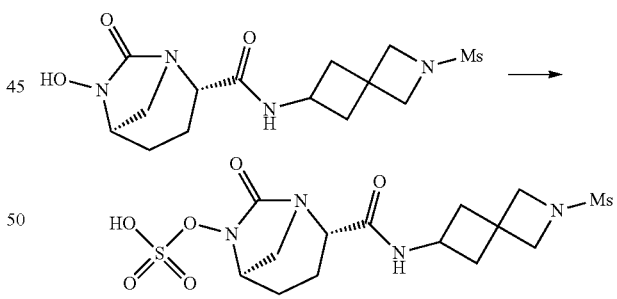

The product (2S,5R)-6-hydroxyl-N-(2-(methylsulfonyl)-2-azaspiro[3.3]heptan-6-yl)-7-oxo-1,6-diazabicyclo[3.2.1]octane-2-carboxamide from the previous step was dissolved in a mixture solvent of isopropanol (20 mL) and water (20 mL), sulfur trioxide-trimethylamine complex (150 mg, 1.08 mmol) and triethylamine (23 mg, 0.23 mmol) were added, stirred at 25° C. for 16 h. After completion of the reaction, water (50 mL) and ethyl acetate (100 mL) were added, layered to obtain the aqueous phase, to the aqueous phase was added tetrabutylammonium hydrogen sulfate (340 mg, 1.0 mmol), stirred at 25° C. for 20 min, then dichloromethane (100 mL) was added, layers were separated to obtain the organic phase, the aqueous phase was extracted with dichloromethane (50 mL×2), the organic phases were combined, dried over anhydrous sodium sulfate, suck filtrated, the filtrate was distilled to dryness to obtain the title compound in white crude product form. The crude product was dissolved in a mixture solvent of isobutanol and water (100:1, 10 mL), sodium iso-octoate (300 mg, 1.8 mmol) was added, stirred at 25° C. for 2 h to precipitate white solid, filtered, the filter cake was dried to obtain the title compound (37 mg, two-step yield 9.4%).

Molecular Formula: $C_{14}H_{22}N_4O_8S_2$ Molecular Weight: 438.5 LC-MS (m/z): 437.1 [M+H]$^+$ $^1$H-NMR (400 MHz, $D_2O$) δ: 4.13-4.09 (m, 2H), 3.96 (s, 2H), 3.90-3.85 (m, 3H), 3.20 (d, J=11.6 Hz, 1H), 2.96-2.92 (m, 4H), 2.57-2.52 (m, 2H), 2.20-2.15 (m, 2H), 2.10-1.94 (m, 2H), 1.83-1.66 (m, 2H).

Example 10: Preparation of (2S,5R)-7-oxo-2-(spiro [3.3]heptan-2-ylcarbamoyl)-1,6-diazabicyclo[3.2.1] octan-6-yl hydrogen sulfate (Compound 10)

(1) Preparation of spiro[3.3]heptan-2-ol

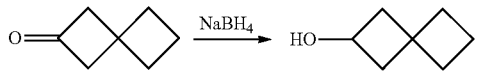

Spiro[3.3]heptan-2-one (1.1 g, 10 mmol) was added in methanol (50 mL), cooled with ice-bath, sodium borohydride (418 mg, 11 mmol) was slowly added in batches, then heated to 25° C. and reacted for 2 h. After completion of the reaction, vacuum concentration was performed, ethyl acetate (100 mL) was added, washed sequentially with water (30 mL) and saturated brine (30 mL), the organic phase was dried over anhydrous sodium sulfate, concentrated in vacuum to obtain colorless oil product (962 mg, yield 85.9%).

(2) Preparation of 2-(spiro[3.3]heptan-2-yl)isoindolin-1,3-dione

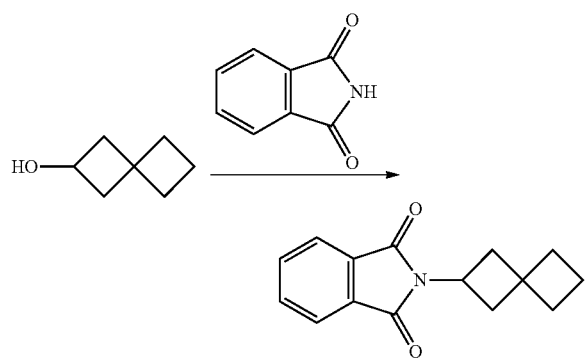

Spiro[3.3]heptan-2-ol (962 mg, 8.6 mmol), phthalimide (1.26 g, 8.6 mmol) and triphenylphosphine (4.51 g, 17.2 mmol) were dissolved in dry tetrahydrofuran (50 mL), protected with nitrogen gas, diethyl azodicarboxylate (3.0 g, 17.2 mmol) was added dropwise under ice-water bath. After addition, heated to 25° C. and reacted for 2 h, ethyl acetate (150 mL) was added, washed with saturated brine (100 mL), the organic phase was dried over anhydrous sodium sulfate, concentrated in vacuum, the crude product was purified by silica gel column chromatography (petroleum ether:ethyl acetate=5:1) to obtain product (1.56 g, yield 75.2%).

(3) Preparation of spiro[3.3]heptane-2-amine

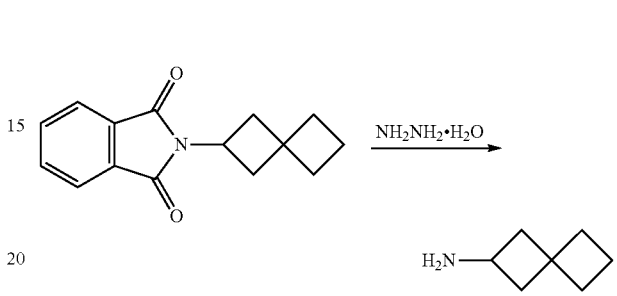

2-(spiro[3.3]heptan-2-yl)isoindolin-1,3-dione (1.56 g, 6.47 mmol) was dissolved in methanol (30 mL), hydrazine hydrate (1.88 g, 30 mmol, 80%) was added, reacted at 20° C. for 6 h. After completion of the reaction, the reaction solution was suck filtrated, concentrated in vacuum, ethyl acetate (150 mL) was added, washed with water (100 mL), the organic phase was dried over anhydrous sodium sulfate, concentrated in vacuum, the crude product was separated and purified by silica gel column chromatography (petroleum ether:ethyl acetate=3:1) to obtain product (561 mg, yield 78.1%).

(4) Preparation of (2S,5R)-6-(benzyl oxy)-7-oxo-N-(spiro[3.3]heptan-2-yl)-1,6-diazabicyclo[3.2.1]octane-2-carboxamide

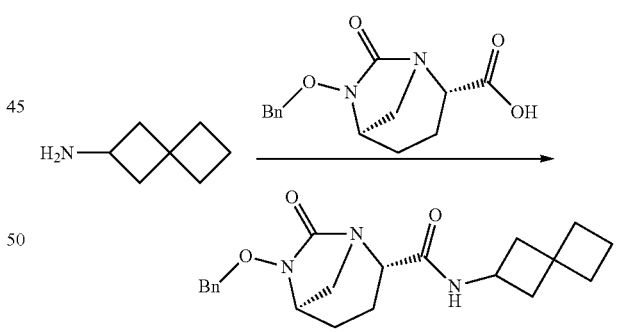

(2S,5R)-6-(benzyloxy)-7-oxo-1,6-diazabicyclo[3.2.1]octane-2-carboxylic acid (500 mg, 1.81 mmol), spiro[3.3]heptane-2-amine (201 mg, 1.81 mmol), 1-(3-dimethyl aminopropyl)-3-ethylcarbodiimide hydrochloride (384 mg, 2.0 mmol), 1-hydroxylbenzotriazole (270 mg, 2.0 mmol) and triethylamine (202 mg, 2.0 mmol) were dissolved in dichloromethane (30 mL), reacted at 20° C. for 2 h. After completion of the reaction, ethyl acetate (200 mL) was added, washed sequentially with a saturated solution of sodium hydrogen carbonate (100 mL) and saturated brine (100 mL), the organic phase was dried over anhydrous sodium sulfate, concentrated in vacuum, purified by column

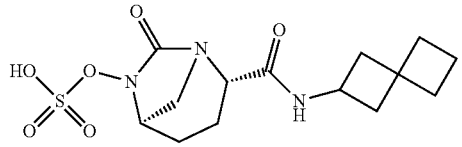 [SMILES: O=C(NC1CC2(CCC2)C1)[C@@H]1CC[C@@H]2CN1C(=O)N2OS(=O)(=O)O]

chromatography (petroleum ether:ethyl acetate=2:1) to obtain product (371 mg, yield 55.5%).

(5) Preparation of (2S,5R)-6-hydroxyl-7-oxo-N-(spiro[3.3]heptan-2-yl)-1,6-diazabicyclo[3.2.1]octane-2-carboxamide

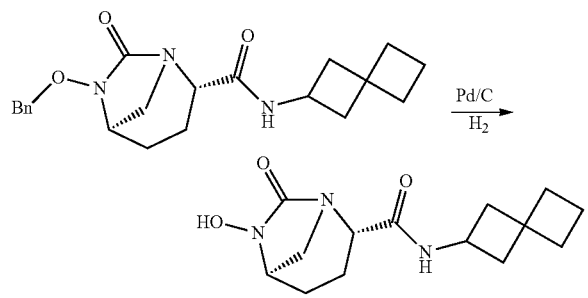

(2S,5R)-6-(benzyloxy)-7-oxo-N-(spiro[3.3]heptan-2-yl)-1,6-diazabicyclo[3.2.1]octane-2-carboxamide (371 mg, 1.0 mmol) was dissolved in methanol (15 mL), Pd/C catalyst (9.6 mg, 10%) was added, purged with hydrogen gas, reacted for 1 h. After reaction, suck filtration, vacuum concentration were performed to obtain colorless oil product (225 mg, yield 80.6%).

(6) Preparation of (2S,5R)-7-oxo-2-(spiro[3.3]heptan-2-ylcarbamoyl)-1,6-diazabicyclo[3.2.1]octan-6-yl hydrogen sulfate

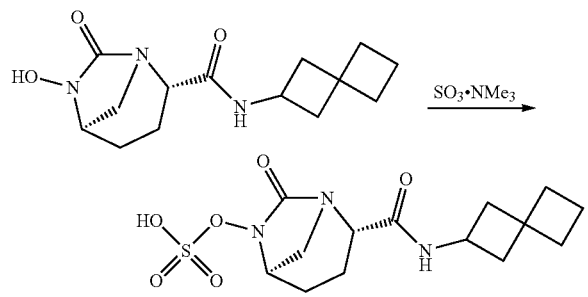

(2S,5R)-6-hydroxyl-7-oxo-N-(spiro[3.3]heptan-2-yl)-1,6-diazabicyclo[3.2.1]octane-2-carboxamide (225 mg, 0.81 mmol), sulfur trioxide-trimethylamine complex (125 mg, 0.90 mmol) were dissolved in a mixture solvent of isopropanol (15 mL) and water (15 mL), reacted at 25° C. for 12 h, water (50 mL) was added, washed with ethyl acetate (50 mL), to the aqueous phase was added tetrabutylammonium hydrogen sulfate (9.6 g, 60 mmol), reacted at 25° C. for 1 h, the aqueous phase was extracted with dichloromethane, the organic phase was dried, concentrated in vacuum, washed with acetonitrile (1 mL), suck filtrated to obtain product as a white solid (63 mg, yield 21.8%).

Molecular Formula: $C_{14}H_{21}N_3O_6S$ Molecular Weight: 359.4 LC-MS (m/z): 360.1 [M+H]+

$^1$H-NMR (400 MHz, D$_2$O) δ: 4.10-4.08 (m, 1H), 4.05-3.95 (m, 1H), 3.87-3.85 (m, 1H), 3.21-3.16 (m, 1H), 2.94-2.90 (m, 1H), 2.41-2.23 (m, 2H), 2.10-2.02 (m, 1H), 1.95-1.90 (m, 3H), 1.85-1.65 (m, 8H).

Example 11: Preparation of (2S,5R)-2-((6-aminospiro[3.3]heptan-2-yl) carbamoyl)-7-oxo-1,6-diazabicyclo[3.2.1]octan-6-yl hydrogen sulfate (Compound 11)

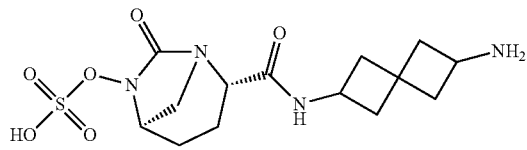 [SMILES: NC1CC2(C1)CC(NC(=O)[C@@H]1CC[C@@H]3CN1C(=O)N3OS(=O)(=O)O)C2]

(1) Preparation of tert-butyl (6-((2S,5R)-6-(benzyloxy)-7-oxo-1,6-diazabicyclo[3.2.1]octane-2-carboxamido)spiro[3.3]heptan-2-yl)carbamate

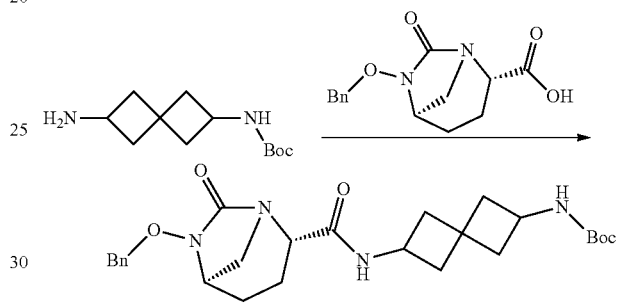

(2S,5R)-6-(benzyloxy)-7-oxo-1,6-diazabicyclo[3.2.1]octane-2-carboxylic acid (0.5 g, 1.8 mmol) and tert-butyl (6-azaspiro[3.3]heptan-2-yl)carbamate (0.5 g, 2.2 mmol) were dissolved in dichloromethane (50 mL), cooled under nitrogen gas protection to 0° C., 1-hydroxylbenzotriazole (0.4 g, 3.0 mmol), triethylamine (0.9 g, 8.9 mmol) and 1-ethyl-(3-dimethylaminopropyl)carbodiimide hydrochloride (0.7 g, 3.7 mmol) were added, heated to 25° C. and reacted for 16 h. After completion of the reaction, water (50 mL) and dichloromethane (50 mL) were added, the phases were separated to obtain an the organic phase, after concentration, the crude product was purified by silica gel column chromatography (petroleum ether:ethyl acetate=2:1) to obtain the title compound (0.4 g, yield 45.9%).

(2) Preparation of tert-butyl 6-((2S,5R)-6-hydroxyl-7-oxo-1,6-diazabicyclo[3.2.1]octane-2-carboxamido)spiro[3.3]heptan-2-yl)carbamate

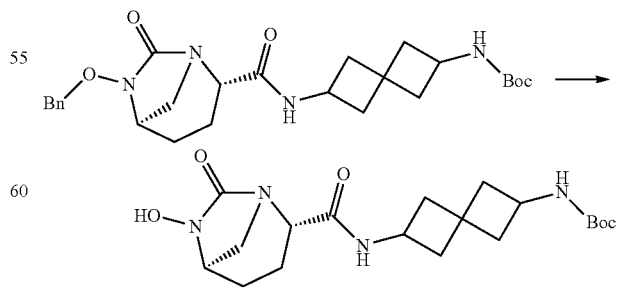

Tert-butyl (6-((2S,5R)-6-(benzyloxy)-7-oxo-1,6-diazabicyclo[3.2.1]octane-2-carboxamido)spiro[3.3]heptan-2-yl)carbamate (0.4 g, 0.83 mmol) was dissolved in methanol (30 mL), Pd/C (10%, 40 mg) was added, purged with hydrogen gas, reacted at 25° C. for 16 h. After completion of the reaction, the reaction solution was such filtrated, the filtrate was concentrated to obtain the title compound, which was directly used in the next reaction step without purification.

(3) Preparation of tetra(n-butyl)ammonium (2S,5R)-2-((6-(((tert-butoxycarbonyl)amino)spiro[3.3]heptan-2-yl)carbamoyl)-7-oxo-1,6-diazabicyclo[3.2.1]octan-6-yl sulfate

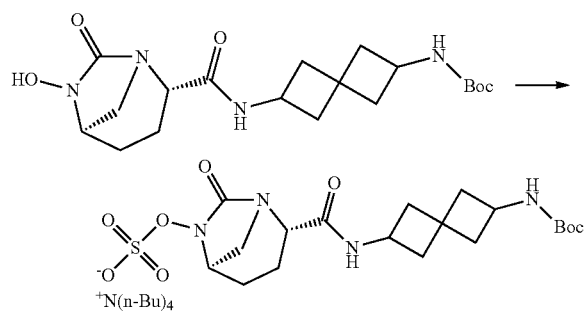

The product tert-butyl 6-((2S,5R)-6-hydroxyl-7-oxo-1,6-diazabicyclo[3.2.1]octane-2-carboxamido)spiro[3.3]heptan-2-yl)carbamate from the previous step was dissolved in a mixture solvent of isopropanol (20 mL) and water (20 mL), trimethylammonium-sulfur trioxide complex (0.2 g, 1.4 mmol) and triethylamine (30 mg, 0.3 mmol) were added, reacted at 25° C. for 16 h. After completion of the reaction, water (50 mL) ethyl acetate (100 mL) were added. After the phases were separated, the aqueous phase was obtained, to the aqueous phase was added tetrabutylammonium hydrogen sulfate (0.6 g, 1.77 mmol), stirred at 25° C. for 20 min, then dichloromethane (100 mL) was added, layered to obtain the organic phase, the aqueous phase was extracted with dichloromethane (50 mL×2), all the organic phases were combined, dried over anhydrous sodium sulfate, suck filtrated, the filtrate was concentrated to obtain the title compound, which was directly used in the next reaction step without purification.

(4) Preparation of (2S,5R)-2-((6-aminospiro[3.3]heptan-2-yl)carbamoyl)-7-oxo-1,6-diazabicyclo[3.2.1]octan-6-yl hydrogen sulfate

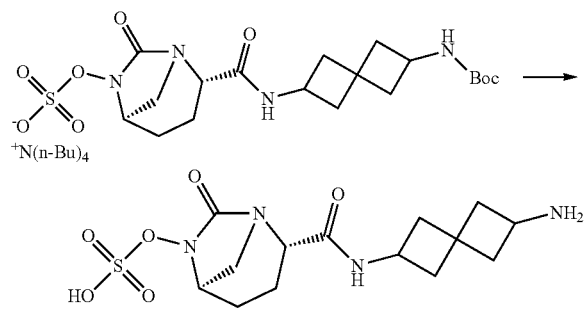

The product tetra(n-butyl)ammonium (2S,5R)-2-((6-((tert-butoxycarbonyl)amino)spiro[3.3]heptan-2-yl)carbamoyl)-7-oxo-1,6-diazabicyclo[3.2.1]octan-6-yl sulfate was dissolved in dichloromethane (20 mL), cooled to 0° C., trifluoroacetic acid (10 mL) was added, reacted at 0° C. for 0.5 h. After completion of the reaction, the crude product was obtained by vacuum concentration, the crude product was washed with acetonitrile (40 mL×3) to obtain the title compound (90 mg, yield over three steps 29.0%).

Molecular Formula: $C_{14}H_{22}N_4O_6S$ Molecular Weight: 374.4 LC-MS (m/z): 375.1 $[M+H]^+$ $^1$H-NMR (400 MHz, $D_2O$) δ: 4.12-4.10 (m, 2H), 3.90 (d, J=7.2 Hz, 1H), 3.70-3.60 (m, 1H), 3.20 (d, J=12.0 Hz, 1H), 2.95 (dd, $J_1$=12.0 Hz, $J_2$=10.4 Hz, 1H), 2.46-2.43 (m, 2H), 2.31-2.27 (m, 2H), 2.15-2.14 (m, 2H), 2.13-2.11 (m, 3H), 2.10-1.97 (m, 3H), 1.88-1.75 (m, 1H), 1.73-1.62 (m, 1H).

Example 12: Preparation of (2S,5R)-2-((2-butyl-2-azaspiro[3.3]heptan-6-yl) carbamoyl)-7-oxo-1,6-diazabicyclo[3.2.1]octan-6-yl hydrogen sulfate (Compound 12)

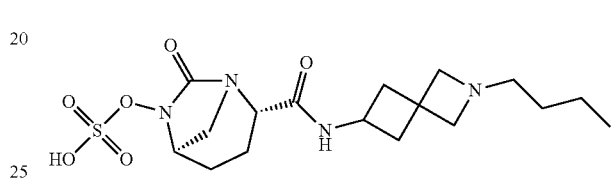

(1) Preparation of (2S,5R)-6-(benzyloxy)-N-(2-butyl-2-butyl-2-azaspiro[3.3]heptan-6-yl)-7-oxo-1,6-diazabicyclo[3.2.1]octane-2-carboxamide

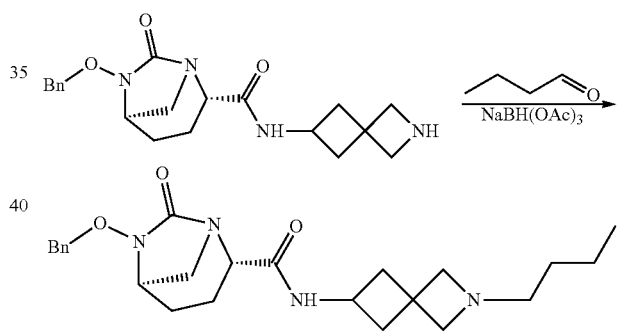

The reaction crude product was dissolved in tetrahydrofuran (20 mL), added at 0° C. with butyraldehyde (0.67 g, 9.3 mmol), stirred and reacted for 1 h, sodium triacetyloxyborohydride (1.97 g, 9.3 mmol) was added, stirred for 0.5 h. After completion of the reaction as measured by LC-MS, concentrated in vacuum, the crude product was purified by silica gel column chromatography (dichloromethane:methanol=50:1-10:1) to obtain the title compound as oil (550 mg, yield over two steps 55.0%).

(2) Preparation of (2S,5R)—N-(2-butyl-2-azaspiro[3.3]heptan-6-yl)-6-hydroxyl-7-oxo-1,6-diazabicyclo[3.2.1]octane-2-carboxamide

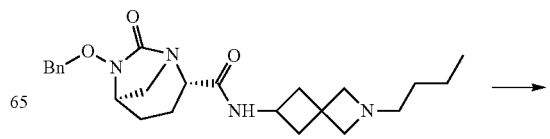

-continued

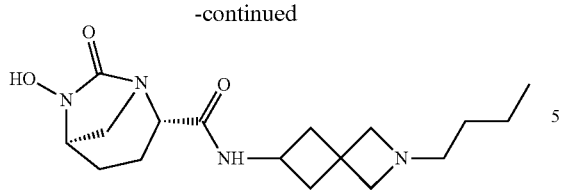

(2S,5R)-6-(benzyloxy)-N-(2-butyl-2-azaspiro[3.3]heptan-6-yl)-7-oxo-1,6-diazabicyclo[3.2.1]octane-2-carboxamide (0.55 g, 1.3 mmol) was dissolved in methanol (20 mL), Pd/C (55 mg, mass fraction 10%) was added, purged with hydrogen gas, stirred at 25° C. for 3 h. After completion of the reaction as measured by LC-MS, suck filtration was performed, the filtrate was concentrated to obtain the title compound (435 mg, yield 99.5%).

(3) Preparation of (2S,5R)-2-((2-butyl-2-azaspiro[3.3]heptan-6-yl)carbamoyl)-7-oxo-1,6-diazabicyclo[3.2.1]octan-6-yl hydrogen sulfate

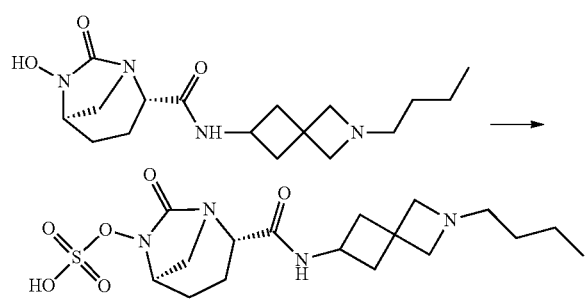

(2S,5R)—N-(2-butyl-2-azaspiro[3.3]heptan-6-yl)-6-hydroxyl-7-oxo-1,6-diazabicyclo[3.2.1]octane-2-carboxamide (435 mg, 1.29 mmol) was dissolved in pyridine (10 mL), added under stirring with sulfur trioxide-pyridine complex (575 mg, 3.61 mmol), stirred at 25° C. for 17 h, concentrated, ethyl acetate (50 mL) was added, shaken under ultrasonic, filtrated to obtain white solid, the solid was dissolved in acetonitrile (10 mL), trifluoroacetic acid (0.5 mL) was added, shaken under ultrasonic to generate a white precipitate, suck filtrated, solid was dissolved in water (3 mL), separated by preparative reversed-phase chromatography (acetonitrile:water=0~37%) to obtain the title compound in white color (20 mg, yield 3.7%). Molecular Formula: $C_{17}H_{28}N_4O_6S$ Molecular Weight: 416.5 LC-MS (m/z): 417.2[M+H]$^+$ $^1$H-NMR (400 MHz, D$_2$O) δ: 4.25-4.23 (m, 1H), 4.11-3.86 (m, 6H), 3.18 (d, J=11.2 Hz, 1H), 3.05-2.89 (m, 3H), 2.68-2.59 (m, 1H), 2.57-2.48 (s, 1H), 2.27-2.17 (m, 2H), 2.06-1.92 (m, 2H), 1.83-1.73 (m, 1H), 1.69-1.60 (m, 1H), 1.42-1.35 (m, 2H), 1.25-1.16 (m, 2H), 0.79-0.71 (m, 3H).

Example 13: Preparation of (2S,5R)-2-(2-cyclopropyl-2-azaspiro[3.3]heptan-6-ylcarbamoyl)-7-oxo-1,6-diazabicyclo[3.2.1]octan-6-yl hydrogen sulfate (Compound 13)

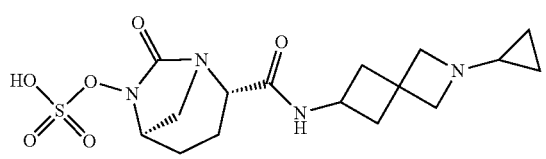 [SMILES: O=C(NC1CC2(C1)CN(C1CC1)C2)[C@@H]1CC[C@@H]2CN1C(=O)N2OS(=O)(=O)O]

(1) Preparation of (2S,5R)-6-(phenyl methoxy)-N-(2-cyclopropyl-2-azaspiro[3.3]heptan-6-yl)-7-oxo-1,6-diazabicyclo[3.2.1]octane-2-carboxamide

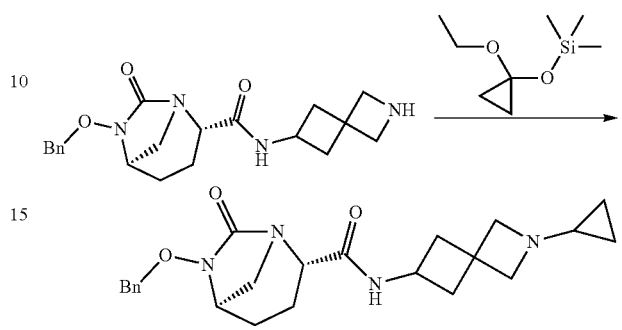

(2S,5R)-6-(phenylmethoxy)-7-oxo-N-(2-azaspiro[3.3]heptan-6-yl)-1,6-diazabicyclo[3.2.1]octane-2-carboxamide crude product and (1-ethoxycyclopropyloxy)trimethylsilane (1.7 g, 9.75 mmol) were dissolved in tetrahydrofuran (50 mL), acetic acid (50 μL) was added, stirred at 25° C. for 30 min, then sodium cyanoborohydride (0.8 g, 12.74 mmol) was added, heated to 50° C., stirred and reacted for 16 h. The reaction solution was quenched with water (100 mL), extracted by adding with ethyl acetate (50 mL×3), the organic phases were combined, dried over anhydrous sodium sulfate, filtrated and concentrated. The crude product was purified by silica gel column (dichloromethane:methanol=10:1) to obtain the title compound as a colorless gum (0.8 g, yield over two steps 40.0%).

(2) Preparation of (2S,5R)—N-(2-cyclopropyl-2-azaspiro[3.3]heptan-6-yl)-6-hydroxyl-7-oxo-1,6-diazabicyclo[3.2.1]octane-2-carboxamide

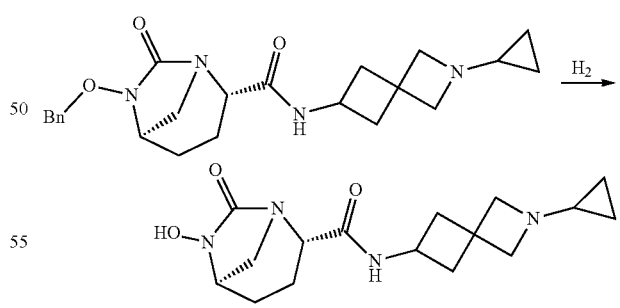

(2S,5R)-6-(phenylmethoxy)-N-(2-cyclopropyl-2-azaspiro[3.3]heptan-6-yl)-7-oxo-1,6-diazabicyclo[3.2.1]octane-2-carboxamide (0.8 g, 1.95 mmol) was dissolved in methanol (10 mL), Pd/C (0.2 g) was added, stirred and reacted at 25° C. under compressed hydrogen gas for 16 h, filtrated, concentrated to obtain the title compound as a colorless gum (0.6 g, yield 96.8%).

(3) Preparation of pyridine (2S,5R)-2-(2-cyclopropyl-2-azaspiro[3.3]heptan-6-ylcarbamoyl)-7-oxo-1,6-diazabicyclo[3.2.1]octan-6-yl sulfate

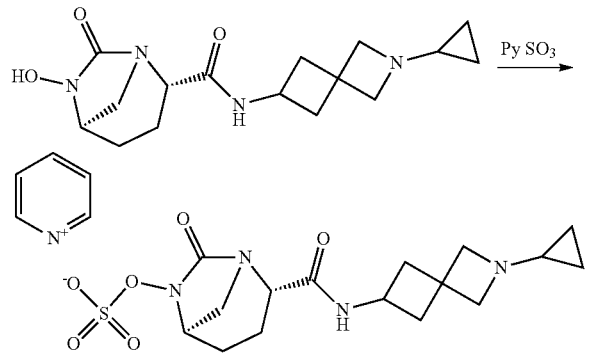

(2S,5R)—N-(2-cyclopropyl-2-azaspiro[3.3]heptan-6-yl)-6-hydroxyl-7-oxo-1,6-diazabicyclo[3.2.1]octane-2-carboxamide (0.6 g, 1.87 mmol) was dissolved in pyridine (10 mL), sulfur trioxide-pyridine complex (0.9 g, 5.65 mmol) was added, stirred and reacted at 25° C. for 16 h. The reaction solution was concentrated, washed by adding ethyl acetate (50 mL×5), the resultant solid was dissolved in water, and purified by Combiflash (mobile phase: acetonitrile/water=0-20%) to obtain the crude product solution of the title compound.

(4) Preparation of sodium (2S,5R)-2-(2-cyclopropyl-2-azaspiro[3.3]heptan-6-ylcarbamoyl)-7-oxo-1,6-diazabicyclo[3.2.1]octan-6-yl sulfate

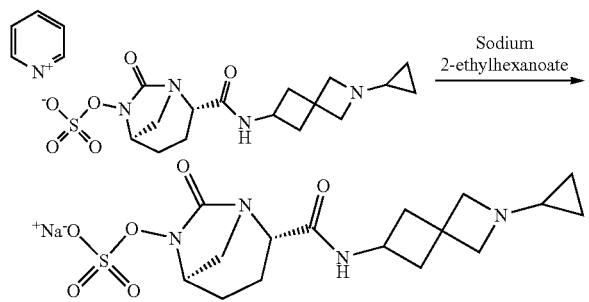

The pyridine (2S,5R)-2-(2-cyclopropyl-2-azaspiro[3.3]heptan-6-ylcarbamoyl)-7-oxo-1,6-diazabicyclo[3.2.1]octan-6-yl sulfate crude product solution as obtained in the previous step was concentrated to 5 mL, sodium iso-octoate was added to regulate pH=7, purified by Combiflash (mobile phase: acetonitrile/water=0-20%) to obtain the title compound as a crude product solution.

(5) Preparation of (2S,5R)-2-(2-cyclopropyl-2-azaspiro[3.3]heptan-6-ylcarbamoyl)-7-oxo-1,6-diazabicyclo[3.2.1]octan-6-yl hydrogen sulfate

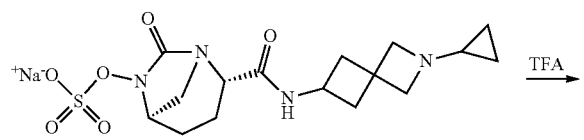

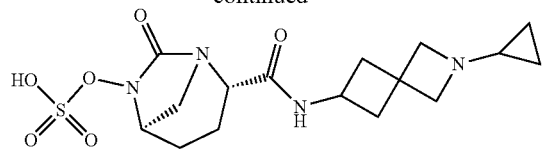

Sodium (2S,5R)-2-(2-cyclopropyl-2-azaspiro[3.3]heptan-6-ylcarbamoyl)-7-oxo-1,6-diazabicyclo[3.2.1]octan-6-yl sulfate crude product solution was concentrated to 5 mL, trifluoroacetic acid was added to regulate pH=5, purified by Combiflash (mobile phase: acetonitrile/water=0-10%), freeze-dried to obtain the title compound as a white solid (80 mg, yield over three steps 10.7%).

Molecular Formula: $C_{16}H_{24}N_4O_6S$ Molecular Weight: 400.4 LC-MS (m/z): 401.1[M+H]$^+$ $^1$H-NMR (400 MHz, D$_2$O) δ: 4.25-4.10 (m, 6H), 3.93 (d, J=6.8 Hz, 1H), 3.25 (d, J=12 Hz, 1H), 2.98 (d, J=12.4 Hz, 1H), 2.90-2.83 (m, 1H), 2.69-2.62 (m, 2H), 2.33-2.28 (m, 2H), 2.18-2.10 (m, 1H), 2.08-1.97 (m, 1H), 1.90-1.80 (m, 1H), 1.79-1.69 (m, 1H), 0.85-0.78 (m, 2H), 0.76-0.71 (m, 2H).

Example 14: Preparation of sodium (2S,5R)-2-((2-(cyclopropylmethyl)-2-azaspiro[3.3]heptan-6-yl)carbamoyl)-7-oxo-1,6-diazabicyclo[3.2.1]octan-6-yl sulfate (Compound 14)

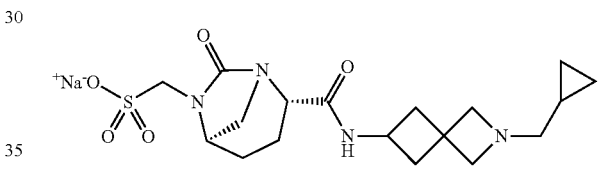

(1) Preparation of (2S,5R)-6-(benzyl oxy)-N-(2-(cyclopropylmethyl)-2-azaspiro[3.3]heptan-6-yl)-7-oxo-1,6-diaza bicyclo[3.2.1]octane-2-carboxamide

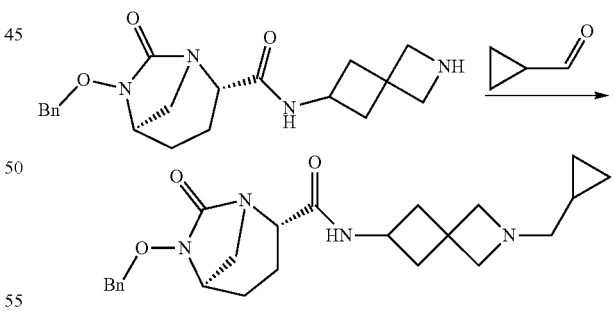

(2S,5R)-6-(benzyloxy)-7-oxo-N-(2-azaspiro[3.3]heptan-6-yl)-1,6-diazabicyclo[3.2.1]octane-2-carboxamide crude product and cyclopropylformaldehyde (1.2 g, 17.1 mmol) were dissolved in dichloromethane (50 mL), acetic acid (50 μL), stirred at 25° C. for 30 min, then sodium cyanoborohydride (428 mg, 6.8 mmol) was added, reacted at 25° C. for 16 h. The reaction solution was quenched with water (100 mL), extracted by adding with ethyl acetate (50 mL×3), all the organic phases were combined, dried over anhydrous sodium sulfate, filtrated, concentrated, the crude product was purified by silica gel column chromatography (dichloromethane:methanol=10:1) to obtain the title compound as a colorless gum (0.7 g, two-step yield 48.6%).

(2) Preparation of (2S,5R)—N-(2-(cyclopropylmethyl)-2-azaspiro[3.3]heptan-6-yl)-6-hydroxyl-7-oxo-1,6-diazabicyclo[3.2.1]octane-2-carboxamide

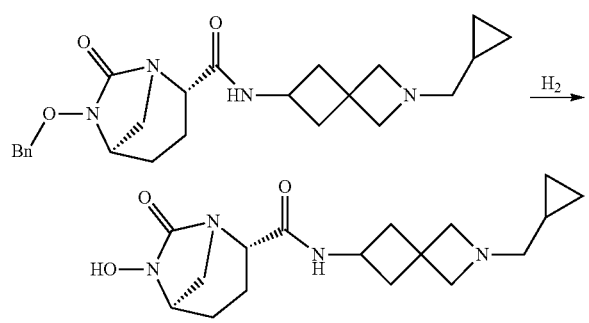

(2S,5R)-6-(benzyloxy)-N-(2-(cyclopropylmethyl)-2-azaspiro[3.3]heptan-6-yl)-7-oxo-1,6-diazabicyclo[3.2.1]octane-2-carboxamide (0.7 g, 1.65 mmol) was dissolved in methanol (10 mL), Pd/C (0.2 g) was added, reacted at 25° C. under compressed hydrogen gas for 16 h, filtrated, concentrated to obtain the crude product of the title compound as a colorless gum, which was directly used in the next reaction step.

(3) Preparation of pyridine (2S,5R)-2-((2-(cyclopropylmethyl)-2-azaspiro[3.3]heptan-6-yl) carbamoyl)-7-oxo-1,6-diazabicyclo[3.2.1]octan-6-yl sulfate

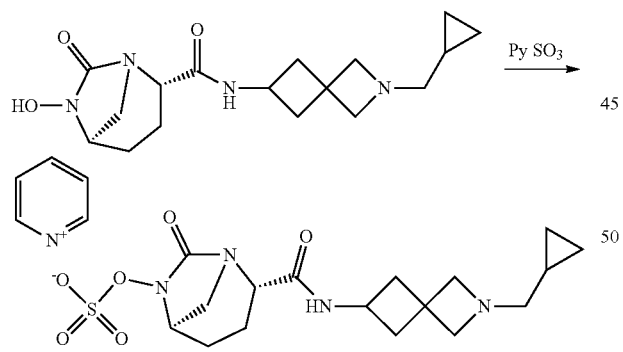

The crude product (2S,5R)—N-(2-(cyclopropylmethyl)-2-azaspiro[3.3]heptan-6-yl)-6-hydroxyl-7-oxo-1,6-diazabicyclo[3.2.1]octane-2-carboxamide as obtained in the previous step was dissolved in pyridine (10 mL), sulfur trioxide-pyridine complex (1.3 g, 8.23 mmol) was added, reacted at 25° C. for 16 h. The reaction solution was concentrated and washed with ethyl acetate (50 mL), the resultant solid was dissolved in water, purified by Combiflash (mobile phase: acetonitrile/water=0-20%) to obtain the title compound as a crude product solution.

(4) Preparation of sodium (2S,5R)-2-((2-(cyclopropylmethyl)-2-azaspiro[3.3]heptan-6-yl) carbamoyl)-7-oxo-1,6-diazabicyclo[3.2.1]octan-6-yl sulfate

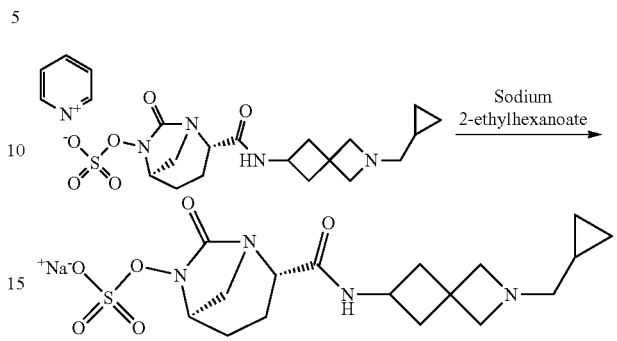

The crude product solution of pyridine (2S,5R)-2-((2-(cyclopropylmethyl)-2-azaspiro[3.3]heptan-6-yl)carbamoyl)-7-oxo-1,6-diazabicyclo[3.2.1]octan-6-yl sulfate as obtained in the previous step was concentrated to 5 mL, sodium iso-octoate was added to regulate pH=7, purified by Combiflash (mobile phase: acetonitrile/water=0-20%) to obtain the title compound as a white solid (75 mg, yield over three steps 10.4%).

Molecular Formula: $C_{17}H_{25}N_4NaO_6S$ Molecular Weight: 436.5 LC-MS (m/z): 416.2[M+H]$^+$ $^1$H-NMR (400 MHz, D$_2$O) δ: 4.23 (d, J=10.4 Hz, 1H), 4.10-4.02 (m, 4H), 3.95 (d, J=10.8 Hz, 1H), 3.84 (d, J=7.2 Hz, 1H), 3.15 (d, J=11.6 Hz, 1H), 2.88 (d, J=7.6 Hz, 1H), 2.63 (s, 1H), 2.49 (s, 1H), 2.24-2.18 (m, 2H), 2.01-1.99 (m, 1H), 1.91-1.89 (m, 1H), 1.76-1.74 (m, 1H), 1.69-1.59 (m, 1H), 0.81-0.79 (m, 1H), 0.49-0.46 (m, 2H), 0.18-0.14 (m, 2H).

Example 15: Preparation of (2S,5R)-2-(3,9-diazabicyclo[3.3.1]nonan-7-ylcarbamoyl)-7-oxo-1,6-diazabicyclo[3.2.1]octan-6-yl hydrogen sulfate (Compound 15)

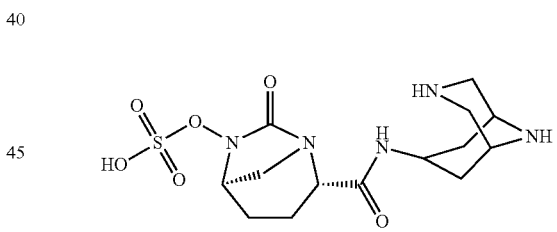

(1) Preparation of ethyl 4-((4-methoxybenzyl)-(3-ethoxycarbonyl-allyl)amino)but-2-enoate

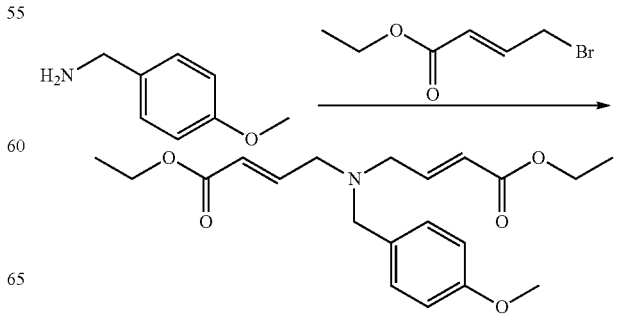

4-Methoxybenzylamine (29.8 g, 217.2 mmol) was dissolved in ethanol (1 L), N,N-diisopropylethylamine (84.25 g, 651.6 mmol) was added, ethyl 4-bromocrotonate (75%, 122.96 g, 477.84 mmol) was slowly added, heated to 40° C. by using oil-bath, reacted for 16 h. After completion of the reaction as measured by TLC (petroleum ether:ethyl acetate=5:1), the reaction solution was concentrated in vacuum, water (500 mL) was added, extracted with ethyl acetate (500 mL×2), the organic phases were combined and concentrated in vacuum, the crude product was purified by silica gel column chromatography (petroleum ether:ethyl acetate=10:1) to obtain the title compound (76 g, yield 96.8%).

(2) Preparation of diethyl 2,2'-(4-(4-methoxybenzyl)piperazin-2,6-diyl) diacetate

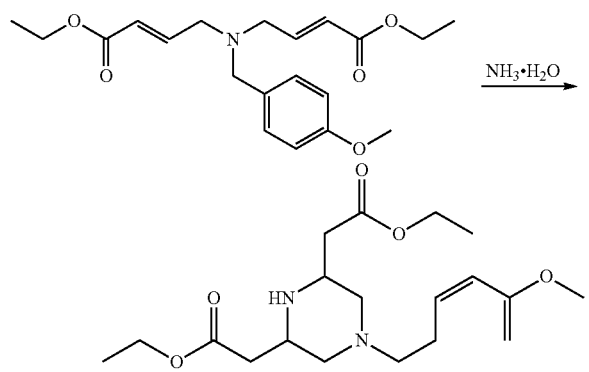

Ethyl 4-((4-methoxybenzyl)-(3-methoxycarbonylallyl)amino)but-2-enoate (10 g, 27.67 mmol) was dissolved in ethanol (50 mL), aqueous ammonia (30 mL) was added, reacted in a sealed tube at 80° C. for 16 h. After completion of the reaction as measured by TLC (petroleum ether:ethyl acetate=1:1), concentrated in vacuum, the crude product was purified by silica gel column chromatography (petroleum ether:ethyl acetate=1:1) to obtain the title compound (5.1 g, yield 48.7%).

(3) Preparation of diethyl 2,2'-(piperazin-2,6-diyl)diacetate

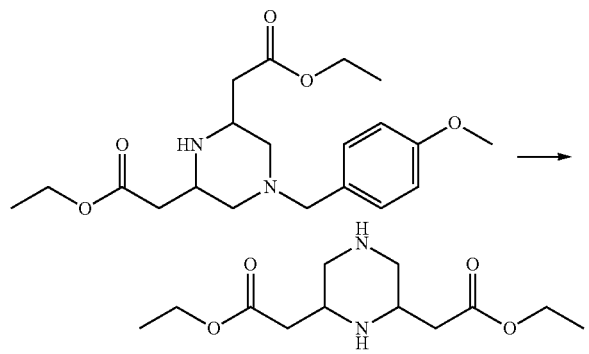

Diethyl 2,2'-(4-(4-methoxybenzyl)piperazin-2,6-diyl)diacetate (3 g, 7.93 mmol) was dissolved in trifluoroacetic acid (50 mL), anisole (1 mL) was added, reacted at 90° C. for 48 h. After completion of the reaction as measured by TLC (dichloromethane:methanol=20:1), concentrated in vacuum to obtain crude product (3.5 g), which was directly used in the next step.

(4) Preparation of di(tert-butyl) 2,6-bis(2-ethoxy-2-oxoethyl)piperazin-1,4-dicarboxylate

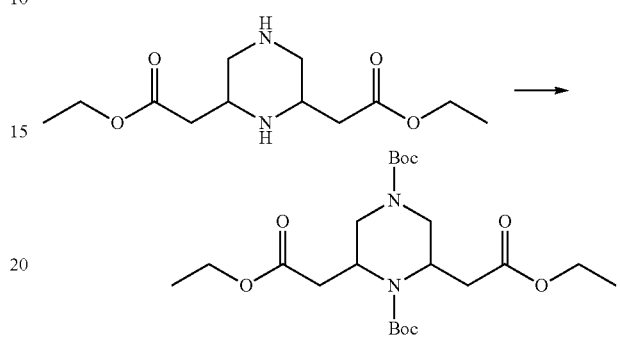

Diethyl 2,2'-(piperazin-2,6-diyl)diacetate (3.5 g of crude product) was dissolved in dichloromethane (50 mL), triethylamine (4.82 g, 47.58 mmol) and di(tert-butyl) dicarbonate (5.19 g, 23.79 mmol) were added, reacted at 25° C. for 16 h. After completion of the reaction as measured by TLC (petroleum ether:ethyl acetate=1:1), concentrated in vacuum, the crude product was purified by silica gel column chromatography (petroleum ether:ethyl acetate=3:1) to obtain the title compound (2.2 g, two-step yield 60.6%).

(5) Preparation of 3,9-di(tert-butyl) 6-ethyl 7-oxo-3,9-diazabicyclo[3.3.1]nonane-3,6,9-tricarboxylate

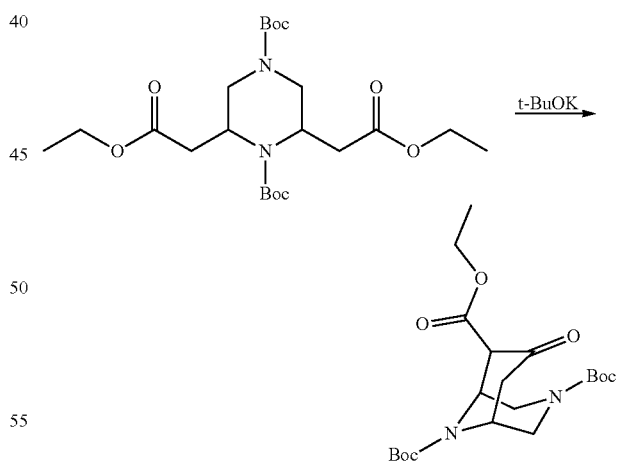

Di(tert-butyl) 2,6-bis(2-ethoxy-2-oxoethyl)piperazin-1,4-dicarboxylate (2.2 g, 4.8 mmol) was dissolved in tetrahydrofuran (30 mL), potassium tert-butoxide (1.89 g, 16.8 mmol) was slowly added, heated to 40° C. and stirred for 16 h. After completion of the reaction as measured by TLC (petroleum ether:ethyl acetate=1:1), concentrated in vacuum, the crude product was purified by silica gel column chromatography (petroleum ether:ethyl acetate=1:1) to obtain the title compound (1.7 g, yield 85.9%).

(6) Preparation of 3,9-diazabicyclo[3.3.1]nonan-7-one

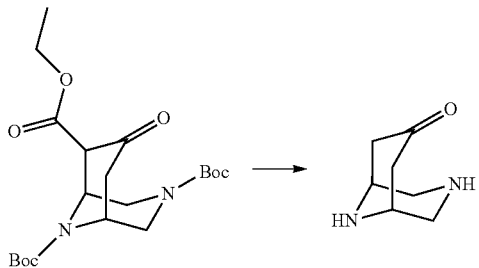 [SMILES: CCOC(=O)C1C(=O)CC2CN(C(=O)OC(C)(C)C)CC1N2C(=O)OC(C)(C)C ; O=C1CC2CNCC(C1)N2]

3,9-Di(tert-butyl) 6-ethyl 7-oxo-3,9-diazabicyclo[3.3.1]nonane-3,6,9-tricarboxylate (1.7 g, 4.12 mmol) was dissolved in hydrochloric acid (6 mol/L, 30 mL), heated to 100° C. and stirred for 16 h. After completion of the reaction as measured by TLC (dichloromethane:methanol=10:1), concentrated in vacuum to obtain the title compound (1.5 g of crude product), which was directly used in the next reaction step.

(7) Preparation of di(tert-butyl) 7-oxo-3,9-diazabicyclo[3.3.1]nonane-3,9-dicarboxylate

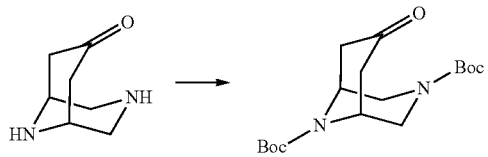 [SMILES: O=C1CC2CNCC(C1)N2 ; CC(C)(C)OC(=O)N1CC2CC(=O)CC(C1)N2C(=O)OC(C)(C)C]

3,9-Diazabicyclo[3.3.1]nonan-7-one (1.5 g of crude product) was dissolved in dichloromethane (50 mL), N,N-diisopropylethylamine (3.2 g, 24.72 mmol) and di(tert-butyl) dicarbonate (2.7 g, 12.36 mmol) were added, stirred at 25° C. for 16 h. After completion of the reaction as measured by TLC (petroleum ether:ethyl acetate=1:1), concentrated in vacuum, the crude product was purified by silica gel column chromatography (petroleum ether:ethyl acetate=3:1) to obtain the title compound (950 mg, two-step yield 67.9%).

(8) Preparation of di(tert-butyl) 7-amino-3,9-diazabicyclo[3.3.1]nonane-3,9-dicarboxylate

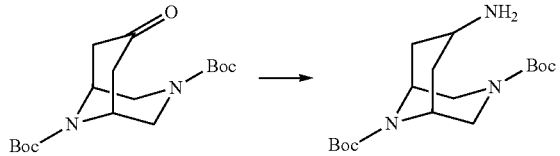 [SMILES: CC(C)(C)OC(=O)N1CC2CC(=O)CC(C1)N2C(=O)OC(C)(C)C ; CC(C)(C)OC(=O)N1CC2CC(N)CC(C1)N2C(=O)OC(C)(C)C]

Di(tert-butyl) 7-oxo-3,9-diazabicyclo[3.3.1]nonane-3,9-dicarboxylate (950 mg, 2.79 mmol) was dissolved in ammoniamethanol solution (7 mol/L, 25 mL), tetraisopropyl titanate (3.17 g, 11.16 mmol) was added, stirred at 25° C. for 16 h, sodium borohydride (527 mg, 13.95 mmol) was added. After completion of the reaction as measured by TLC (dichloromethane:methanol=20:1), aqueous ammonia (5 mL) was added, filtrated to remove insoluble substance, the filtrate was concentrated in vacuum, the crude product was purified by silica gel column chromatography (dichloromethane:methanol=20:1) to obtain the title compound (520 mg, yield 54.6%).

(9) Preparation of di(tert-butyl) 7-((2S,5R)-6-(benzyloxy)-7-oxo-1,6-diazabicyclo[3.2.1]octane-2-carboxamido)-3,9-diazabicyclo[3.3.1]nonane-3,9-dicarboxylate

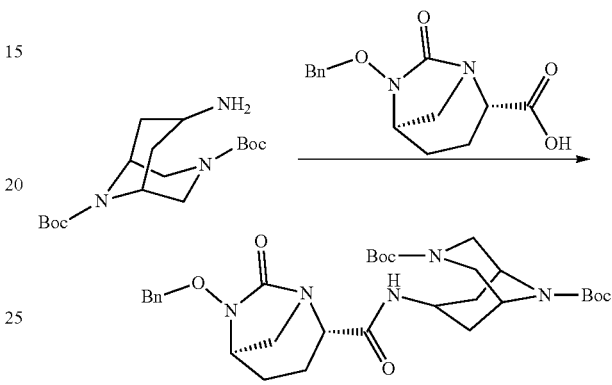

(2S,5R)-6-(benzyloxy)-7-oxo-1,6-diazabicyclo[3.2.1]octane-2-carboxylic acid (364.7 mg, 1.32 mmol) and di(tert-butyl) 7-amino-3,9-diazabicyclo[3.3.1]nonane-3,9-dicarboxylate (450 mg, 1.32 mmol) were dissolved in dichloromethane (20 mL), triethylamine (400.7 mg, 3.96 mmol), 1-ethyl-(3-dimethylaminopropyl)carbodiimide hydrochloride (379.6 mg, 1.98 mmol) and 1-hydroxylbenzotriazole (267.5 mg, 1.98 mmol) were added, stirred at 25° C. for 16 h. After completion of the reaction as measured by TLC (petroleum ether:ethyl acetate=1:1), concentrated in vacuum, the crude product was separated by silica gel column chromatography (petroleum ether:ethyl acetate=1:1) to obtain the title compound (250 mg, yield 31.6%).

(10) Preparation of tetra(n-butyl)ammonium (2S,5R)-2-((3,9-bis(tert-butoxycarbonyl)-3,9-diazabicyclo[3.3.1]nonan-7-yl)carbamoyl)-7-oxo-1,6-diazabicyclo[3.2.1]octan-6-yl sulfate

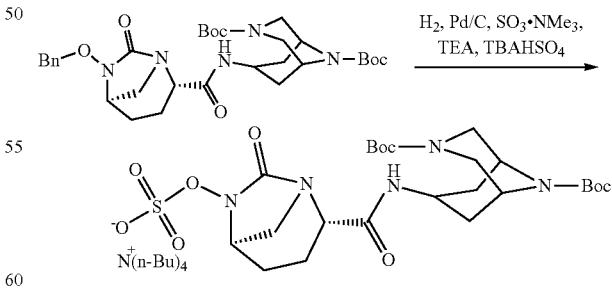

Di(tert-butyl) 7-((2S,5R)-6-(benzyloxy)-7-oxo-1,6-diazabicyclo[3.2.1]octane-2-carboxamido)-3,9-diazabicyclo[3.3.1]nonane-3,9-dicarboxylate (250 mg, 0.417 mmol) was dissolved in a mixture solvent of isopropanol (4 mL) and water (4 mL), Pd/C (25 mg, mass fraction 10%), triethylamine (10.5 mg, 0.104 mmol) and sulfur trioxide-trimethylamine complex (69.6 mg, 0.5 mmol) were serially added, purged with hydrogen gas, reacted at 25° C. for 16 h, filtrated to remove Pd/C, water (10 mL) was added, extracted with ethyl acetate (10 mL), the phases were separated to obtain the aqueous phase, to which was added tetrabutylammonium hydrogen sulfate (141.6 mg, 0.417 mmol), extracted with dichloromethane (25 mL×3), the organic phases were combined and concentrated in vacuum to obtain the title compound (195 mg, yield 56.3%).

(11) Preparation of (2S,5R)-2-(3,9-diazabicyclo[3.3.1]nonan-7-ylcarbamoyl)-7-oxo-1,6-diazabicyclo[3.2.1]octan-6-yl hydrogen sulfate

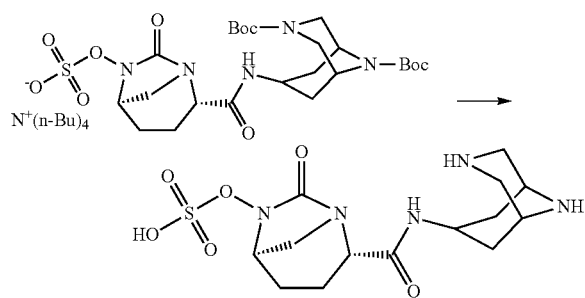

Tetra(n-butyl)ammonium (2S,5R)-2-((3,9-bis(tert-butoxycarbonyl)-3,9-diazabicyclo[3.3.1]nonan-7-yl)carbamoyl)-7-oxo-1,6-diazabicyclo[3.2.1]octan-6-yl sulfate (195 mg, 0.235 mmol) was added to dichloromethane (2 mL), cooled to 0° C., trifluoroacetic acid (2 mL) was added, reacted at 0° C. for 1 h, concentrated in vacuum to remove solvent, acetonitrile (10 mL) was added and shaken with ultrasonic to generate precipitate, suck filtrated, the resultant solid was dried in vacuum to obtain the title compound (64 mg, yield 70%).

Molecular Formula: $C_{14}H_{23}N_5O_6S$ Molecular Weight: 389.4 LC-MS (m/z): 390.2[M+H]$^+$ $^1$H-NMR (400 MHz, $D_2O$) δ: 4.22-4.08 (m, 4H), 3.94 (d, J=6.4 Hz, 1H), 3.52-3.35 (m, 4H), 3.22-3.20 (m, 1H), 2.96 (d, J=12 Hz, 1H), 2.68-2.55 (m, 2H), 2.15-1.90 (m, 2H), 1.89-1.62 (m, 4H).

What is claimed is:

1. A compound of Formula (I), a pharmaceutically acceptable salt, ester, solvate or stereoisomer thereof:

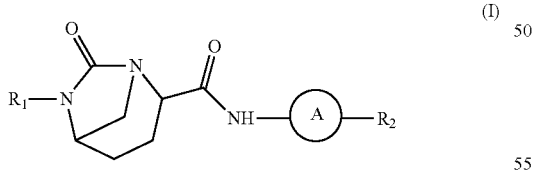

wherein,
$R_1$ is —$SO_3M$, —$OSO_3M$, —$SO_2NH_2$, —$PO_3M$, —$OPO_3M$, —$CH_2CO_2M$, —$CF_2CO_2M$ or $CF_3$;
M is selected from H or a pharmaceutically acceptable cation;
Ring A is selected from the group consisting of 5- to 15-membered bridged cyclyl, 5- to 15-membered spiro cyclyl, 5- to 15-membered bridged heterocyclyl or 5- to 15-membered spiro heterocyclyl, which is optionally substituted with substituent(s) selected from the group consisting of halogen, amino, carboxyl, hydroxyl, cyano, $C_{1-6}$ alkyl, halo $C_{1-6}$ alkyl, $C_{1-6}$ alkoxy, $C_{1-6}$ alkylamino or $C_{1-6}$ alkylcarbonyl;
$R_2$ is selected from the group consisting of hydrogen atom, halogen, amino, carboxyl, hydroxyl, $C_{1-6}$ alkyl, halo $C_{1-6}$ alkyl, hydroxyl$C_{1-6}$ alkyl, $C_{1-6}$ alkoxy, $C_{1-6}$ alkoxy$C_{1-6}$ alkyl, halo $C_{1-6}$ alkoxy, halo $C_{1-6}$ alkoxy$C_{1-6}$ alkyl, $C_{1-6}$ alkylamino, di($C_{1-6}$ alkyl)amino, $C_{1-6}$ alkylamino$C_{1-6}$ alkyl, $C_{1-6}$ alkylcarbonyl, halo $C_{1-6}$ alkylcarbonyl, halo $C_{1-6}$ alkylcarbonyl$C_{1-6}$ alkyl, $C_{1-6}$ alkylcarbonyloxy, $C_{1-6}$ alkoxycarbonyl, $C_{1-6}$ alkylcarbonyloxy$C_{1-6}$ alkyl, $C_{1-6}$ alkylacylamino, $C_{1-6}$ alkylaminocarbonyl, di($C_{1-6}$ alkyl)aminocarbonyl, $C_{1-6}$ alkylsulfinyl, $C_{1-6}$ alkylsulfonyl, $C_{1-6}$ alkylsulfonyl$C_{1-6}$ alkyl, $C_{1-6}$ alkylsulfonylamino, $C_{1-6}$ alkylsulfonyloxy, $C_{2-6}$ alkenyl, $C_{2-6}$ alkynyl, 3- to 8-membered cycloalkyl, 3- to 8-membered cycloalkyl-$C_{1-6}$ alkyl, 6- to 8-membered aryl, 6- to 15-membered fused aryl, 4- to 15-membered fused cyclyl, 5- to 15-membered bridged cyclyl, 5- to 15-membered Spiro cyclyl, 3- to 8-membered heterocyclyl, 3- to 8-membered heterocyclyl-$C_{1-6}$ alkyl, 5- to 8-membered heteroaryl, 5- to 15-membered fused heteroaryl, 4- to 15-membered fused heterocyclyl, 5- to 15-membered bridged heterocyclyl or 5- to 15-membered Spiro heterocyclyl.

2. The compound, a pharmaceutically acceptable salt, ester, solvate or stereoisomer thereof according to claim 1, wherein the compound has a structure of Formula (II) as follows,

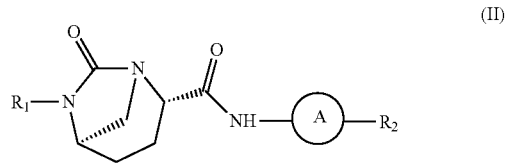

wherein, $R_1$, $R_2$, ring A have definitions as those in claim 1.

3. The compound, or a pharmaceutically acceptable salt, ester, solvate or stereoisomer thereof, according to claim 1, wherein the compound has a structure of Formula (III) as follows,

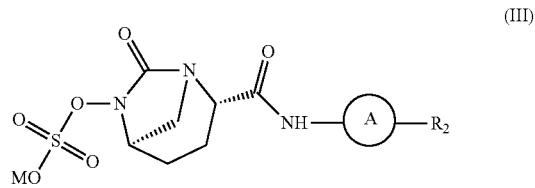

wherein,
Ring A is selected from the group consisting of 5- to 15-membered bridged heterocyclyl or 5- to 15-membered spiro heterocyclyl, which is optionally substituted with substituent(s) selected from the group consisting of halogen, amino, carboxyl, hydroxyl, cyano, $C_{1-6}$ alkyl, halo $C_{1-6}$ alkyl, $C_{1-6}$ alkoxy, $C_{1-6}$ alkylamino or $C_{1-6}$ alkylcarbonyl;
$R_2$ is selected from the group consisting of hydrogen atom, halogen, amino, carboxyl, hydroxyl, $C_{1-6}$ alkyl, halo $C_{1-6}$ alkyl, hydroxyl$C_{1-6}$ alkyl, $C_{1-6}$ alkoxy, $C_{1-6}$ alkoxy$C_{1-6}$ alkyl, halo $C_{1-6}$ alkoxy, halo $C_{1-6}$ alkoxyC$_{1-6}$ alkyl, C$_{1-6}$ alkylamino, di(C$_{1-6}$ alkyl)amino, C$_{1-6}$ alkylaminoC$_{1-6}$ alkyl, C$_{1-6}$ alkylcarbonyl, halo C$_{1-6}$ alkylcarbonyl, halo C$_{1-6}$ alkylcarbonylC$_{1-6}$ alkyl, C$_{1-6}$ alkylcarbonyloxy, C$_{1-6}$ alkoxycarbonyl, C$_{1-6}$ alkylcarbonyloxyC$_{1-6}$ alkyl, C$_{1-6}$ alkylacylamino, C$_{1-6}$ alkylaminocarbonyl, di(C$_{1-6}$ alkyl)aminocarbonyl, C$_{1-6}$ alkylsulfinyl, C$_{1-6}$ alkylsulfonyl, C$_{1-6}$ alkylsulfonylC$_{1-6}$ alkyl, C$_{1-6}$ alkylsulfonylamino, C$_{1-6}$ alkylsulfonyloxy, C$_{2-6}$ alkenyl, C$_{2-6}$ alkynyl, 3- to 8-membered cyclyl, 3- to 8-membered cyclyl-C$_{1-6}$ alkyl, 4- to 10-membered fused cyclyl, 5- to 10-membered bridged cyclyl, 5- to 10-membered spiro cyclyl, 3- to 8-membered heterocyclyl, 3- to 8-membered heterocyclyl-C$_{1-6}$ alkyl, 4- to 10-membered fused heterocyclyl, 5- to 10-membered bridged heterocyclyl or 5- to 10-membered spiro heterocyclyl;

M is selected from the group consisting of H, sodium ion, potassium ion, calcium ion, magnesium ion, zinc ion or tetra(C$_{1-6}$ alkyl)quaternary ammonium ion.

4. The compound, a pharmaceutically acceptable salt, ester, solvate or stereoisomer thereof according to claim 3, wherein, Ring A is selected from 5- to 15-membered nitrogen-containing bridged heterocyclyl, which is optionally substituted with substituent(s) selected from the group consisting of halogen, amino, carboxyl, hydroxyl, cyano, C$_{1-6}$ alkyl, halo C$_{1-6}$ alkyl or C$_{1-6}$ alkoxy;

R$_2$ is selected from the group consisting of hydrogen atom, halogen, amino, carboxyl, hydroxyl, C$_{1-6}$ alkyl, halo C$_{1-6}$ alkyl, hydroxylC$_{1-6}$ alkyl, C$_{1-6}$ alkoxy, halo C$_{1-6}$ alkoxy, C$_{1-6}$ alkylamino, di(C$_{1-6}$ alkyl)amino, C$_{1-6}$ alkylcarbonyl, halo C$_{1-6}$ alkylcarbonyl, C$_{1-6}$ alkylcarbonyloxy, C$_{1-6}$ alkylacylamino, C$_{1-6}$ alkylsulfinyl, C$_{1-6}$ alkylsulfonyl, C$_{1-6}$ alkylsulfonylamino, 3- to 6-membered cycloalkyl, 3- to 6-membered cycloalkyl-C$_{1-6}$ alkyl, 3- to 6-membered heterocyclyl, 5- to 9-membered fused heterocyclyl, 6- to 9-membered bridged heterocyclyl or 6- to 9-membered spiro heterocyclyl;

M is selected from the group consisting of H, sodium ion, potassium ion, zinc ion or tetrabutylammonium ion.

5. The compound, a pharmaceutically acceptable salt, ester or stereoisomer thereof according to claim 4, wherein, Ring A is selected from 7- to 9-membered nitrogen-containing bridged heterocyclyl, which is optionally substituted with substituent(s) selected from the group consisting of fluorine atom, chlorine atom, bromine atom, amino, hydroxyl, methyl, ethyl or propyl;

R$_2$ is selected from the group consisting of hydrogen atom, fluorine atom, chlorine atom, amino, hydroxyl, methyl, ethyl, trifluoromethyl, methoxy, trifluoromethoxy, acetyl, methylsulfonyl, cyclopentyl, cyclohexyl, pyrrolidinyl, tetrahydrofuryl, imidazolidinyl, oxazolidinyl, tetrahydropyranyl, piperidyl or morpholinyl.

6. The compound, a pharmaceutically acceptable salt, ester, solvate or stereoisomer thereof according to claim 5, wherein, Ring A is selected from the group consisting of 2-azabicyclo[2.2.1]heptyl, 7-azabicyclo[2.2.1]heptyl, 3-azabicyclo[3.2.1]octyl, 8-azabicyclo[3.2.1]octyl, 2-azabicyclo[3.2.1]octyl, 2-azabicyclo[2.2.2]octyl, 2,5-diazabicyclo[2.2.1]heptyl, 3,8-diazabicyclo[3.2.1]octyl, 2-oxa-5-azabicyclo[2.2.1]heptyl, 8-oxa-3-azabicyclo[3.2.1]octyl, 3,8-diazabicyclo[3.2.1]oct-6-enyl or 3,9-diazabicyclo[3.3.1]nonyl, which is optionally substituted with substituent(s) selected from the group consisting of fluorine atom, chlorine atom, amino, hydroxyl, methyl, ethyl or propyl;

R$_2$ is selected from the group consisting of hydrogen atom, fluorine atom, chlorine atom, amino, hydroxyl, methyl, ethyl, trifluoromethyl, methoxy, trifluoromethoxy, acetyl, methylsulfonyl, cyclohexyl, pyrrolidinyl, piperidyl or morpholinyl.

7. The compound, a pharmaceutically acceptable salt, ester, solvate or stereoisomer thereof according to claim 3, wherein, Ring A is selected from 5- to 15-membered nitrogen-containing spiro heterocyclyl, which is optionally substituted with substituent(s) selected from the group consisting of halogen, amino, carboxyl, hydroxyl, cyano, C$_{1-6}$ alkyl, halo C$_{1-6}$ alkyl or C$_{1-6}$ alkoxy;

R$_2$ is selected from the group consisting of hydrogen atom, halogen, amino, carboxyl, hydroxyl, C$_{1-6}$ alkyl, halo C$_{1-6}$ alkyl, hydroxylC$_{1-6}$ alkyl, C$_{1-6}$ alkoxy, halo C$_{1-6}$ alkoxy, C$_{1-6}$ alkylamino, di(C$_{1-6}$ alkyl)amino, C$_{1-6}$ alkylcarbonyl, halo C$_{1-6}$ alkylcarbonyl, C$_{1-6}$ alkylcarbonyloxy, C$_{1-6}$ alkylacylamino, C$_{1-6}$ alkylsulfinyl, C$_{1-6}$ alkylsulfonyl, C$_{1-6}$ alkylsulfonylamino, 3- to 6-membered cycloalkyl, 3- to 6-membered cycloalkyl-C$_{1-6}$ alkyl, 3- to 6-membered heterocyclyl, 5- to 9-membered fused heterocyclyl, 6- to 9-membered bridged heterocyclyl or 6- to 9-membered spiro heterocyclyl.

8. The compound, a pharmaceutically acceptable salt, ester, solvate or stereoisomer thereof according to claim 7, wherein, Ring A is selected from 7- to 9-membered nitrogen-containing spiro heterocyclyl, which is optionally substituted with substituent(s) selected from the group consisting of fluorine atom, chlorine atom, bromine atom, amino, hydroxyl, methyl, ethyl or propyl;

R$_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclopentyl, cyclohexyl, pyrrolidinyl, imidazolidinyl, oxazolidinyl, tetrahydrofuryl, tetrahydropyranyl, piperidyl or morpholinyl.

9. The compound, its pharmaceutically acceptable salts, its esters, its solvates or its stereoisomers, according to claim 8, wherein, Ring A is selected from 8- to 9-membered nitrogen-containing spiro heterocyclyl, which is optionally substituted with substituent(s) selected from the group consisting of fluorine atom, chlorine atom, bromine atom, amino, hydroxyl, methyl, ethyl or propyl;

R$_2$ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclopentyl, cyclohexyl, pyrrolidinyl, tetrahydrofuryl, tetrahydropyranyl, piperidyl or morpholinyl.

10. The compound, its pharmaceutically acceptable salts, its esters, its solvates or its stereoisomers, according to claim 8, wherein, Ring A is selected from 7-membered nitrogen-containing spiro heterocyclyl, which is optionally substituted with substituent(s) selected from the group consisting of fluorine atom, chlorine atom, bromine atom, amino, hydroxyl, methyl, ethyl or propyl;

R₂ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclopentyl, cyclohexyl, pyrrolidinyl, tetrahydrofuryl, tetrahydropyranyl, piperidyl or morpholinyl.

11. The compound, its pharmaceutically acceptable salts, its esters, its solvates or its stereoisomers, according to claim 8, wherein,
Ring A is selected from the group consisting of 5-azaspiro[2.4]heptyl, 2-azaspiro[3.3]heptyl, 2-azaspiro[3.5]nonyl, 2,6-diazaspiro[3.3]heptyl, 2-oxa-6-azaspiro[3.3]heptyl, 6-oxa-2-azaspiro[3.4]octyl, 2-azaspiro[3.4]octyl, 6-azaspiro[3.4]octyl, 2-azaspiro[4.4]nonyl, 2-oxa-7-azaspiro[4.4]nonyl, 6-azaspiro[3.4]oct-7-enyl, 2-oxa-6-azaspiro[3.4]oct-7-enyl or 2-azaspiro[4.4]non-7-enyl, which is optionally substituted with substituent(s) selected from the group consisting of fluorine atom, chlorine atom, amino, hydroxyl, methyl, ethyl or propyl;
R₂ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclohexyl, pyrrolidinyl, piperidyl or morpholinyl.

12. The compound, its pharmaceutically acceptable salts, its esters, its solvates or its stereoisomers, according to claim 11, wherein,
Ring A is selected from 2-azaspiro[3.3]heptyl, which is optionally substituted with substituent(s) selected from the group consisting of fluorine atom, chlorine atom, amino, hydroxyl, methyl, ethyl or propyl;
R₂ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclohexyl, pyrrolidinyl, piperidyl or morpholinyl.

13. The compound, its pharmaceutically acceptable salts, its esters, its solvates or its stereoisomers, according to claim 12, wherein,
Ring A is selected from 2-azaspiro[3.3]heptyl, which is optionally substituted with substituent(s) selected from the group consisting of fluorine atom, chlorine atom, amino, hydroxyl, methyl, ethyl or propyl, the 2-azaspiro[3.3]heptyl links to acylamino of parent nucleus via a ring carbon atom;
R₂ is selected from the group consisting of hydrogen atom, fluorine atom, chlorine atom, amino, hydroxyl, methyl, ethyl, butyl, trifluoromethyl, methoxy, trifluoromethoxy, acetyl, methylsulfonyl, cyclopropyl, cyclopropylmethyl, cyclohexyl, pyrrolidinyl, piperidyl or morpholinyl;
M is selected from the group consisting of H, sodium ion, potassium ion, zinc ion or tetrabutylammonium ion.

14. The compound, its pharmaceutically acceptable salts, its esters, its solvates or its stereoisomers, according to claim 13, wherein the compound has a structure of formula (IV) as follows,

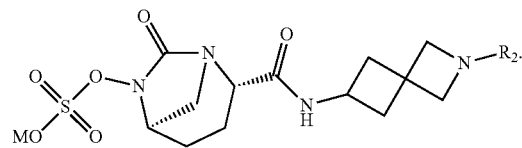

(IV)

15. The compound, its pharmaceutically acceptable salts, its esters, its solvates or its stereoisomers, according to claim 1, wherein, the compound is selected from the group consisting of:

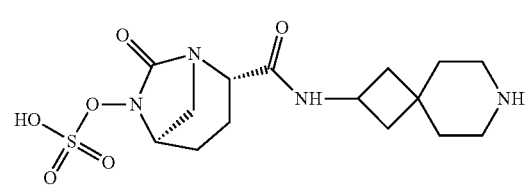

1

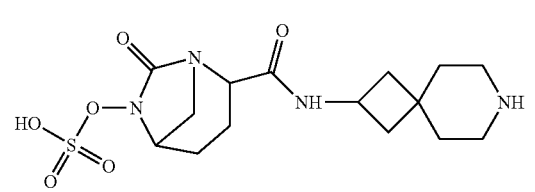

1-1

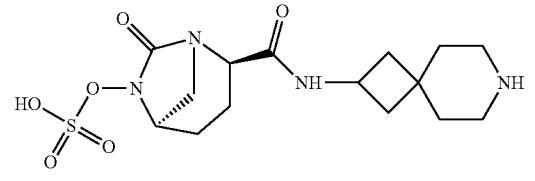

1-2

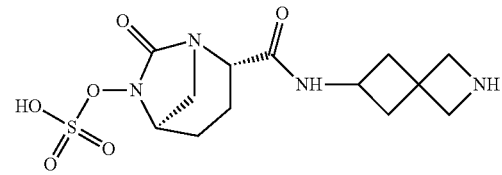

2

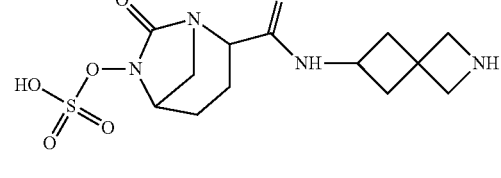

2-1

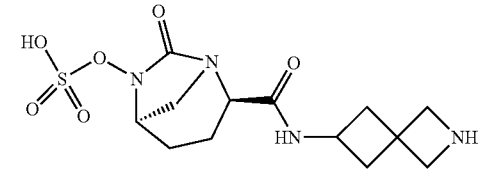

2-2

101
-continued
3
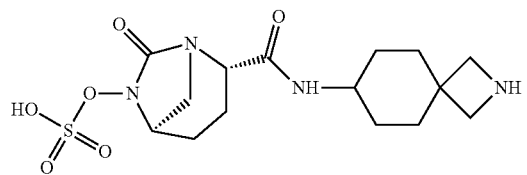
3-1
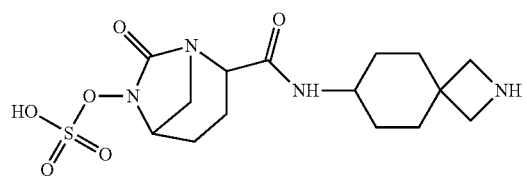
4
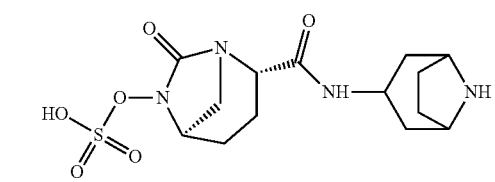
4-1
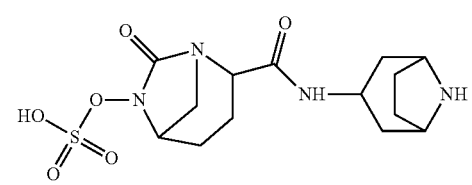
4-2
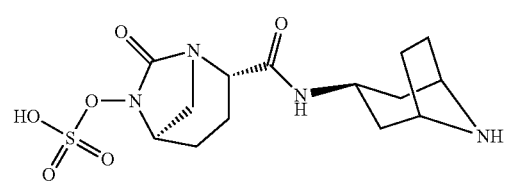
4-3
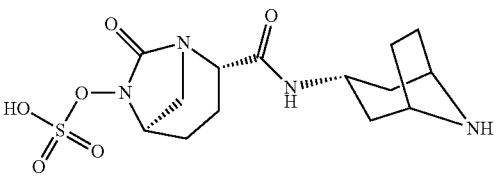
4-4
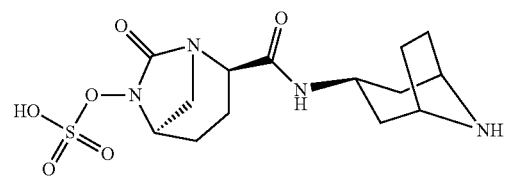
4-5
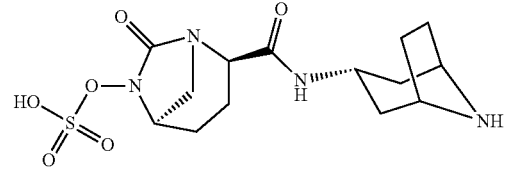
102
-continued
5
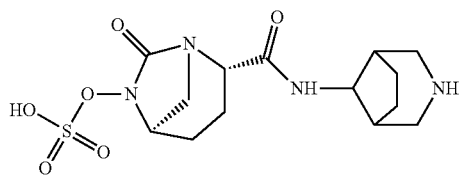
5-1
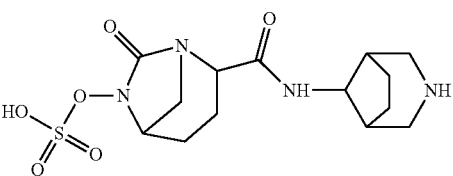
5-2
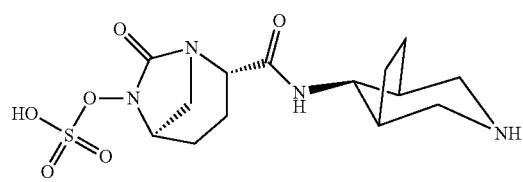
5-3
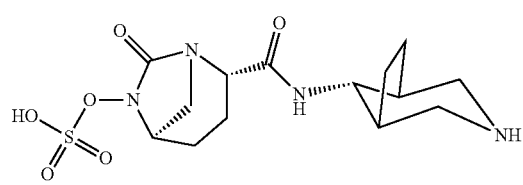
5-4
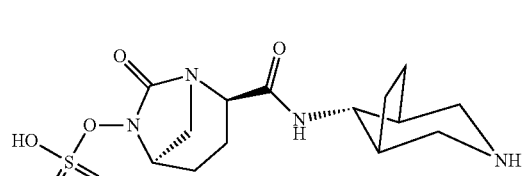
5-5
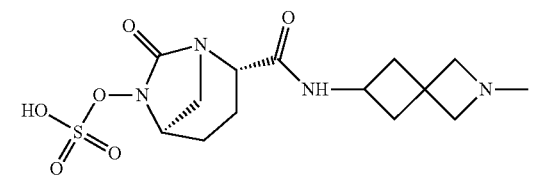
6
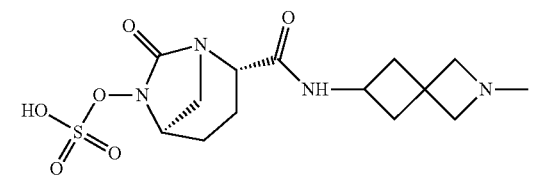
6-1
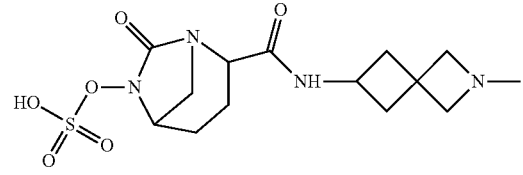

103 -continued
6-2
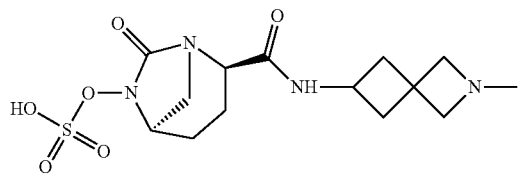
7
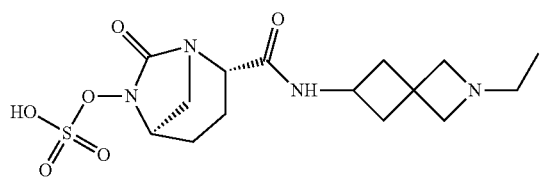
7-1
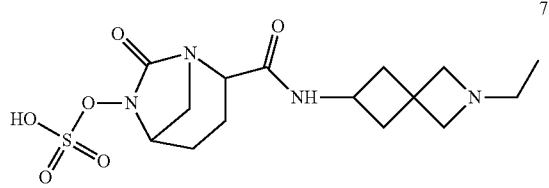
7-2
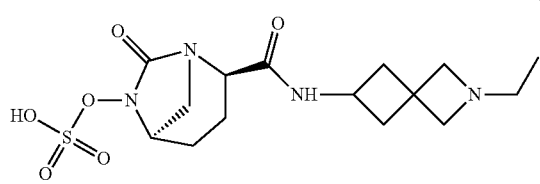
8
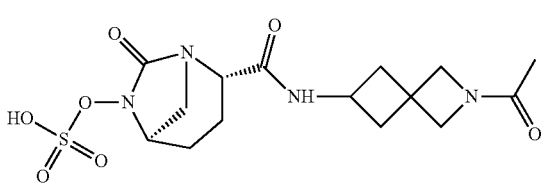
8-1
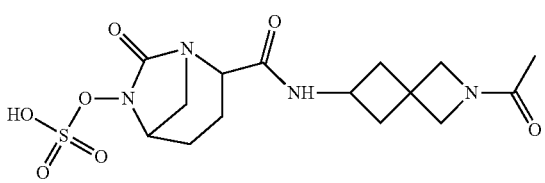
9
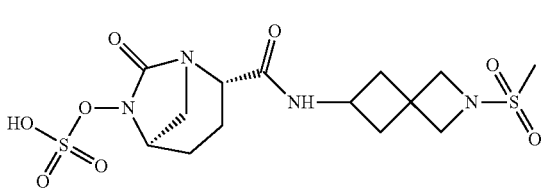
9-1
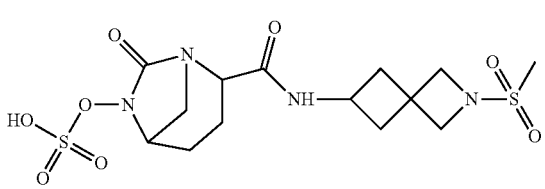
104 -continued
10
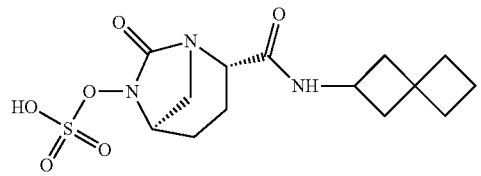
10-1
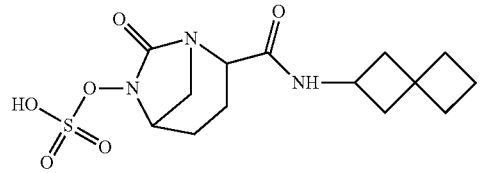
11
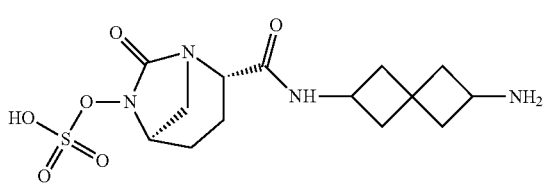
11-1
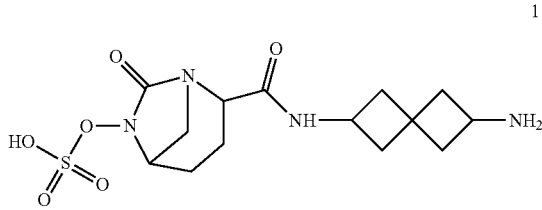
12
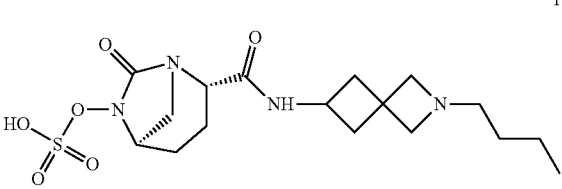
12-1
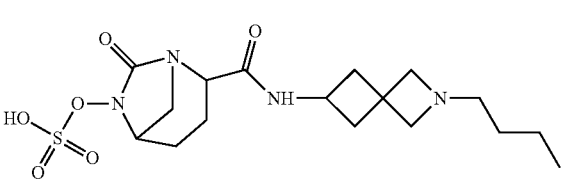
13
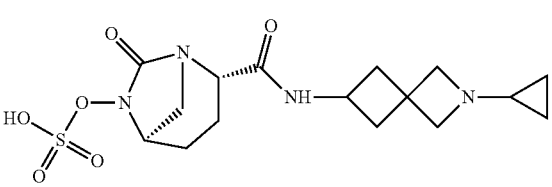
13-1
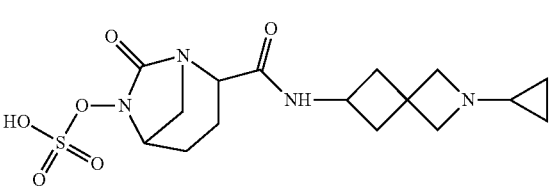

13-2

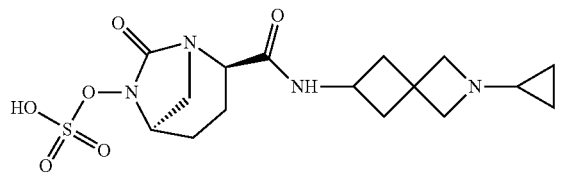

14

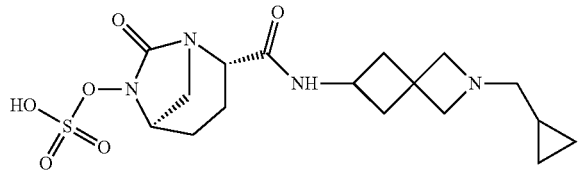

14-1

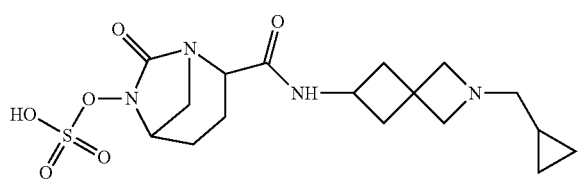

14-2

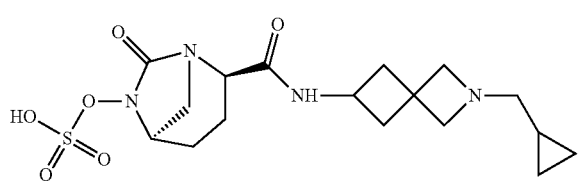

15

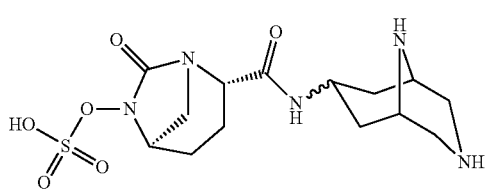

15-1

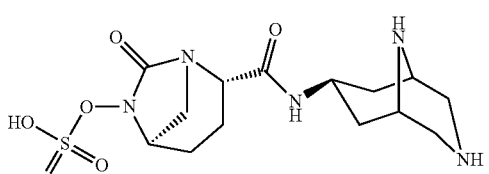

or 15-2

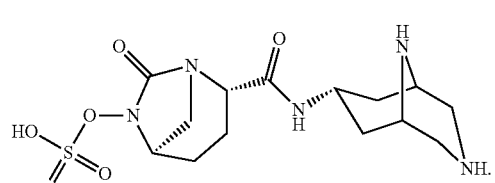

16. A pharmaceutical preparation, comprising the compound or a pharmaceutically acceptable salt, ester, solvate or stereoisomer thereof according to claim 1, characterized by comprising one or more pharmaceutically acceptable carriers and/or diluents; optionally, further including one or more second therapeutic agents, which are selected from the group consisting of anti-inflammatory agents, matrix metallo-proteinase inhibitors, lipoxygenase inhibitors, cytokine antagonists, immunosuppressors, anticancer agents, antiviral agents, growth factor regulators, immunoregulators or compounds against excessive proliferation of blood vessels.

17. A method for treating a bacterial drug-resistant disease caused by β-lactamase in a subject in need thereof, comprising administering a β-lactamase inhibitor medicament comprising the compound of claim 1 or a pharmaceutically acceptable salt, ester, solvate, or stereoisomer of the compound of claim 1,
wherein the bacterial drug-resistant disease is selected from those caused by type A β-lactamase, type B metallo-β-lactamase, type C β-lactamase, or type D β-lactamase; and
wherein the bacterial drug-resistant disease is caused by a bacterium selected from a gram-positive bacterium or a gram-negative bacterium.

18. The method of claim 17, wherein the type A β-lactamase is CTX-M, TEM-1 or SHV-1.

19. The method of claim 17, wherein the type B metallo-β-lactamase is NDM-1, IMP or VIM.

20. The method of claim 17, wherein the type C β lactamase is AmpC.

21. The method of claim 17, wherein the type D β lactamase is OXA.

22. The method of claim 17, wherein the gram-positive bacterium is selected from one or more of *Staphylococcus aureus, Staphylococcus epidermidis, Streptococcus agalactiae, Enterococcus faecalis, Streptococcus pneumoniae, Streptococcus pyogenes, Enterococcus faecium,* or *Clostridium difficile.*

23. The method of claim 17, wherein the gram-negative bacterium is selected from one or more of *Citrobacter, Citrobacter freundii, Enterobacter cloacae, Klebsiella pneumoniae, Escherichia coli, Proteus vulgaris, salmonella, Serratia marcescens, Shiga's bacillus, Pseudomonas aeruginosa, Mucositis mora* bacteria, *Neisseria gonorrhoeae, Neisseria meningitidis, Diplococcus gonorrhoeae, Acinetobacter* Species, *Burkholderia* Species, *Bacterium flexuosus, Helicobacter pylori, Bacillus comma, Klebsiella, Haemophilus influenzae, Mycobacterium avium* complex, *Mycobacterium abscessus, Mycoboterium kansasii, Mycobacterium ulcerans, Chlamydophila pneumoniae, Chlamydia trachomatis, Haemophilus influenzae, Streptococcus pyogenes, β-Streptococcus hemolyticus, Acinetobacter baumannii, Pseudomonas aeruginosa, Bacteroides fragilis, Bacillus cereus* or *Stenotrophomonas maltophilia.*

24. A method for treating an infectious disease caused by bacteria in a subject in need thereof, comprising administering a medicament comprising the compound of claim 1 or a pharmaceutically acceptable salt, ester, solvate, or stereoisomer of the compound of claim 1,
wherein the infectious disease caused by bacteria is selected from one or more of the following: upper respiratory tract infection, lower respiratory tract infection, complicated urinary tract infection and other urinary tract infection, central nervous system infection, ear infection, infections of pleura, lung and bronchia, pulmonary tuberculosis, co-occurring or non-co-occurring urinary tract infection, intra-abdominal infection, cardiovascular infection, bloodstream infection, septicemia, bacteremia, CNS infection, skin or soft-tissue infection, GI infection, bone and joint infection, genital infection, eye infection, granuloma infection, co-occurring or non-co-occurring skin and skin structure infections, catheter-related infection, pharyngitis, sinusitis, otitis extern, otitis media, bronchitis, empyema, pneumonia, community acquired bacterial pneumonia, hospital acquired pneumonia, hospital acquired bacterial pneumonia, ventilator-associated pneumonia, diabetic foot infection, vancomycin resistant enterococcus infection, urocystitis and nephropyelitis, renal calculus, prostatitis, peritonitis, complicated intra-abdominal infections and other intra-abdominal infections, dialysis-associated peritonitis, viscera abscess, endocarditis, myocarditis, pericarditis, infusion-related septicemia, meningitis, cerebritis, brain abscess, osteomyelitis, arthritis, genital ulcer, urethritis, vaginitis, cervicitis, gingivitis, conjunctivitis, keratitis, entophthalmia, infections in cystic fibrosis patients or infections in Febrile neutropenia patients.

* * * * *